US007897343B2

(12) United States Patent
Wensvoort et al.

(10) Patent No.: US 7,897,343 B2
(45) **Date of Patent: *Mar. 1, 2011**

(54) CAUSATIVE AGENT OF THE MYSTERY SWINE DISEASE, VACCINE COMPOSITIONS AND DIAGNOSTIC KITS

(75) Inventors: Gert Wensvoort, Havelte (NL); Catharinus Terpstra, Lelystad (NL); Maria Anthonis Joannes Pol, Lelystad (NL); Jacobus Maria Robertus Moormann, Dronten (NL); Jacoba Maria Johanna Meulenberg, Amsterdam (NL)

(73) Assignee: Boehringer Ingelheim Vetmedica GmbH (DE)

( * ) Notice: Subject to any disclaimer, the term of this patent is extended or adjusted under 35 U.S.C. 154(b) by 0 days.
This patent is subject to a terminal disclaimer.

(21) Appl. No.: 11/966,036

(22) Filed: Dec. 28, 2007

(65) Prior Publication Data

US 2008/0108107 A1 May 8, 2008

Related U.S. Application Data

(60) Continuation of application No. 10/891,444, filed on Jul. 14, 2004, now Pat. No. 7,335,473, which is a continuation of application No. 10/226,065, filed on Aug. 21, 2002, now Pat. No. 6,806,086, which is a division of application No. 09/565,864, filed on May 5, 2000, now Pat. No. 6,455,245, which is a division of application No. 08/747,863, filed on Nov. 13, 1996, now Pat. No. 6,197,310, which is a division of application No. 08/157,005, filed on Nov. 26, 1993, now Pat. No. 5,620,691.

(30) Foreign Application Priority Data

Jun. 6, 1991 (EP) .................................... 91201398
Mar. 18, 1992 (EP) .................................... 92200781

(51) Int. Cl.
*C12Q 1/68* (2006.01)

(52) U.S. Cl. .......................................................... 435/6

(58) Field of Classification Search .............. 435/6, 69.1
See application file for complete search history.

(56) References Cited

U.S. PATENT DOCUMENTS

| | | | |
|---|---|---|---|
| 4,468,346 | A | 8/1984 | Paul et al. |
| 5,213,759 | A | 5/1993 | Castberg et al. |
| 5,419,907 | A | 5/1995 | Paul et al. |
| 5,476,778 | A | 12/1995 | Chladek et al. |
| 5,510,258 | A | 4/1996 | Sanderson et al. |
| 5,587,164 | A | 12/1996 | Sanderson et al. |
| 5,597,721 | A | 1/1997 | Brun et al. |
| 5,620,691 | A | 4/1997 | Wensvoort et al. |
| 5,674,500 | A | 10/1997 | Peeters et al. |
| 5,677,429 | A | 10/1997 | Benfield |
| 5,683,865 | A | 11/1997 | Collins et al. |
| 5,690,940 | A | 11/1997 | Joo |
| 5,695,766 | A | 12/1997 | Paul et al. |
| 5,698,203 | A | 12/1997 | Visser et al. |
| 5,789,388 | A | 8/1998 | Visser et al. |
| 5,840,563 | A | 11/1998 | Chladek et al. |
| 5,846,805 | A | 12/1998 | Collins et al. |
| 5,858,729 | A | 1/1999 | Van Woensel et al. |
| 5,866,401 | A | 2/1999 | Hesse |
| 5,888,513 | A | 3/1999 | Plana Duran et al. |
| 5,910,310 | A | 6/1999 | Heinen et al. |
| 5,925,359 | A | 7/1999 | Van Woensel et al. |
| 5,976,537 | A | 11/1999 | Mengeling et al. |
| 5,989,563 | A | 11/1999 | Chladek et al. |
| 5,998,601 | A | 12/1999 | Murtaugh et al. |
| 6,001,370 | A | 12/1999 | Burch et al. |
| 6,015,663 | A | 1/2000 | Wesley et al. |
| 6,110,467 | A | 8/2000 | Paul et al. |
| 6,197,310 | B1 | 3/2001 | Wensvoort et al. |
| 6,251,397 | B1 | 6/2001 | Paul et al. |
| 6,251,404 | B1 | 6/2001 | Paul et al. |
| 6,380,376 | B1 | 4/2002 | Paul et al. |
| 6,455,245 | B1 | 9/2002 | Wensvoort et al. |
| 6,498,008 | B2 | 12/2002 | Collins et al. |
| 6,592,873 | B1 | 7/2003 | Paul et al. |
| 6,806,086 | B2 | 10/2004 | Wensvoort et al. |
| 7,335,473 | B2 * | 2/2008 | Wensvoort et al. ............... 435/6 |

FOREIGN PATENT DOCUMENTS

| | | |
|---|---|---|
| EP | 0 595 436 A2 | 5/1994 |
| GB | 2 282 811 A | 4/1995 |
| WO | 92/21375 A1 | 12/1992 |
| WO | 93/03760 A1 | 3/1993 |
| WO | 93/06211 A1 | 4/1993 |
| WO | 93/07898 A1 | 4/1993 |
| WO | 94/18311 A1 | 8/1994 |
| WO | 95/31550 A1 | 11/1995 |
| WO | 96/04010 A1 | 2/1996 |

(Continued)

OTHER PUBLICATIONS

Abstracts of Papers Presented at teh 71st Annual Meeting of the Conference of Research Workers in Animal Disease, Nos. 1-6, Nov. 5,6, 1990, 2 pages. "Advances in Veterinary Virology 2", Veterinary Microbiology, 33(1992), pp. 185-193.

Boursnell et al., "Completion of the Sequence of the Genome of the Coronavirus Avian Infectious Bronchitis Virus", Journal of General Virology 68, 1986, pp. 57-77.

Christianson et al., "Experimental reproduction of swine infertility and respiratory syndrome in pregnant sows", Am J Vet Res., vol. 53, No. 4, Apr. 1992, pp. 485-488.

Christianson et al., "Porcine reproductive and respiratory syndrome: A review", Swine Health and Production, vol. 2, No. 2, pp. 10-28, Mar. and Apr. 1994.

(Continued)

*Primary Examiner* — Ali R. Salimi

(74) *Attorney, Agent, or Firm* — Michael P. Morris; Joyce L. Morrison

(57) ABSTRACT

Composition of matter comprising the causative agent of Mystery Swine Disease, Lelystad Agent, in a live, attenuated, dead, or recombinant form, or a part or component of it. Vaccine compositions and diagnostic kits based thereon. Recombinant nucleic acid comprising a Lelystad Agent-specific nucleotide sequence. Peptides comprising a Lelystad Agent-specific amino acid sequence. Lelystad Agent-specific antibodies.

12 Claims, 19 Drawing Sheets

FOREIGN PATENT DOCUMENTS

| WO | 96/06619 A1 | 3/1996 |
|---|---|---|
| WO | 96/40932 A1 | 12/1996 |

OTHER PUBLICATIONS

Collins et al., "Isolation of swine infertility and respiratory syndrome virus (isolate ATCC VR-2332) in North America and experimental reproduction of the disease in gnotobiotic pigs", J Vet Diam Invest, 4:117-126 (1 992).

Den Boon et al., "Equine Arteritis Virus Is Not a Togavirus but Belongs to the Coronaviruslike Superfamily", Journal of Virology, vol. 65, No. 6, pp. 2910-2920, 1991.

De Vries et al., "All subgenomic mRNAs of equine arteritis virus contain in a common leader sequence", Nucleic Acids Research, vol. 18, No. I 1, 1990, pp. 3241-3247.

"Diseases Of Swine", Sixth Edition, Iowa State University Press, 1986, pp. 244-315.

Duran et al., "Recombinant Baculovirus Vaccines Against Porcine Reproductive And Respiratory Syndrome (PRRS)", Abstracts PRRS, Aug. 9-10, 1995, Copenhagen, Denmark, 2 pages.

Dutch Team Isolates Mystery Pig Disease Agent, Animal Pharrn, 230, p. 21, Jun. 21, 1991.

Dykhuizen et al., "Determining the Economic Impact of the 'New' Pig Disease", Porcine Reproductive and Respiratory Syndrome, A Report on the Seminar Held in Brussels on Nov. 4-5, 1991 and Organized by the European Commission, pp. 53-60.

Godeny et al., "Map Location of Lactate Dehydrogenase-Elevating Virus (LDV) Capsid Protein (VpI) Gene", Virology 177, (1 990), pp. 768-771 (1 990).

Godeny et al., "The 3' Terminus of Lactate Dehydrogenase-Elevating Virus Genome RNA Does Not Contain Togavirus or Flavivirus Conserved Sequences", Virology 72, pp. 647-650 (1989).

Joo et al., "Encephalomyocarditis Virus As A Potential Cause For Mystery Swine Disease", Livestock Conservation Institute, Denver, CO, pp. 62-66, Oct. 6, 1990.

Kuo et al., "A Nested Set of Eight RNAs Is Formed in Macrophages Infected with Lactate Dehydrogenase-Elevating Virus", Journal of Virology vol. 65, No. 9, Sep. 1991, pp. 51 18-5123.

Keffaber, K., "Reproductive Failure of Unknown Etiology", AASP Newsletter, vol. I, No. 2, Sep.-Oct. 1989, pp. 1,4-5,8-10.

Loula, Timothy, "Mystery Pig Disease", Ami-Practice, vol. 12, No. 1, pp. 29-34, Jan./Feb. 1991, 7 pages.

Martin et al., Can J. Coma. Med., 49(1):1-9, 1985.

McCullough et al., "9. Experimental Transmission Of Mystery Swine Disease", The New Pig Disease Porcine Respiration And Reproductive Syndrome, A report on the seminar/workshop held in Brussels on Apr. 29-30, 1991, pp. 46-52.

Meredith MJ, "Porcine Reproductive and Respiratory Syndrome (PRRS)", Pig Disease Information Center, 1st North American Edition, University of Cambridge, pp. 1-57, Aug. 1994.

Moormann et al., "Molecular Cloning and Nucleotide Sequence of Hog Cholera Virus Strain Brescia and Mapping of the Genomic Region Encoding Envelope Protein E1 I", Virology 177, pp. 184-198 (1990).

Morrison et al., "Brief Communications Serologic evidence incriminating a recently isolated virus (ATCC VR-2332) as the cause of swine infertility and respiratory syndrome (SIRS)", J Vet Diagn. Invest, 4:186-188 (1 992).

Murphy et al., "Immunization Against Virus"in Virology~2nd ed., vol. 1, Fields et al, eds. Raven Press, NY, 1990, pp. 469-502.

Notice of Opposition by Akzo Nobel against European Patent No. 0 587 780, Nov. 28, 1995, EP.

Notice of Opposition by Cyandmid Iberica against European Patent No. 0 587 780 Nov. 28, 1995, EP.

Order and Opinion of the Court dated Oct. 26, 1999, Boehringer Ingelheirn Vetrnedica v. Scheriner-Plough Corporation, Civil No. 98-5703 (HAA), United States District Court, District of New Jersey.

Pathological, ultrastructural, and immunohistochemical changes caused by . . . , The Veterinary Quarterly, vol. 13, No. 3, Jul. 1991, pp. 137-143.

Pol et al., "Pathological, ultrastructural, and imrnunohistochemical changes caused by Lelystad virus in experimentally induced infections of mystery swine disease (synonym: porcine epidemic abortion and respiratory syndrome (PEARS))", The Veterinary Quaterly, vol. 13, No. 3, Jul. 1991, pp. 137-143.

Polson et al., "An evaluation of the financial impact of Porcine Reproductive and Respiratory Syndrome (PRRS) in nursery pigs", Proceedings of the 13th International Pin Veterinary Society Congress, p. 3 1, Jun. 1994.

Response to Opposition to European Patent No. 0 587 780, Aug. 30, 1996.

"Revision of the taxonomy of the Coronavirus, Torovirus and Arterivirus genera", Arch w, vol. 135, pp. 227-239, 1994.

Saif L.S., Veterinary Microbiology, 37:285-297, 1993.

Scottf.W., Adv. Exd. Med. Biol., 218:569-576, 1987.

Snijder et al., "The carboxyl-terminal part of the putative Beme virus polymerase is expressed by ribosomal frameshifting and contains sequence motifs which indicate that toro- and coronaviruses are evolutionarily related", Nucleic Acids Research, vol. 18, No. 15, pp. 4535-4542, 1990.

Terpstra et al., "Experimental reproduction of porcine epidemic abortion and respiratory syndrome (mystery induced infections of mystery swine disease (synonym: porcine epidemic abortion and respiratory syndrome (PEARS)", The Veterinary Quarterly, vol. 13, No. 3, Jul. 199 1, pp. 13 1-1 36.

Timony PJ, "Equine Viral Arteritis", Manual of Standards for Diagnostic Tests and Vaccines, pp. 493-499,1992.

Van Z1JL et al., "Live Attenuated Pseudorabies Virus Expressing Envelope Glycoprotein El of Hog Cholera Virus Protects Swine against both Pseudorabies and Hog Cholera", Journal of Virology, vol. 65, No. 5, May 1991, pp. 2761-2765.

Veterinary Bulletin, vol. 58, No. 11, 1988, Nos. 6903-6909, p. 932.

Veterinary Bulletin, vol. 60, No. 3, 1990, Nos. 1536-1551, pp. 255-256.

Visser, Nicolaas, "Declaration Of Dr. N. Visser", Nov. 14, 1995, pp. 1-11.

Wardley et al., "The Host Response to African Swine Fever Virus", Prog. Med. Virology., vol. 34, pp. 180-192 (1987).

Wenswoort et al., "Antigenic comparison of Lelystad virus and swine infertility and respiratory syndrome (SIRS) virus", J Vet Diagn. Invest, vol. 4, pp. 134-138, 1992.

Wensvoort et al., "Blue ear" disease, The Veterinary Record, vol. 128, No. 128, Jun. 15, 1991, col. I, letter, p. 574.

Wensvoort et al., "Mystery swine disease in the Netherlands: the isolation of Lelystad virus", The Veterinary Quarterly, vol. 13, No. 3, Jul. 1991, pp. 121-130.

Wensvoort et al., "The Porcine Reproductive and Respiratory Syndrome; Characteristics and diagnosis of the causative virus", Veterinary Biotechnology Newsletter, Vol. 3, pp. 113-120, 1993.

Yoon et al., "Isolation of a cytophathic virus from weak pigs on farms with a history of swine infertility and respiratory syndrome", J. Vet Diagn Invest, 4: 139-143 (1992).

Brinton-Darnell et al., Structure and chemical-physical characteristics of lactate dehydrogenase-elevating virus and its RNA, J. Virology., 1975, pp. 420 433, vol. 16.

Horzinek et al., Studies on the substructure of togaviruses 11. Analysis of equine arteritis, rubella, bovine viral diarrhea and hog cholera viruses, Arch. Gesarnte Virusforsch., 1971, pp. 306 3 18, vol. 33.

Hyllseth, B., Structural proteins of equine arteritis virus, Arch. Gesarnte Virusforsch, 1973, pp. 177 188, vol. 40.

Masurel, N., Swine influenza virus and the recycling of influenza-A viruses in man , Lancet ii, 1976, pp. 244 247.

Mengeling et al., Mystery Pig Disease: Evidence and considerations for its etiology, In: Proceedings of the Mystery Swine Disease Committee Meeting, Oct. 6, 1990, Denver, Colorado, Livestock Conservation Institute, Madison, WI , USA.

Moormann et a., Hog cholera virus: identification and characterization of the viral RNA and virus-specific RNA synthesized in infected swine kidney cells, Virus Res. 1988, pp. 281 291, vol. 11.

Rottier et al., Predicted membrane topology of the coronavirus protein El, Biochemistry, 1986, pp. 1335 1339,,Val. 25.

Sethna et al., Coronavirus subgenomic minus-strand RNAs and the potential for mRNA replicons, Proc. Natl. Acad. Sci. 1989, USA, pp. 5626 5630, vol. 86.

Snijder et al., A 3'-coterminal nested set of independently transcribed rnRNAs is generated during Beme virus replication. J. Virol., 1990b, pp. 355 363, vol. 64.

Spaan et a., Coronaviruses: structure and genome expression, J. Gen. Virol., 1988, pp. 2939 2952, vol. 69.

Wensvoort et al., Bovine viral diarrhea infections in piglets from sows vaccinated against swine fever with contaminated vaccine, Res. Vet. Sci. 1988, pp. 143-148, vol. 45.

Wensvoort et al., An enzyme immunoassay, employing monoclonal antibodies and detecting specifically antibodies to classical swine fever virus, Vet. Microbiol., 1988, pp. 129-140, vol. 17.

Wensvoort et al., Production of monoclonal antibodies against swine fever virus and their use in laboratory diagnosis, Vet. Microbiol., 1986, pp. 101-108, vol. 12.

Wensvoort et al., Characterization of porcine and some ruminant pestiviruses by cross-neutralization, Vet. Microbiol., 1989, pp. 291-306, vol. 20.

Zeijst et a., The genome of equine arteritis virus, Virology, 1975, pp. 418-425, vol. 68.

Nielsen et al., Generation of an Infectious Clone of VR-2332, a Highly Virulent North American-Type Isolate of Porcine Reproductive and Respiratory Syndrome Virus, Journal of Virology, Mar. 2003, pp. 3702-1 I, vol. 77, No. 6.

* cited by examiner

FIG. 1a

```
GGGTATTCCCCCTACATACACGACACTTCTAGTGTTTGTGTACCTTGGAGGCGTGGGTAC            60
                                25
AGCCCCGCCCCACCCCTTGGCCCCTGTTCTAGCCCAACAGGTATCCTTCTCTCTCGGGGC           120
GAGTGCGCCGCCTGCTGCTCCCTTGCAGCGGGAAGGACCTCCCGAGTATTTCCGGAGAGC           180
ACCTGCTTTACGGGATCTCCACCCTTTAACCATGTCTGGGACGTTCTCCCGGTGCATGTG           240
              ORF1A        M   S   G   T   F   S   R   C   M   C       10
CACCCCGGCTGCCCGGGTATTTTGGAACGCCGGCCAAGTCTTTTGCACACGGTGTCTCAG           300
  T   P   A   A   R   V   F   W   N   A   G   Q   V   F   C   T   R   C   L   S       30
TGCGCGGTCTCTTCTCTCCAGAGCTTCAGGACACTGACCTCGGTGCAGTTGGCTTGTT            360
  A   R   S   L   L   S   P   E   L   Q   D   T   D   L   G   A   V   G   L   F       50
TTACAAGCCTAGGGACAAGCTTCACTGGAAAGTCCCTATCGGCATCCCTCAGGTGGAATG          420
  Y   K   P   R   D   K   L   H   W   K   V   P   I   G   T   P   Q   V   E   C       70
TACTCCATCCGGGTGCTGTTGGCTCTCAGCTGTTTTCCCTTTGGCGCGTATGACCTCCGG          480
  T   P   S   G   C   C   W   L   S   A   V   F   P   L   A   R   M   T   S   G       90
CAATCACAACTTCCTCCAACGACTTGTGAAGGTTGCTGATGTTTTGTACCGTGACGGTTG          540
  N   H   N   F   L   Q   R   L   V   K   V   A   D   V   L   Y   R   D   G   C      110
CTTGGCACCTCGACACCTTCGTGAACTCCAAGTTTACGAGCGCGGCTGCAACTGGTACCC          600
  L   A   P   R   H   L   R   E   L   Q   V   Y   E   R   G   C   N   W   Y   P      130
GATCACGGGGCCCGTGCCCGGGATGGGTTTGTTTGCGAACTCCATGCACGTATCCGACCA          660
  I   T   G   P   V   P   G   M   G   L   F   A   N   S   M   H   V   S   D   Q      150
GCCGTTCCCTGGTGCCACCCATGTGTTGACTAACTCGCCTTTGCCTCAACAGGCTTGTCG          720
  P   F   P   G   A   T   H   V   L   T   N   S   P   L   P   Q   Q   A   C   R      170
GCAGCCGTTCTGTCCATTTGAGGAGGCTCATTCTAGCGTGTACAGGTGGAAGAAATTTGT          780
  Q   P   F   C   P   F   E   E   A   H   S   S   V   Y   R   W   K   K   F   V      190
GGTTTTCACGGACTCCTCCCTCAACGGTCGATCTCGCATGATGTGGACGCCGGAATCCGA          840
  V   F   T   D   S   S   L   N   G   R   S   R   M   M   W   T   P   E   S   D      210
TGATTCAGCCGCCCTGGAGGTACTACCGCCTGAGTTAGAACGTCAGGTCGAAATCCTCAT          900
  D   S   A   A   L   E   V   L   P   P   E   L   E   R   Q   V   E   I   L   I      230
TCGGAGTTTTCCTGCTCATCACCCTGTCGACCTGGCCGACTGGGAGCTCACTGAGTCCCC          960
  R   S   F   P   A   H   H   P   V   D   L   A   D   W   E   L   T   E   S   P      250
TGAGAACGGTTTTTCCTTCAACACGTCTCATTCTTGCGGTCACCTTGTCCAGAACCCCGA         1020
  E   N   G   F   S   F   N   T   S   H   S   C   G   H   L   V   Q   N   P   D      270
```

FIG. 1b

```
CGTGTTTGATGGCAAGTGCTGGCTCTCCTGCTTTTTGGGCCAGTCGGTCGAAGTGCGCTG    1080
 V   F   D   G   K   C   W   L   S   C   F   L   G   Q   S   V   E   V   R   C    290

CCATGAGGAACATCTAGCTGACGCCTTCGGTTACCAAACCAAGTGGGGCGTGCATGGTAA    1140
 H   E   E   H   L   A   D   A   F   G   Y   Q   T   K   W   G   V   H   G   K    310

GTACCTCCAGCGCAGGCTTCAAGTTCGCGGCATTCGTGCTGTAGTCGATCCTGATGGTCC    1200
 Y   L   Q   R   R   L   Q   V   R   G   I   R   A   V   V   D   P   D   G   P    330

CATTCACGTTGAAGCGCTGTCTTGCCCCAGTCTTGGATCAGGCACCTGACTCTGGATGA    1260
 I   H   V   E   A   L   S   C   P   Q   S   W   I   R   H   L   T   L   D   D    350

TGATGTCACCCCAGGATTCGTTCGCCTGACATCCCTTCGCATTGTGCCGAACACAGAGCC    1320
 D   V   T   P   G   F   V   R   L   T   S   L   R   I   V   P   N   T   E   P    370

TACCACTTCCCGGATCTTTCGGTTTGGAGCGCATAAGTGGTATGGCGCTGCCGGCAAACG    1380
 T   T   S   R   I   F   R   F   G   A   H   K   W   Y   G   A   A   G   K   R    390

GGCTCGTGCTAAGCGTGCCGCTAAAAGTGAGAAGGATTCGGCTCCCACCCCCAAGGTTGC    1440
 A   R   A   K   R   A   A   K   S   E   K   D   S   A   P   T   P   K   V   A    410

CCTGCCGGTCCCCACCTGTGGAATTACCACCTACTCTCCACCGACAGACGGGTCTTGTGG    1500
 L   P   V   P   T   C   G   I   T   T   Y   S   P   P   T   D   G   S   C   G    430

TTGGCATGTCCTTGCCGCCATAATGAACCGGATGATAAATGGTGACTTCACGTCCCTCT    1560
 W   H   V   L   A   A   I   M   N   R   M   I   N   G   D   F   T   S   P   L    450

GACTCAGTACAACAGACCAGAGGATGATTGGGCTTCTGATTATGATCTTGTTCAGGCGAT    1620
 T   Q   Y   N   R   P   E   D   D   W   A   S   D   Y   D   L   V   Q   A   I    470

TCAATGTCTACGACTGCCTGCTACCGTGGTTCGGAATCGCGCCTGTCCTAACGCCAAGTA    1680
 Q   C   L   R   L   P   A   T   V   V   R   N   R   A   C   P   N   A   K   Y    490

CCTTATAAAACTTAACGGAGTTCACTGGGAGGTAGAGGTGAGGTCTGGAATGGCTCCTCG    1740
 L   I   K   L   N   G   V   H   W   E   V   E   V   R   S   G   M   A   P   R    510

CTCCCTTTCTCGTGAATGTGTGGTTGGCGTTTGCTCTGAAGGCTGTGTCGCACCGCCTA    1800
 S   L   S   R   E   C   V   V   G   V   C   S   E   G   C   V   A   P   P   Y    530

TCCAGCAGACGGGCTACCTAAACGTGCACTCGAGGCCTTGGCGTCTGCTTACAGACTACC    1860
 P   A   D   G   L   P   K   R   A   L   E   A   L   A   S   A   Y   R   L   P    550

CTCCGATTGTGTTAGCTCTGGTATTGCTGACTTTCTTGCTAATCCACCTCCTCAGGAATT    1920
 S   D   C   V   S   S   G   I   A   D   F   L   A   N   P   P   P   Q   E   F    570

CTGGACCCTCGACAAAATGTTGACCTCCCCGTCACCAGAGCGGTCCGGCTTCTCTAGTTT    1980
 W   T   L   D   K   M   L   T   S   P   S   E   R   S   G   F   S   S   L    590
```

FIG. 1c

```
GTATAAATTACTATTAGAGGTTGTTCCGCAAAAATGCGGTGCCACGGAAGGGGCTTTCAT    2040
  Y  K  L  L  E  V  V  P  Q  K  C  G  A  T  E  G  A  F  I       610

CTATGCTGTTGAGAGGATGTTGAAGGATTGTCCGAGCTCCAAACAGGCCATGGCCCTTCT    2100
  Y  A  V  E  R  M  L  K  D  C  P  S  S  K  Q  A  M  A  L  L    630

GGCAAAAATTAAAGTTCCATCCTCAAAGGCCCCGTCTGTGTCCCTGGACGAGTGTTTCCC    2160
  A  K  I  K  V  P  S  S  K  A  P  S  V  S  L  D  E  C  F  P    650

TACGGATGTTTTAGCCGACTTCGAGCCAGCATCTCAGGAAAGGCCCCAAAGTTCCGGCGC    2220
  T  D  V  L  A  D  F  E  P  A  S  Q  E  R  P  Q  S  S  G  A    670

A
TGCTGTTGTCCTGTGTTCACCGGATGCAAAAGAGTTCGAGGAAGCAGCCCCGGAAGAAGT    2280
  A  V  V  L  C  S  P  D  A  K  E  F  E  E  A  A  P  E  E  V    690

TCAAGAGAGTGGCCACAAGGCCGTCCACTCTGCACTCCTTGCCGAGGGTCCTAACAATGA    2340
  Q  E  S  G  H  K  A  V  H  S  A  L  L  A  E  G  P  N  N  E    710

GCAGGTACAGGTGGTTGCCGGTGAGCAACTGAAGCTCGGCGGTTGTGGTTTGGCAGTCGG    2400
  Q  V  Q  V  V  A  G  E  Q  L  K  L  G  G  C  G  L  A  V  G    730

GAATGCTCATGAAGGTGCTCTGGTCTCAGCTGGTCTAATTAACCTGGTAGGCGGGAATTT    2460
  N  A  H  E  G  A  L  V  S  A  G  L  I  N  L  V  G  G  N  L    750

GTCCCCCTCAGACCCCATGAAAGAAAACATGCTCAATAGCCGGGAAGACGAACCACTGGA    2520
  S  P  S  D  P  M  K  E  N  M  L  N  S  R  E  D  E  P  L  D    770

TTTGTCCCAACCAGCACCAGCTTCCACAACGACCCTTGTGAGAGAGCAAACACCCGACAA    2580
  L  S  Q  P  A  P  A  S  T  T  T  L  V  R  E  Q  T  P  D  N    790

CCCAGGTTCTGATGCCGGTGCCCTCCCCGTCACCGTTCGAGAATTTGTCCCGACGGGGCC    2640
  P  G  S  D  A  G  A  L  P  V  T  V  R  E  F  V  P  T  G  P    810

TATACTCTGTCATGTTGAGCACTGCGGCACGGAGTCGGGCGACAGCAGTTCGCCTTTGGA    2700
  I  L  C  H  V  E  H  C  G  T  E  S  G  D  S  S  S  P  L  D    830

TCTATCTGATGCGCAAACCCTGGACCAGCCTTTAAATCTATCCCTGGCCGCTTGGCCAGT    2760
  L  S  D  A  Q  T  L  D  Q  P  L  N  L  S  L  A  A  W  P  V    850

GAGGGCCACCGCGTCTGACCCTGGCTGGGTCCACGGTAGGCGCGAGCCTGTCTTTGTAAA    2820
  R  A  T  A  S  D  P  G  W  V  H  G  R  R  E  P  V  F  V  K    870

GCCTCGAAATGCTTTCTCTGATGGCGATTCAGCCCTTCAGTTCGGGGAGCTTTCTGAATC    2880
  P  R  N  A  F  S  D  G  D  S  A  L  Q  F  G  E  L  S  E  S    890
```

FIG. 1d

```
CAGCTCTGTCATCGAGTTTGACCGGACAAAAGATGCTCCGGTGGTTGACGCCCCTGTCGA   2940
  S   S   V   I   E   F   D   R   T   K   D   A   P   V   V   D   A   P   V   D    910

CTTGACGACTTCGAACGAGGCCCTCTCTGTAGTCGATCCTTTCGAATTTGCCGAACTCAA   3000
  L   T   T   S   N   E   A   L   S   V   V   D   P   F   E   F   A   E   L   K    930

GCGCCCGCGTTTCTCCGCACAAGCCTTAATTGACCGAGGCGGTCCACTTGCCGATGTCCA   3060
  R   P   R   F   S   A   Q   A   L   I   D   R   G   G   P   L   A   D   V   H    950

TGCAAAAATAAAGAACCGGGTATATGAACAGTGCCTCCAAGCTTGTGAGCCCGGTAGTCG   3120
  A   K   I   K   N   R   V   Y   E   Q   C   L   Q   A   C   E   P   G   S   R    970

TGCAACCCCAGCCACCAGGGAGTGGCTCGACAAAATGTGGGATAGGGTGGACATGAAAAC   3180
  A   T   P   A   T   R   E   W   L   D   K   M   W   D   R   V   D   M   K   T    990

TTGGCGCTGCACCTCGCAGTTCCAAGCTGGTCGCATTCTTGCGTCCCTCAAATTCCTCCC   3240
  W   R   C   T   S   Q   F   Q   A   G   R   I   L   A   S   L   K   F   L   P   1010

TGACATGATTCAAGACACACCGCCTCCTGTTCCCAGGAAGAACCGAGCTAGTGACAATGC   3300
  D   M   I   Q   D   T   P   P   P   V   P   R   K   N   R   A   S   D   N   A   1030

CGGCCTGAAGCAACTGGTGGCACAGTGGGATAGGAAATTGAGTGTGACCCCCCCCCCAAA   3360
  G   L   K   Q   L   V   A   Q   W   D   R   K   L   S   V   T   P   P   P   K   1050

ACCGGTTGGGCCAGTGCTTGACCAGATCGTCCCTCCGCCTACGGATATCCAGCAAGAAGA   3420
  P   V   G   P   V   L   D   Q   I   V   P   P   P   T   D   I   Q   Q   E   D   1070

TGTCACCCCCTCCGATGGGCCACCCCATGCGCCGGATTTTCCTAGTCGAGTGAGCACGGG   3480
  V   T   P   S   D   G   P   P   H   A   P   D   F   P   S   R   V   S   T   G   1090

CGGGAGTTGGAAAGGCCTTATGCTTTCCGGCACCCGTCTCGCGGGGTCTATCAGCCAGCG   3540
  G   S   W   K   G   L   M   L   S   G   T   R   L   A   G   S   I   S   Q   R   1110

CCTTATGACATGGGTTTTTGAAGTTTTCTCCCACCTCCCAGCTTTTATGCTCACACTTTT   3600
  L   M   T   W   V   F   E   V   F   S   H   L   P   A   F   M   L   T   L   F   1130

CTCGCCGCGGGGCTCTATGGCTCCAGGTGATTGGTTGTTTGCAGGTGTCGTTTTACTTGC   3660
  S   P   R   G   S   M   A   P   G   D   W   L   F   A   G   V   V   L   L   A   1150

TCTCTTGCTCTGTCGTTCTTACCCGATACTCGGATGCCTTCCCTTATTGGGTGTCTTTTC   3720
  L   L   L   C   R   S   Y   P   I   L   G   C   L   P   L   L   G   V   F   S   1170

TGGTTCTTTGCGGCGTGTTCGTCTGGGTGTTTTGGTTCTTGGATGGCTTTTGCTGTATT   3780
  G   S   L   R   R   V   R   L   G   V   F   G   S   W   M   A   F   A   V   F   1190

TTTATTCTCGACTCCATCCAACCCAGTCGGTTCTTCTTGTGACCACGATTCGCCGGAGTG   3840
  L   F   S   T   P   S   N   P   V   G   S   S   C   D   H   D   S   P   E   C   1210
```

FIG. 1e

```
TCATGCTGAGCTTTTGGCTCTTGAGCAGCGCCAACTTTGGGAACCTGTGCGCGGCCTTGT    3900
  H   A   E   L   L   A   L   E   Q   R   Q   L   W   E   P   V   R   G   L   V    1230

GGTCGGCCCCTCAGGCCTCTTATGTGTCATTCTTGGCAAGTTACTCGGTGGGTCACGTTA    3960
  V   G   P   S   G   L   L   C   V   I   L   G   K   L   L   G   G   S   R   Y    1250

TCTCTGGCATGTTCTCCTACGTTTATGCATGCTTGCAGATTTGGCCCTTTCTCTTGTTTA    4020
  L   W   H   V   L   L   R   L   C   M   L   A   D   L   A   L   S   L   V   Y    1270

TGTGGTGTCCCAGGGGCGTTGTCACAAGTGTTGGGGAAAGTGTATAAGGACAGCTCCTGC    4080
  V   V   S   Q   G   R   C   H   K   C   W   G   K   C   I   R   T   A   P   A    1290

GGAGGTGGCTCTTAATGTATTTCCTTTCTCGCGCGCCACCCGTGTCTCTCTTGTATCCTT    4140
  E   V   A   L   N   V   F   P   F   S   R   A   T   R   V   S   L   V   S   L    1310

GTGTGATCGATTCCAAACGCCAAAAGGGGTTGATCCTGTGCACTTGGCAACGGGTTGGCG    4200
  C   D   R   F   Q   T   P   K   G   V   D   P   V   H   L   A   T   G   W   R    1330

CGGGTGCTGGCGTGGTGAGAGCCCCATCCATCAACCACACCAAAAGCCCATAGCTTATGC    4260
  G   C   W   R   G   E   S   P   I   H   Q   P   H   Q   K   P   I   A   Y   A    1350

CAATTTGGATGAAAAGAAAATGTCTGCCCAAACGGTGGTTGCTGTCCCATACGATCCCAG    4320
  N   L   D   E   K   K   M   S   A   Q   T   V   V   A   V   P   Y   D   P   S    1370

TCAGGCTATCAAATGCCTGAAAGTTCTGCAGGCGGGAGGGGCCATCGTGGACCAGCCTAC    4380
  Q   A   I   K   C   L   K   V   L   Q   A   G   G   A   I   V   D   Q   P   T    1390

ACCTGAGGTCGTTCGTGTGTCCGAGATCCCCTTCTCAGCCCCATTTTTCCCAAAAGTTCC    4440
  P   E   V   V   R   V   S   E   I   P   F   S   A   P   F   F   P   K   V   P    1410

AGTCAACCCAGATTGCAGGGTTGTGGTAGATTCGGACACTTTTGTGGCTGCGGTTCGCTG    4500
  V   N   P   D   C   R   V   V   V   D   S   D   T   F   V   A   A   V   R   C    1430
                                                                        C
CGGTTACTCGACAGCACAACTGGTTCTGGGCCGGGGCAACTTTGCCAAGTTAAATCAGAC    4560
  G   Y   S   T   A   Q   L   V   L   G   R   G   N   F   A   K   L   N   Q   T    1450

CCCCCCCAGGAACTCTATCTCCACCAAAACGACTGGTGGGGCCTCTTACACCCTTGCTGT    4620
  P   P   R   N   S   I   S   T   K   T   T   G   G   A   S   Y   T   L   A   V    1470

GGCTCAAGTGTCTGCGTGGACTCTTGTTCATTTCATCCTCGGTCTTTGGTTCACATCACC    4680
  A   Q   V   S   A   W   T   L   V   H   F   I   L   G   L   W   F   T   S   P    1490

TCAAGTGTGTGGCCGAGGAACCGCTGACCCATGGTGTTCAAATCCTTTTTCATATCCTAC    4740
  Q   V   C   G   R   G   T   A   D   P   W   C   S   N   P   F   S   Y   P   T    1510

CTATGGCCCCGGAGTTGTGTGCTCCTCTCGACTTTGTGTGTCTGCCGACGGGGTCACCCT    4800
  Y   G   P   G   V   V   C   S   S   R   L   C   V   S   A   D   G   V   T   L    1530
```

FIG. 1f

```
GCCATTGTTCTCAGCCGTGGCACAACTCTCCGGTAGAGAGGTGGGGATTTTTATTTTGGT    4860
  P  L  F  S  A  V  A  Q  L  S  G  R  E  V  G  I  F  I  L  V    1550

GCTCGTCTCCTTGACTGCTTTGGCCCACCGCATGGCTCTTAAGGCAGACATGTTAGTGGT    4920
  L  V  S  L  T  A  L  A  H  R  M  A  L  K  A  D  M  L  V  V    1570

CTTTTCGGCTTTTTGTGCTTACGCCTGGCCCATGAGCTCCTGGTTAATCTGCTTCTTTCC    4980
  F  S  A  F  C  A  Y  A  W  P  M  S  S  W  I  C  F  F  P       1590

TATACTCTTGAAGTGGGTTACCCTTCACCCTCTTACTATGCTTTGGGTGCACTCATTCTT    5040
  I  L  L  K  W  V  T  L  H  P  L  T  M  L  W  V  H  S  F  L    1610

GGTGTTTTGTCTGCCAGCAGCCGGCATCCTCTCACTAGGGATAACTGGCCTTCTTTGGGC    5100
  V  F  C  L  P  A  A  G  I  L  S  L  G  I  T  G  L  L  W  A    1630

AATTGGCCGCTTTACCCAGGTTGCCGGAATTATTACACCTTATGACATCCACCAGTACAC    5160
  I  G  R  F  T  Q  V  A  G  I  I  T  P  Y  D  I  H  Q  Y  T    1650

CTCTGGGCCACGTGGTGCAGCTGCTGTGGCCACAGCCCCAGAAGGCACTTATATGGCCGC    5220
  S  G  P  R  G  A  A  A  V  A  T  A  P  E  G  T  Y  M  A  A    1670

CGTCCGGAGAGCTGCTTTAACTGGGCGAACTTTAATCTTCACCCCGTCTGCAGTTGGATC    5280
  V  R  R  A  A  L  T  G  R  T  L  I  F  T  P  S  A  V  G  S    1690

CCTTCTCGAAGGTGCTTTCAGGACTCATAAACCCTGCCTTAACACCGTGAATGTTGTAGG    5340
  L  L  E  G  A  F  R  T  H  K  P  C  L  N  T  V  N  V  V  G    1710

CTCTTCCCTTGGTTCCGGAGGGGTTTTCACCATTGATGGCAGAAGAACTGTCGTCACTGC    5400
  S  S  L  G  S  G  G  V  F  T  I  D  G  R  R  T  V  V  T  A    1730

TGCCCATGTGTTGAACGGCGACACAGCTAGAGTCACCGGCGACTCCTACAACCGCATGCA    5460
  A  H  V  L  N  G  D  T  A  R  V  T  G  D  S  Y  N  R  M  H    1750

CACTTTCAAGACCAATGGTGATTATGCCTGGTCCCATGCTGATGACTGGCAGGGCGTTGC    5520
  T  F  K  T  N  G  D  Y  A  W  S  H  A  D  D  W  Q  G  V  A    1770

CCCTGTGGTCAAGGTTGCGAAGGGGTACCGCGGTCGTGCCTACTGGCAAACATCAACTGG    5580
  P  V  V  K  V  A  K  G  Y  R  G  R  A  Y  W  Q  T  S  T  G    1790

TGTCGAACCCGGTATCATTGGGGAAGGGTTCGCCTTCTGTTTTACTAACTGCGGCGATTC    5640
  V  E  P  G  I  I  G  E  G  F  A  F  C  F  T  N  C  G  D  S    1810

GGGGTCACCCGTCATCTCAGAATCTGGTGATCTTATTGGAATCCACACCGGTTCAAACAA    5700
  G  S  P  V  I  S  E  S  G  D  L  I  G  I  H  T  G  S  N  K    1830

ACTTGGTTCTGGTCTTGTGACAACCCCTGAAGGGGAGACCTGCACCATCAAAGAAACCAA    5760
  L  G  S  G  L  V  T  T  P  E  G  E  T  C  T  I  K  E  T  K    1850
```

FIG. 1g

```
GCTCTCTGACCTTTCCAGACATTTTGCAGGCCCAAGCGTTCCTCTTGGGGACATTAAATT    5820
  L  S  D  L  S  R  H  F  A  G  P  S  V  P  L  G  D  I  K  L    1870

GAGTCCGGCCATCATCCCTGATGTAACATCCATTCCGAGTGACTTGGCATCGCTCCTAGC    5880
  S  P  A  I  I  P  D  V  T  S  I  P  S  D  L  A  S  L  L  A    1890

CTCCGTCCCTGTAGTGGAAGGCGGCCTCTCGACCGTTCAACTTTTGTGTGTCTTTTTCCT    5940
  S  V  P  V  V  E  G  G  L  S  T  V  Q  L  L  C  V  F  F  L    1910

TCTCTGGCGCATGATGGGCCATGCCTGGACACCCATTGTTGCCGTGGGCTTCTTTTTGCT    6000
  L  W  R  M  M  G  H  A  W  T  P  I  V  A  V  G  F  F  L  L    1930

GAATGAAATTCTTCCAGCAGTTTTGGTCCGAGCCGTGTTTTCTTTTGCACTCTTTGTGCT    6060
  N  E  I  L  P  A  V  L  V  R  A  V  F  S  F  A  L  F  V  L    1950

TGCATGGGCCACCCCCTGGTCTGCACAGGTGTTGATGATTAGACTCCTCACGGCATCTCT    6120
  A  W  A  T  P  W  S  A  Q  V  L  M  I  R  L  L  T  A  S  L    1970

CAACCGCAACAAGCTTTCTCTGGCGTTCTACGCACTCGGGGGTGTCGTCGGTTTGGCAGC    6180
  N  R  N  K  L  S  L  A  F  Y  A  L  G  G  V  V  G  L  A  A    1990

TGAAATCGGGACTTTTGCTGGCAGATTGTCTGAATTGTCTCAAGCTCTTTCGACATACTG    6240
  E  I  G  T  F  A  G  R  L  S  E  L  S  Q  A  L  S  T  Y  C    2010

CTTCTTACCTAGGGTCCTTGCTATGACCAGTTGTGTTCCCACCATCATCATTGGTGGACT    6300
  F  L  P  R  V  L  A  M  T  S  C  V  P  T  I  I  I  G  L      2030
                                                    G
CCATACCCTCGGTGTGATTCTGTGGTTATTCAAATACCGGTGCCTCCACAACATGCTGGT    6360
  H  T  L  G  V  I  L  W  L  F  K  Y  R  C  L  H  N  M  L  V    2050

TGGTGATGGGAGTTTTTTCAAGCGCCTTCTTCCTACGGTATTTTGCAGAGGGTAATCTCAG    6420
  G  D  G  S  F  S  S  A  F  F  L  R  Y  F  A  E  G  N  L  R    2070

AAAAGGTGTTTCACAGTCCTGTGGCATGAATAACGAGTCCCTAACGGCTGCTTTAGCTTG    6480
  K  G  V  S  Q  S  C  G  M  N  N  E  S  L  T  A  A  L  A  C    2090

CAAGTTGTCACAGGCTGACCTTGATTTTTTGTCCAGCTTAACGAACTTCAAGTGCTTTGT    6540
  K  L  S  Q  A  D  L  D  F  L  S  S  L  T  N  F  K  C  F  V    2110

ATCTGCTTCAAACATGAAAAATGCTGCCGGCCAGTACATTGAAGCAGCGTATGCCAAGGC    6600
  S  A  S  N  M  K  N  A  A  G  Q  Y  I  E  A  A  Y  A  K  A    2130

CCTGCGCCAAGAGTTGGCCTCTCTAGTTCAGATTGACAAAATGAAAGGAGTTTTGTCCAA    6660
  L  R  Q  E  L  A  S  L  V  Q  I  D  K  M  K  G  V  L  S  K    2150
```

FIG. 1h

```
GCTCGAGGCCTTTGCTGAAACAGCCACCCCGTCCCTTGACATAGGTGACGTGATTGTTCT        6720
 L   E   A   F   A   E   T   A   T   P   S   L   D   I   G   D   V   I   V   L         2170

GCTTGGGCAACATCCTCACGGATCCATCCTCGATATTAATGTGGGGACTGAAAGGAAAAC        6780
 L   G   Q   H   P   H   G   S   I   L   D   I   N   V   G   T   E   R   K   T         2190

TGTGTCCGTGCAAGAGACCCGGAGCCTAGGCGGCTCCAAATTCAGTGTTTGTACTGTCGT        6840
 V   S   V   Q   E   T   R   S   L   G   G   S   K   F   S   V   C   T   V   V         2210
                                    A
GTCCAACACACCCGTGGACGCCTTGACCGGCATCCCACTCCAGACACCAACCCCTCTTTT        6900
 S   N   T   P   V   D   A   L   T   G   I   P   L   Q   T   P   T   P   L   F         2230

TGAGAATGGTCCGCGTCATCGCAGCGAGGAAGACGATCTTAAAGTCGAGAGGATGAAGAA        6960
 E   N   G   P   R   H   R   S   E   E   D   D   L   K   V   E   R   M   K   K         2250

ACACTGTGTATCCCTCGGCTTCCACAACATCAATGGCAAAGTTTACTGCAAAATTTGGGA        7020
 H   C   V   S   L   G   F   H   N   I   N   G   K   V   Y   C   K   I   W   D         2270

CAAGTCTACCGGTGACACCTTTTACACGGATGATTCCCGGTACACCCAAGACCATGCTTT        7080
 K   S   T   G   D   T   F   Y   T   D   D   S   R   Y   T   Q   D   H   A   F         2290

TCAGGACAGGTCAGCCGACTACAGAGACAGGGACTATGAGGGTGTGCAAACCACCCCCCA        7140
 Q   D   R   S   A   D   Y   R   D   R   D   S   E   T   P   V   G   T   V   V         2310

ACAGGGATTTGATCCAAAGTCTGAAACCCCTGTTGGCACTGTTGTGATCGGCGGTATTAC        7200
 I   G   G   I   T   Y   Y   E   G   V   Q   T   T   P   Q   Q   G   F   D   P         2330

GTATAACAGGTATCTGATCAAAGGTAAGGAGGTTCTGGTCCCCAAGCCTGACAACTGCCT        7260
 K   N   R   Y   L   I   K   G   K   E   V   L   V   P   K   P   D   N   C   L         2350

TGAAGCTGCCAAGCTGTCCCTTGAGCAAGCTCTCGCTGGGATGGGCCAAACTTGCGACCT        7320
 E   A   A   K   L   S   L   E   Q   A   L   A   G   M   G   Q   T   C   D   L         2370

TACAGCTGCCGAGGTGGAAAAGCTAAAGCGCATCATTAGTCAACTCCAAGGTTTGACCAC        7380
 T   A   A   E   V   E   K   L   K   R   I   I   S   Q   L   Q   G   L   T   T         2390
                                                                    ORF1B
TGAACAGGCTTTAAACTGTTAGCCGCCAGCGGCTTGACCCGCTGTGGCCGCGGCGGCCTA        7440
 E   Q   A   L   N   C   -                                                                   2396
         -   T   G   F   K   L   L   A   A   S   G   L   T   R   C   G   R   G   G   L       19

GTTGTGACTGAAACGGCGGTAAAAATTATAAAATACCACAGCAGAACTTTCACCTTAGGC        7500
 V   V   T   E   T   A   V   K   I   I   K   Y   H   S   R   T   F   T   L   G         39

CCTTTAGACCTAAAAGTCACTTCCGAGGTGGAGGTAAAGAAATCAACTGAGCAGGGCCAC        7560
 P   L   D   L   K   V   T   S   E   V   E   V   K   K   S   T   E   Q   G   H         59
```

FIG. 1i

```
GCTGTTGTGGCAAACTTATGTTCCGGTGTCATCTTGATGAGACCTCACCCACCGTCCCTT    7620
 A  V  V  A  N  L  C  S  G  V  I  L  M  R  P  H  P  P  S  L      79

GTCGACGTTCTTCTGAAACCCGGACTTGACACAATACCCGGCATTCAACCAGGGCATGGG    7680
 V  D  V  L  L  K  P  G  L  D  T  I  P  G  I  Q  P  G  H  G      99

GCCGGGAATATGGGCGTGGACGGTTCTATTTGGGATTTTGAAACCGCACCCACAAAGGCA    7740
 A  G  N  M  G  V  D  G  S  I  W  D  F  E  T  A  P  T  K  A     119

GAACTCGAGTTATCCAAGCAAATAATCCAAGCATGTGAAGTTAGGCGCGGGGACGCCCCG    7800
 E  L  E  L  S  K  Q  I  I  Q  A  C  E  V  R  R  G  D  A  P     139

AACCTCCAACTCCCTTACAAGCTCTATCCTGTTAGGGGGGATCCTGAGCGGCATAAAGGC    7860
 N  L  Q  L  P  Y  K  L  Y  P  V  R  G  D  P  E  R  H  K  G     159

CGCCTTATCAATACCAGGTTTGGAGATTTACCTTACAAAACTCCTCAAGACACCAAGTCC    7920
 R  L  I  N  T  R  F  G  D  L  P  Y  K  T  P  Q  D  T  K  S     179

GCAATCCACGCGGCTTGTTGCCTGCACCCCAACGGGGCCCCCGTGTCTGATGGTAAATCC    7980
 A  I  H  A  A  C  L  H  P  N  G  A  P  V  S  D  G  K  S        199

ACACTAGGTACCACTCTTCAACATGGTTTCGAGCTTTATGTCCCTACTGTGCCCTATAGT    8040
 T  L  G  T  T  L  Q  H  G  F  E  L  Y  V  P  T  V  P  Y  S     219

GTCATGGAGTACCTTGATTCACGCCCTGACACCCCTTTTATGTGTACTAAACATGGCACT    8100
 V  M  E  Y  L  D  S  R  P  D  T  P  F  M  C  T  K  H  G  T     239

TCCAAGGCTGCTGCAGAGGACCTCCAAAAATACGACCTATCCACCCAAGGATTTGTCCTG    8160
 S  K  F  V  L  P  G  V  L  R  L  V  R  R  F  I  F  A  A  A     259

CCTGGGGTCCTACGCCTAGTACGCAGATTCATCTTTGGCCATATTGGTAAGGCGCCGCCA    8220
 E  D  L  Q  K  Y  D  L  S  T  Q  G  G  H  I  G  K  A  P  P     279

TTGTTCCTCCCATCAACCTATCCCGCCAAGAACTCTATGGCAGGGATCAATGGCCAGAGG    8280
 L  F  L  P  S  T  Y  P  A  K  N  S  M  A  G  I  N  G  Q  R     299

TTCCCAACAAAGGACGTTCAGAGCATACCTGAAATTGATGAAATGTGTGCCCGCGCTGTC    8340
 F  P  T  K  D  V  Q  S  I  P  E  I  D  E  M  C  A  R  A  V     319

AAGGAGAATTGGCAAACTGTGACACCTTGCACCCTCAAGAAACAGTACTGTTCCAAGCCC    8400
 K  E  N  W  Q  T  V  T  P  C  T  L  K  K  Q  Y  C  S  K  P     339

AAAACCAGGACCATCCTGGGCACCAACAACTTTATTGCCTTGGCTCACAGATCGGCGCTC    8460
 K  T  R  T  I  L  G  T  N  N  F  I  A  L  A  H  R  S  A  L     359

AGTGGTGTCACCCAGGCATTCATGAAGAAGGCTTGGAAGTCCCCAATTGCCTTGGGGAAA    8520
 S  G  V  T  Q  A  F  M  K  K  A  W  K  S  P  I  A  L  G  K     379
```

FIG. 1j

| | |
|---|---|
| AACAAATTCAAGGAGCTGCATTGCACTGTCGCCGGCAGGTGTCTTGAGGCCGACTTGGCC | 8580 |
|   N  K  F  K  E  L  H  C  T  V  A  G  R  C  L  E  A  D  L  A | 399 |
| TCCTGTGACCGCAGCACCCCCGCCATTGTAAGATGGTTTGTTGCCAACCTCCTGTATGAA | 8640 |
|   S  C  D  R  S  T  P  A  I  V  R  W  F  V  A  N  L  L  Y  E | 419 |
| CTTGCAGGATGTGAAGAGTACTTGCCTAGCTATGTGCTTAATTGCTGCCATGACCTCGTG | 8700 |
|   L  A  G  C  E  E  Y  L  P  S  Y  V  L  N  C  C  H  D  L  V | 439 |
| GCAACACAGGATGGTGCCTTCACAAAACGCGGTGGCCTGTCGTCCGGGGACCCCGTCACC | 8760 |
|   A  T  Q  D  G  A  F  T  K  R  G  G  L  S  S  G  D  P  V  T | 459 |
| AGTGTGTCCAACACCGTATATTCACTGGTAATTTATGCCCAGCACATGGTATTGTCGGCC | 8820 |
|   S  V  S  N  T  V  Y  S  L  V  I  Y  A  Q  H  M  V  L  S  A | 479 |
| TTGAAAATGGGTCATGAAATTGGTCTTAAGTTCCTCGAGGAACAGCTCAAGTTCGAGGAC | 8880 |
|   L  K  M  G  H  E  I  G  L  K  F  L  E  E  Q  L  K  F  E  D | 499 |
| CTCCTTGAAATTCAGCCTATGTTGGTATACTCTGATGATCTTGTCTTGTACGCTGAAAGA | 8940 |
|   L  L  E  I  Q  P  M  L  V  Y  S  D  D  L  V  L  Y  A  E  R | 519 |
|         C | |
| CCCACATTTCCCAATTACCACTGGTGGGTCGAGCACCTTGACCTGATGCTGGGTTTCAGA | 9000 |
|   P  T  F  P  N  Y  H  W  W  V  E  H  L  D  L  M  L  G  F  R | 539 |
| ACGGACCCAAAGAAAACCGTCATAACTGATAAACCCAGCTTCCTCGGCTGCAGAATTGAG | 9060 |
|   T  D  P  K  K  T  V  I  T  D  K  P  S  F  L  G  C  R  I  E | 559 |
| GCAGGGCGACAGCTAGTCCCCAATCGCGACCGCATCCTGGCTGCTCTTGCATATCACATG | 9120 |
|   A  G  R  Q  L  V  P  N  R  D  R  I  L  A  A  L  A  Y  H  M | 579 |
| AAGGCGCAGAACGCCTCAGAGTATTATGCGTCTGCTGCCGCAATCCTGATGGATTCATGT | 9180 |
|   K  A  Q  <u>N</u>  A  S  E  Y  Y  A  S  A  A  A  I  L  M  D  S  C | 599 |
| GCTTGCATTGACCATGACCCTGAGTGGTATGAGGACCTCATCTGCGGTATTGCCCGGTGC | 9240 |
|   A  C  I  D  H  D  P  E  W  Y  E  D  L  I  C  G  I  A  R  C | 619 |
| GCCCGCCAGGATGGTTATAGCTTCCCAGGTCCGGCATTTTTCATGTCCATGTGGGAGAAG | 9300 |
|   A  R  Q  D  G  Y  S  F  P  G  P  A  F  F  M  S  M  W  E  K | 639 |
| CTGAGAAGTCATAATGAAGGGAAGAAATTCCGCCACTGCGGCATCTGCGACGCCAAAGCC | 9360 |
|   L  R  S  H  N  E  G  K  K  F  R  H  C  G  I  C  D  A  K  A | 659 |
| GACTATGCGTCCGCCTGTGGGCTTGATTTGTGTTTGTTCCATTCGCACTTTCATCAACAC | 9420 |
|   D  Y  A  S  A  C  G  L  D  L  C  L  F  H  S  H  F  H  Q  H | 679 |

FIG. 1k

```
                          C
    TGCCCTGTCACTCTGAGCTGCGGTCACCATGCCGGTTCAAAGGAATGTTCGCAGTGTCAG    9480
     C  P  V  T  L  S  C  G  H  H  A  G  S  K  E  C  S  Q  C  Q     699

TCACCTGTTGGGGCTGGCAGATCCCCTCTTGATGCCGTGCTAAAACAAATTCCATACAAA    9540
     S  P  V  G  A  G  R  S  P  L  D  A  V  L  K  Q  I  P  Y  K     719

CCTCCTCGTACTGTCATCATGAAGGTGGGTAATAAAACAACGGCCCTCGATCCGGGGAGG    9600
     P  P  R  T  V  I  M  K  V  G  N  K  T  T  A  L  D  P  G  R     739

TACCAGTCCCGTCGAGGTCTCGTTGCAGTCAAGAGGGGTATTGCAGGCAATGAAGTTGAT    9660
     Y  Q  S  R  R  G  L  V  A  V  K  R  G  I  A  G  N  E  V  D     759

A
    CTTTCTGATGGGGACTACCAAGTGGTGCCTCTTTTGCCGACTTGCAAAGACATAAACATG    9720
     L  S  D  G  D  Y  Q  V  V  P  L  L  P  T  C  K  D  I  N  M     779

GTGAAGGTGGCTTGCAATGTACTACTCAGCAAGTTCATAGTAGGGCCACCAGGTTCCGGA    9780
     V  K  V  A  C  N  V  L  L  S  K  F  I  V  G  P  P  G  S  G     799

T
    AAGACCACCTGGCTACTGAGTCAAGTCCAGGACGATGATGTCATTTACACACCCACCCAT    9840
     K  T  T  W  L  L  S  Q  V  Q  D  D  D  V  I  Y  T  P  T  H     819
                                                  I

CAGACTATGTTTGATATAGTCAGTGCTCTCAAAGTTTGCAGGTATTCCATTCCAGGAGCC    9900
     Q  T  M  F  D  I  V  S  A  L  K  V  C  R  Y  S  I  P  G  A     839

TCAGGACTCCCTTTCCCACCACCTGCCAGGTCCGGGCCGTGGGTTAGGCTTATTGCCAGC    9960
     S  G  L  P  F  P  P  P  A  R  S  G  P  W  V  R  L  I  A  S     859

GGGCACGTCCCTGGCCGAGTATCATACCTCGATGAGGCTGGATATTGTAATCATCTGGAC   10020
     G  H  V  P  G  R  V  S  Y  L  D  E  A  G  Y  C  N  H  L  D     879

ATTCTTAGACTGCTTTCCAAAACACCCCTTGTGTGTTTGGGTGACCTTCAGCAACTTCAC   10080
     I  L  R  L  L  S  K  T  P  L  V  C  L  G  D  L  Q  Q  L  H     899

CCTGTCGGCTTTGATTCCTACTGTTATGTGTTCGATCAGATGCCTCAGAAGCAGCTGACC   10140
     P  V  G  F  D  S  Y  C  Y  V  F  D  Q  M  P  Q  K  Q  L  T     919

ACTATTTACAGATTTGGCCCTAACATCTGCGCACGCATCCAGCCTTGTTACAGGGAGAAA   10200
     T  I  Y  R  F  G  P  N  I  C  A  R  I  Q  P  C  Y  R  E  K     939

CTTGAATCTAAGGCTAGGAACACTAGGGTGGTTTTTACCACCCGGCCTGTGGCCTTTGGT   10260
     L  E  S  K  A  R  N  T  R  V  V  F  T  T  R  P  V  A  F  G     959

CAGGTGCTGACACCATACCATAAAGATCGCATCGGCTCTGCGATAACCATAGATTCATCC   10320
     Q  V  L  T  P  Y  H  K  D  R  I  G  S  A  I  T  I  D  S  S     979
```

FIG. 11

```
CAGGGGGCCACCTTTGATATTGTGACATTGCATCTACCATCGCCAAAGTCCCTAAATAAA      10380
 Q   G   A   T   F   D   I   V   T   L   H   L   P   S   P   K   S   L   N   K        999

TCCCGAGCACTTGTAGCCATCACTCGGGCAAGACACGGGTTGTTCATTTATGACCCTCAT      10440
 S   R   A   L   V   A   I   T   R   A   R   H   G   L   F   I   Y   D   P   H       1019

AACCAGCTCCAGGAGTTTTTCAACTTAACCCCTGAGCGCACTGATTGTAACCTTGTGTTC      10500
 N   Q   L   Q   E   F   F   N   L   T   P   E   R   T   D   C   N   L   V   F       1039

AGCCGTGGGGATGAGCTGGTAGTTCTGAATGCGGATAATGCAGTCACAACTGTAGCGAAG      10560
 S   R   G   D   E   L   V   V   L   N   A   D   N   A   V   T   T   V   A   K       1059

GCCCTTGAGACAGGTCCATCTCGATTTCGAGTATCAGACCCGAGGTGCAAGTCTCTCTTA      10620
 A   L   E   T   G   P   S   R   F   R   V   S   D   P   R   C   K   S   L   L       1079

GCCGCTTGTTCGGCCAGTCTGGAAGGGAGCTGTATGCCACTACCGCAAGTGGCACATAAC      10680
 A   A   C   S   A   S   L   E   G   S   C   M   P   L   P   Q   V   A   H   N       1099

CTGGGGTTTTACTTTTCCCCGGACAGTCCAACATTTGCACCTCTGCCAAAAGAGTTGGCG      10740
 L   G   F   Y   F   S   P   D   S   P   T   F   A   P   L   P   K   E   L   A       1119

CCACATTGGCCAGTGGTTACCCACCAGAATAATCGGGCGTGGCCTGATCGACTTGTCGCT      10800
 P   H   W   P   V   V   T   H   Q   N   N   R   A   W   P   D   R   L   V   A       1139

AGTATGCGCCCAATTGATGCCCGCTACAGCAAGCCAATGGTCGGTGCAGGGTATGTGGTC      10860
 S   M   R   P   I   D   A   R   Y   S   K   P   M   V   G   A   G   Y   V   V       1159

GGGCCGTCCACCTTTCTTGGTACTCCTGGTGTGGTGTCATACTATCTCACACTATACATC      10920
 G   P   S   T   F   L   G   T   P   G   V   V   S   Y   Y   L   T   L   Y   I       1179

AGGGGTGAGCCCCAGGCCTTGCCAGAAACACTCGTTTCAACAGGGCGTATAGCCACAGAT      10980
 R   G   E   P   Q   A   L   P   E   T   L   V   S   T   G   R   I   A   T   D       1199

TGTCGGGAGTATCTCGACGCGGCTGAGGAAGAGGCAGCAAAAGAACTCCCCCACGCATTC      11040
 C   R   E   Y   L   D   A   A   E   E   E   A   A   K   E   L   P   H   A   F       1219

ATTGGCGATGTCAAAGGTACCACGGTTGGGGGGTGTCATCACATTACATCAAAATACCTA      11100
 I   G   D   V   K   G   T   T   V   G   G   C   H   H   I   T   S   K   Y   L       1239

CCTAGGTCCCTGCCTAAGGACTCTGTTGCCGTAGTTGGAGTAAGTTCGCCCGGCAGGGCT      11160
 P   R   S   L   P   K   D   S   V   A   V   V   G   V   S   S   P   G   R   A       1259

GCTAAAGCCGTGTGCACTCTCACCGATGTGTACCTCCCCGAACTCCGGCCATATCTGCAA      11220
 A   K   A   V   C   T   L   T   D   V   Y   L   P   E   L   R   P   Y   L   Q       1279

CCTGAGACGGCATCAAAATGCTGGAAACTCAAATTAGACTTCAGGGACGTCCGACTAATG      11280
 P   E   T   A   S   K   C   W   K   L   K   L   D   F   R   D   V   R   L   M       1299
```

FIG. 1m

```
GTCTGGAAAGGAGCCACCGCCTATTTCCAGTTGGAAGGGCTTACATGGTCGGCGCTGCCC  11340
 V  W  K  G  A  T  A  Y  F  Q  L  E  G  L  T  W  S  A  L  P   1319
             C
GACTATGCCAGGTTTATTCAGCTGCCCAAGGATGCCGTTGTATACATTGATCCGTGTATA  11400
 D  Y  A  R  F  I  Q  L  P  K  D  A  V  V  Y  I  D  P  C  I   1339

GGACCGGCAACAGCCAACCGTAAGGTCGTGCGAACCACAGACTGGCGGGCCGACCTGGCA  11460
 G  P  A  T  A  N  R  K  V  V  R  T  T  D  W  R  A  D  L  A   1359

GTGACACCGTATGATTACGGTGCCCAGAACATTTTGACAACAGCCTGGTTCGAGGACCTC  11520
 V  T  P  Y  D  Y  G  A  Q  N  I  L  T  T  A  W  F  E  D  L   1379

GGGCCGCAGTGGAAGATTTTGGGGTTGCAGCCCTTTAGGCGAGCATTTGGCTTTGAAAAC  11580
 G  P  Q  W  K  I  L  G  L  Q  P  F  R  R  A  F  G  F  E  N   1399

ACTGAGGATTGGGCAATCCTTGCACGCCGTATGAATGACGGCAAGGACTACACTGACTAT  11640
 T  E  D  W  A  I  L  A  R  R  M  N  D  G  K  D  Y  T  D  Y   1419

AACTGGAACTGTGTTCGAGAACGCCCACACGCCATCTACGGGCGTGCTCGTGACCATACG  11700
 N  W  N  C  V  R  E  R  P  H  A  I  Y  G  R  A  R  D  H  T   1439

TATCATTTTGCCCCTGGCACAGAATTGCAGGTAGAGCTAGGTAAACCCCGGCTGCCGCCT  11760
 Y  H  F  A  P  G  T  E  L  Q  V  E  L  G  K  P  R  L  P  P   1459

GGGCAAGTGCCGTGAATTCGGGGTGATGCAATGGGGTCACTGTGGAGTAAAATCAGCCAG  11820
 G  Q  V  P  -                                                1463
     ORF2         M  Q  W  G  H  C  G  V  K  S  A  S          12
                                              T
CTGTTCGTGGACGCCTTCACTGAGTTCCTTGTTAGTGTGGTTGATATTGCCATTTTCCTT  11880
 C  S  W  T  P  S  L  S  S  L  L  V  W  L  I  L  P  F  S  L   32
                   S
GCCATACTGTTTGGGTTCACCGTCGCAGGATGGTTACTGGTCTTTCTTCTCAGAGTGGTT  11940
 P  Y  C  L  G  S  P  S  Q  D  G  Y  W  S  F  F  S  E  W  F   52

TGCTCCGCGCTTCTCCGTTCGCGCTCTGCCATTCACTCTCCCGAACTATCGAAGGTCCTA  12000
 A  P  R  F  S  V  R  A  L  P  F  T  L  P  N  Y  R  R  S  Y   72

TGAAGGCTTGTTGCCCAACTGCAGACCGGATGTCCCACAATTTGCAGTCAAGCACCCATT  12060
 E  G  L  L  P  N  C  R  P  D  V  P  Q  F  A  V  K  H  P  L   92
   C                                           G
GGGTATGTTTTGGCACATGCGAGTTTCCCACTTGATTGATGAGATGGTCTCTCGTCGCAT  12120
 G  M  F  W  H  M  R  V  S  H  L  I  D  E  M  V  S  R  R  I   112
                                     V
```

FIG. 1n

```
TTACCAGACCATGGAACATTCAGGTCAAGCGGCCTGGAAGCAGGTGGTTGGTGAGGCCAC   12180
  Y  Q  T  M  E  H  S  G  Q  A  A  W  K  Q  V  V  G  E  A  T     132

TCTCACGAAGCTGTCAGGGCTCGATATAGTTACTCATTTCCAACACCTGGCCGCAGTGGA   12240
  L  T  K  L  S  G  L  D  I  V  T  H  F  Q  H  L  A  A  V  E     152

GGCGGATTCTTGCCGCTTTCTCAGCTCACGACTCGTGATGCTAAAAAATCTTGCCGTTGG   12300
  A  D  S  C  R  F  L  S  S  R  L  V  M  L  K  N  L  A  V  G     172

CAATGTGAGCCTACAGTACAACACCACGTTGGACCGCGTTGAGCTCATCTTCCCCACGCC   12360
  N  V  S  L  Q  Y  N  T  T  L  D  R  V  E  L  I  F  P  T  P     192

AGGTACGAGGCCCAAGTTGACCGATTTCAGACAATGGCTCATCAGTGTGCACGCTTCCAT   12420
  G  T  R  P  K  L  T  D  F  R  Q  W  L  I  S  V  H  A  S  I     212
                                         ORF3  M  A  H  Q  C  A  R  F  H     9

TTTTTCCTCTGTGGCTTCATCTGTTACCTTGTTCATAGTGCTTTGGCTTCGAATTCCAGC   12480
  F  S  S  V  A  S  S  V  T  L  F  I  V  L  W  R  I  P  A          232
  F  F  L  C  G  F  I  C  Y  L  V  H  S  A  L  A  S  N  S  S      29

TCTACGCTATGTTTTTGGTTTCCATTGGCCCACGGCAACACATCATTCGAGCTGACCATC   12540
  L  R  Y  V  F  G  F  H  W  P  T  H  H  S  S  -                  249
  S  T  L  C  F  W  F  P  L  A  H  G  N  T  S  F  E  L  T  I      49

AACTACACCATATGCATGCCCTGTTCTACCAGTCAAGCGGCTCGCCAAAGGCTCGAGCCC   12600
  N  Y  T  I  C  M  P  C  S  T  S  Q  A  A  R  Q  R  L  E  P      69

GGTCGTAACATGTGGTGCAAAATAGGGCATGACAGGTGTGAGGAGCGTGACCATGATGAG   12660
  G  R  N  M  W  C  K  I  G  H  D  R  C  E  E  R  D  H  D  E      89

TTGTTAATGTCCATCCCGTCCGGGTACGACAACCTCAAACTTGAGGGTTATTATGCTTGG   12720
  L  L  M  S  I  P  S  G  Y  D  N  L  K  L  E  G  Y  Y  A  W     109

CTGGCTTTTTTGTCCTTTTCCTACGCGGCCCAATTCCATCCGGAGTTGTTCGGGATAGGG   12780
  L  A  F  L  S  F  S  Y  A  A  Q  F  H  P  E  L  F  G  I  G     129

AATGTGTCGCGCGTCTTCGTGGACAAGCGACACCAGTTCATTTGTGCCGAGCATGATGGA   12840
  N  V  S  R  V  F  V  D  K  R  H  Q  F  I  C  A  E  H  D  G     149

CACAATTCAACCGTATCTACCGGACACAACATCTCCGCATTATATGCGGCATATTACCAC   12900
  H  N  S  T  V  S  T  G  H  N  I  S  A  L  Y  A  A  Y  Y  H     169

CACCAAATAGACGGGGGCAATTGGTTCCATTTGGAATGGCTGCGGCCACTCTTTTCTTCC   12960
  H  Q  I  D  G  G  N  W  F  H  L  E  W  L  R  P  L  F  S  S     189
                        ORF4  M  A  A  A  T  L  F  F                 8
```

FIG. 1o

```
TGGCTGGTGCTCAACATATCATGGTTTCTGAGGCGTTCGCCTGTAAGCCCTGTTTCTCGA    13020
 W  L  V  L  N  I  S  W  F  L  R  R  S  P  V  S  P  V  S  R     209
   L  A  G  A  Q  H  I  M  V  S  E  A  F  A  C  K  P  C  F  S    28

CGCATCTATCAGATATTGAGACCAACACGACCGCGGCTGCCGGTTTCATGGTCCTTCAGG    13080
 R  I  Y  Q  I  L  R  P  T  R  P  R  L  P  V  S  W  S  F  R     229
   T  H  L  S  D  I  E  T  N  T  T  A  A  A  G  F  M  V  L  Q    48

ACATCAATTGTTTCCGACCTCACGGGGTCTCAGCAGCGCAAGAGAAAATTTCCTTCGGAA    13140
 T  S  I  V  S  D  L  T  G  S  Q  Q  R  K  R  K  F  P  S  E     249
   D  I  N  C  F  R  P  H  G  V  S  A  A  Q  E  K  I  S  F  G    68

AGTCGTCCCAATGTCGTGAAGCCGTCGGTACTCCCCAGTACATCACGATAACGGCTAACG    13200
 S  R  P  N  V  V  K  P  S  V  L  P  S  T  S  R  -              265
   K  S  S  Q  C  R  E  A  V  G  T  P  Q  Y  I  T  I  T  A  N    88

TGACCGACGAATCATACTTGTACAACGCGGACCTGCTGATGCTTTCTGCGTGCCTTTTCT    13260
 V  T  D  E  S  Y  L  Y  N  A  D  L  L  M  L  S  A  C  L  F     108

ACGCCTCAGAAATGAGCGAGAAAGGCTTCAAAGTCATCTTTGGGAATGTCTCTGGCGTTG    13320
 Y  A  S  E  M  S  E  K  G  F  K  V  I  F  G  N  V  S  G  V     128

TTTCTGCTTGTGTCAATTTCACAGATTATGTGGCCCATGTGACCCAACATACCCAGCAGC    13380
 V  S  A  C  V  N  F  T  D  Y  V  A  H  V  T  Q  H  T  Q  Q     148

ATCATCTGGTAATTGATCACATTCGGTTGCTGCATTTCCTGACACCATCTGCAATGAGGT    13440
 H  H  L  V  I  D  H  I  R  L  L  H  F  L  T  P  S  A  M  R     168

GGGCTACAACCATTGCTTGTTTGTTCGCCATTCTCTTGGCAATATGAGATGTTCTCACAA    13500
 W  A  T  T  I  A  C  L  F  A  I  L  L  A  I  -                 183
                                         ORF5    M  R  C  S  H  K   6

ATTGGGGCGTTTCTTGACTCCGCACTCTTGCTTCTGGTGGCTTTTTTTGCTGTGTACCGG    13560
   L  G  R  F  L  T  P  H  S  C  F  W  W  L  F  L  L  C  T  G    26

CTTGTCCTGGTCCTTTGCCGATGGCAACGGCGACAGCTCGACATACCAATACATATATAA    13620
   L  S  W  S  F  A  D  G  N  G  D  S  S  T  Y  Q  Y  I  Y  N    46

CTTGACGATATGCGAGCTGAATGGGACCGACTGGTTGTCCAGCCATTTTGGTTGGGCAGT    13680
   L  T  I  C  E  L  N  G  T  D  W  L  S  S  H  F  G  W  A  V    66

CGAGACCTTTGTGCTTTACCCGGTTGCCACTCATATCCTCTCACTGGGTTTTCTCACAAC    13740
   E  T  F  V  L  Y  P  V  A  T  H  I  L  S  L  G  F  L  T  T    86

AAGCCATTTTTTTGACGCGCTCGGTCTCGGCGCTGTATCCACTGCAGGATTTGTTGGCGG    13800
   S  H  F  F  D  A  L  G  L  G  A  V  S  T  A  G  F  V  G      106
```

FIG. 1p

```
GCGGTACGTACTCTGCAGCGTCTACGGCGCTTGTGCTTTCGCAGCGTTCGTATGTTTTGT   13860
  R   Y  V  L  C  S  V  Y  G  A  C  A  F  A  A  F  V  C  F  V    126

CATCCGTGCTGCTAAAAATTGCATGGCCTGCCGCTATGCCCGTACCCGGTTTACCAACTT   13920
  I  R  A  A  K  N  C  M  A  C  R  Y  A  R  T  R  F  T  N  F    146

CATTGTGGACGACCGGGGGAGAGTTCATCGATGGAAGTCTCCAATAGTGGTAGAAAAATT   13980
  I  V  D  D  R  G  R  V  H  R  W  K  S  P  I  V  V  E  K  L    166

GGGCAAAGCCGAAGTCGATGGCAACCTCGTCACCATCAAACATGTCGTCCTCGAAGGGGT   14040
  G  K  A  E  V  D  G  N  L  V  T  I  K  H  V  V  L  E  G  V    186

TAAAGCTCAACCCTTGACGAGGACTTCGGCTGAGCAATGGGAGGCCTAGACGATTTTTGC   14100
  K  A  Q  P  L  T  R  T  S  A  E  Q  W  E  A  -                201
                                   ORF6    M  G  G  L  D  D  F  C    8

AACGATCCTATCGCCGCACAAAAGCTCGTGCTAGCCTTTAGCATCACATACACACCTATA   14160
  N  D  P  I  A  A  Q  K  L  V  L  A  F  S  I  T  Y  T  P  I    28

ATGATATACGCCCTTAAGGTGTCACGCGGCCGACTCCTGGGGCTGTTGCACATCCTAATA   14220
  M  I  Y  A  L  K  V  S  R  G  R  L  L  G  L  L  H  I  L  I    48

TTTCTGAACTGTTCCTTTACATTCGGATACATGACATATGTGCATTTTCAATCCACCAAC   14280
  F  L  N  C  S  F  T  F  G  Y  M  T  Y  V  H  F  Q  S  T  N    68

CGTGTCGCACTTACCCTGGGGGCTGTTGTCGCCCTTCTGTGGGGTGTTTACAGCTTCACA   14340
  R  V  A  L  T  L  G  A  V  V  A  L  L  W  G  V  Y  S  F  T    88

GAGTCATGGAAGTTTATCACTTCCAGATGCAGATTGTGTTGCCTTGGCCGGCGATACATT   14400
  E  S  W  K  F  I  T  S  R  C  R  L  C  C  L  G  R  R  Y  I    108

CTGGCCCCTGCCCATCACGTAGAAAGTGCTGCAGGTCTCCATTCAATCTCAGCGTCTGGT   14460
  L  A  P  A  H  H  V  E  S  A  A  G  L  H  S  I  S  A  S  G    128

AACCGAGCATACGCTGTGAGAAAGCCCGGACTAACATCAGTGAACGGCACTCTAGTACCA   14520
  N  R  A  Y  A  V  R  K  P  G  L  T  S  V  N  G  T  L  V  P    148

GGACTTCGGAGCCTCGTGCTGGGCGGCAAACGAGCTGTTAAACGAGGAGTGGTTAACCTC   14580
  G  L  R  S  L  V  L  G  G  K  R  A  V  K  R  G  V  V  N  L    168

GTCAAGTATGGCCGGTAAAAACCAGAGCCAGAAGAAAAAGAAAAGTACAGCTCCGATGGG   14640
  V  K  Y  G  R  -                                              173
ORF7  M  A  G  K  N  Q  S  Q  K  K  K  K  S  T  A  P  M  G      18

GAATGGCCAGCCAGTCAATCAACTGTGCCAGTTGCTGGGTGCAATGATAAAGTCCCAGCG   14700
  N  G  Q  P  V  N  Q  L  C  Q  L  L  G  A  M  I  K  S  Q  R    38
```

FIG. 1q

```
                                  T
CCAGCAACCTAGGGGAGGACAGGCCAAAAAGAAAAAGCCTGAGAAGCCACATTTTCCCCT    14760
  Q  Q  P  R  G  G  Q  A  K  K  K  P  E  K  P  H  F  P  L        58

GGCTGCTGAAGATGACATCCGGCACCACCTCACCCAGACTGAACGCTCCCTCTGCTTGCA    14820
  A  A  E  D  D  I  R  H  H  L  T  Q  T  E  R  S  L  C  L  Q     78

A
ATCGATCCAGACGGCTTTCAATCAAGGCGCAGGAACTGCGTCGCTTTCATCCAGCGGGAA    14880
  S  I  Q  T  A  F  N  Q  G  A  G  T  A  S  L  S  S  S  G  K     98

GGTCAGTTTTCAGGTTGAGTTTATGCTGCCGGTTGCTCATACAGTGCGCCTGATTCGCGT    14940
  V  S  F  Q  V  E  F  M  L  P  V  A  H  T  V  R  L  I  R  V    118

GACTTCTACATCCGCCAGTCAGGGTGCAAGTTAATTTGACAGTCAGGTGAATGGCCGCGA    15000
  T  S  T  S  A  S  Q  G  A  S  -                               128

TGGCGTGTGGCCTCTGAGTCACCTATTCAATTAGGGCGATCACATGGGGGTCATACTTAA    15060

TTCAGGCAGGAACCATGTGACCGAAATTAAAAAAAAAAAAAAAAAAAAA              15088
```

CAUSATIVE AGENT OF THE MYSTERY SWINE DISEASE, VACCINE COMPOSITIONS AND DIAGNOSTIC KITS

RELATED APPLICATIONS

The present application is a continuation application of U.S. application Ser. No. 10/891,444, filed Jul. 14, 2004, which a continuation application of U.S. application Ser. No. 10/226,065, now U.S. Pat. No. 6,806,086, filed Aug. 21, 2002, which is a divisional of U.S. application Ser. No. 09/565,864, filed May 5, 2000, now U.S. Pat. No. 6,455,245, issued Sep. 24, 2002, which is a divisional of U.S. application Ser. No. 08/757,863, filed Nov. 13, 1996, now U.S. Pat. No. 6,197,310, issued Mar. 6, 2001, which itself is a divisional of U.S. patent application Ser. No. 08/157,005, filed Nov. 26, 1993, now U.S. Pat. No. 5,620,691, which is a National Stage under 35 U.S.C. §371 of International Patent Application PCT/NL92/00096, filed Jun. 5, 1992, the contents of all of which are incorporated by this reference.

TECHNICAL FIELD

1. Field of the Invention

The invention relates to the isolation, characterization and utilization of the causative agent of the Mystery Swine Disease (MSD). The invention utilizes the discovery of the agent causing the disease and the determination of its genome organization, the genomic nucleotide sequence and the proteins encoded by the genome, for providing protection against and diagnosis of infections, in particular, protection against and diagnosis of MSD infections, and for providing vaccine compositions and diagnostic kits, either for use with MSD or with other pathogen-caused diseases.

2. Background

In the winter and early spring of 1991, the Dutch pig industry was struck by a sudden outbreak of a new disease among breeding sows. Most sows showed anorexia, some aborted late in gestation (around day 110), showed stillbirths or gave birth to mummified fetuses and some had fever. Occasionally, sows with bluish ears were found, therefore, the disease was commonly named "Abortus Blauw". The disease in the sows was often accompanied by respiratory distress and death of their young piglets and often by respiratory disease and growth retardation of older piglets and fattening pigs.

The cause of this epizootic was not known, but the symptoms resembled those of a similar disease occurring in Germany since late 1990, and resembled those of the so-called "Mystery Swine Disease" as seen since 1987 in the mid-west of the United States of America and in Canada (Hill, 1990). Various other names have been used for the disease; in Germany it is known as "Seuchenhafter Spätabort der Schweine" and in North America it is also known as "Mystery Pig Disease", "Mysterious Reproductive Syndrome", and "Swine Infertility and Respiratory Syndrome". In North America, Loula (1990) described the general clinical signs as:

1) off feed, sick animals of all ages;
2) abortions, stillbirths, weak pigs, mummies;
3) post-farrowing respiratory problems; and
4) breeding problems.

No causative agent has as yet been identified, but encephalomyocarditis virus ("EMCV"), porcine parvo virus ("PPV"), pseudorabies virus ("PRV"), swine influenza virus ("SIV"), bovine viral diarrhea virus ("BVDV"), hog cholera virus ("HCV"), porcine entero viruses ("PEV"), an influenza-like virus, chlamidiae, leptospirae, have all been named as a possible cause (Loula, 1990; Mengeling and Lager, 1990; among others).

SUMMARY OF THE INVENTION

The invention provides a composition of matter comprising isolated Lelystad Agent which is the causative agent of Mystery Swine Disease, the Lelystad Agent essentially corresponding to the isolate Lelystad Agent (CDI-NL-2.91) deposited Jun. 5, 1991 with the Institut Pasteur, Collection Nationale de Cultures De Microorganismes (C.N.C.M.) 25, rue du Docteur Roux, 75724—Paris Cedex 15, France, deposit number I-1102. The words "essentially corresponding" refer to variations that occur in nature and to artificial variations of Lelystad Agent, particularly those which still allow detection by techniques like hybridization, PCR and ELISA, using Lelystad Agent-specific materials, such as Lelystad Agent-specific DNA or antibodies.

The composition of matter may comprise live, killed, or attenuated isolated Lelystad Agent; a recombinant vector derived from Lelystad Agent; an isolated part or component of Lelystad Agent; isolated or synthetic protein (poly)peptide, or nucleic acid derived from Lelystad Agent; recombinant nucleic acid which comprises a nucleotide sequence derived from the genome of Lelystad Agent; a (poly)peptide having an amino acid sequence derived from a protein of Lelystad Agent, the (poly)peptide being produced by a cell capable of producing it due to genetic engineering with appropriate recombinant DNA; an isolated or synthetic antibody which specifically recognizes a part or component of Lelystad Agent; or a recombinant vector which contains nucleic acid comprising a nucleotide sequence coding for a protein or antigenic peptide derived from Lelystad Agent.

On the DNA level, the invention specifically provides a recombinant nucleic acid, more specifically recombinant DNA, which comprises a Lelystad Agent-specific nucleotide sequence shown in FIG. 1 (SEQ ID NO:1) which includes FIGS. 1a through 1q. Preferably, the Lelystad Agent-specific nucleotide sequence is selected from any one of the ORFs (Open Reading Frames) shown in FIG. 1 (SEQ ID NO:1).

On the peptide/protein level, the invention specifically provides a peptide comprising a Lelystad Agent-specific amino acid sequence shown in FIG. 1 (SEQ ID NO:1).

The invention further provides a vaccine composition for vaccinating animals, in particular mammals, more in particular pigs or swine, to protect them against Mystery Swine Disease, comprising Lelystad Agent, either live, killed, or attenuated; or a recombinant vector which contains nucleic acid comprising a nucleotide sequence coding for a protein or antigenic peptide derived from Lelystad Agent; an antigenic part or component of Lelystad Agent; a protein or antigenic polypeptide derived from, or a peptide mimicking an antigenic component of, Lelystad Agent; and a suitable carrier or adjuvant.

The invention also provides a vaccine composition for vaccinating animals, in particular mammals, more in particular pigs or swine, to protect them against a disease caused by a pathogen, comprising a recombinant vector derived from Lelystad Agent, the nucleic acid of the recombinant vector comprising a nucleotide sequence coding for a protein or antigenic peptide derived from the pathogen, and a suitable carrier or adjuvant.

The invention further provides a diagnostic kit for detecting nucleic acid from Lelystad Agent in a sample, in particular a biological sample such as blood or blood serum, sputum, saliva, or tissue, derived from an animal, in particular a mammal, more in particular a pig or swine, comprising a nucleic acid probe or primer which comprises a nucleotide sequence derived from the genome of Lelystad Agent, and suitable detection means of a nucleic acid detection assay.

The invention also provides a diagnostic kit for detecting antigen from Lelystad Agent in a sample, in particular a biological sample such as blood or blood serum, sputum, saliva, or tissue, derived from an animal, in particular a mammal, more in particular a pig or swine, comprising an antibody which specifically recognizes a part or component of Lelystad Agent, and suitable detection means of an antigen detection assay.

The invention also provides a diagnostic kit for detecting an antibody which specifically recognizes Lelystad Agent in a sample, in particular a biological sample such as blood or blood serum, sputum, saliva, or tissue, derived from an animal, in particular a mammal, more in particular a pig or swine, comprising Lelystad Agent; an antigenic part or component of Lelystad Agent; a protein or antigenic polypeptide derived from Lelystad Agent; or a peptide mimicking an antigenic component of Lelystad Agent; and suitable detection means of an antibody detection assay.

The invention also relates to a process for diagnosing whether an animal, in particular a mammal, more in particular a pig or swine, is contaminated with the causative agent of Mystery Swine Disease, comprising preparing a sample, in particular a biological sample such as blood or blood serum, sputum, saliva, or tissue, derived from the animal, and examining whether it contains Lelystad Agent nucleic acid, Lelystad Agent antigen, or antibody specifically recognizing Lelystad Agent, the Lelystad Agent being the causative agent of Mystery Swine Disease and essentially corresponding to the isolate Lelystad Agent (CDI-NL-2.91) deposited 5 Jun. 1991 with the Institut Pasteur, Paris, France, deposit number I-1102.

DETAILED DESCRIPTION OF THE INVENTION

The invention is a result of combined efforts of the Central Veterinary Institute (CVI) and the Regional Animal Health Services (RAHS) in the Netherlands in trying to find the cause of the new disease MSD. Farms with pigs affected by the new disease were visited by field veterinarians of the RAHS. Sick pigs, specimens of sick pigs, and sow sera taken at the time of the acute and convalescent phase of the disease were sent for virus isolation to the RAHS and the CVI. Paired sera of affected sows were tested for antibodies against ten known pig-viruses. Three different viruses, encephalomyocarditis virus, porcine entero virus type 2, porcine entero virus type 7, and an unknown agent, Lelystad Agent (LA), were isolated. Sows which had reportedly been struck with the disease mainly seroconverted to LA, and rarely to any of the other virus isolates or the known viral pathogens. In order to reproduce MSD experimentally, eight pregnant sows were inoculated intranasally with LA at day 84 of gestation. One sow gave birth to seven dead and four live but very weak piglets at day 109 of gestation; the four live piglets died one day after birth. Another sow gave birth at day 116 to three mummified fetuses, six dead piglets and three live piglets; two of the live piglets died within one day. A third sow gave birth at day 117 to two mummified fetuses, eight dead and seven live piglets. The other sows farrowed around day 115 and had less severe reproductive losses. The mean number of live piglets from all eight sows at birth was 7.3 and the mean number of dead piglets at birth was 4.6. Antibodies directed against LA were detected in 10 out of 42 serum samples collected before the pigs had sucked. LA was isolated from three piglets that died shortly after birth. These results justify the conclusion that LA is the causal agent of mystery swine disease.

LA grows with a cytopathic affect in pig lung macrophages and can be identified by staining in an immuno-peroxidase-monolayer assay (IPMA) with post-infection sera of pigs c829 and b 822, or with any of the other post-infection sera of the SPF pigs listed in table 5. Antibodies to LA can be identified by indirect staining procedures in IPMA. LA did not grow in any other cell system tested. LA was not neutralized by homologous sera, or by sera directed against a set of known viruses (Table 3). LA did not haemagglutinate with the red blood cells tested. LA is smaller then 200 nm since it passes through a filter with pores of this size. LA is sensitive to chloroform. The above results show that Lelystad Agent is not yet identified as belonging to a certain virus group or other microbiological species. It has been deposited 5 Jun. 1991 under number I-1102 at Institute Pasteur, France.

The genome organization, nucleotide sequences, and polypeptides derived therefrom, of LA have now been found. These data together with those of others (see below) justify classification of LA (hereafter also called Lelystad Virus or LV) as a member of a new virus family, the Arteriviridae. As prototype virus of this new family we propose Equine Arteritis Virus (EAV), the first member of the new family of which data regarding the replication strategy of the genome and genome organization became available (de Vries et al., 1990, and references therein). On the basis of a comparison of our sequence data with those available for Lactate Dehydrogenase-Elevating Virus (LDV; Godeny et al., 1990), we propose that LDV is also a member of the Arteriviridae.

Given the genome organization and translation strategy of Arteriviridae, it seems appropriate to place this new virus family into the superfamily of coronaviruses (Snijder et al., 1990a).

Arteriviruses have in common that their primary target cells in respective hosts are macrophages. Replication of LDV has been shown to be restricted to macrophages in its host, the mouse; whereas this strict propensity for macrophages has not been resolved yet for EAV and LV.

Arteriviruses are spherical enveloped particles having a diameter of 45-60 nm and containing an icosahedral nucleocapsid (Brinton-Darnell and Plagemann, 1975; Horzinck et al., 1971; Hyllseth, 1973).

The genome of Arteriviridae consists of a positive stranded polyadenylated RNA molecule with a size of about 12-13 kilobases (kb) (Brinton-Darnell and Plagemann, 1975; van der Zeijst et al., 1975). EAV replicates via a 3' nested set of six subgenomic mRNAs, ranging in size from 0.8 to 3.6 kh, which are composed of a leader sequence, derived from the 5' end of the genomic RNA, which is joined to the 3' terminal body sequences (de Vries et al., 1990).

Here we show that the genome organization and replication strategy of LV is similar to that of EAV, coronaviruses and toroviruses, whereas the genome sizes of the latter viruses are completely different from those of LV and EAV.

The genome of LV consists of a genomic RNA molecule of about 14.5 to 15.5 kb in length (estimated on a neutral agarose gel), which replicates via a 3' nested set of subgenomic RNAs. The subgenomic RNAs consist of a leader sequence, the length of which is yet unknown, which is derived from the 5' end of the genomic RNA and which is fused to the body sequences derived from the 3' end of the genomic RNA (FIG. 2).

The nucleotide sequence of the genomic RNA of LV was determined from overlapping cDNA clones. A consecutive sequence of 15,088 bp was obtained covering nearly the complete genome of LV (FIG. 1, SEQ ID NO:1). In this sequence 8 open reading frames (ORFs) were identified: ORF 1A, ORF 1B, and ORFs 2 to 7.

ORF 1A and ORF 1B are predicted to encode the viral replicase or polymerase (SEQ ID NO:2 and SEQ ID NO:3), whereas ORFs 2 to 6 are predicted to encode structural viral membrane (envelope) associated proteins (SEQ ID NOS:4-8). ORF 7 is predicted to encode the structural viral nucleocapsid protein (SEQ ID NO:9).

Because the products of ORF 6 and ORF 7 of LV (SEQ ID NO:8 and SEQ ID NO:9) show a significant similarity with VpX and Vp1 of LDV, respectively, it is predicted that the sequences of ORFs 6 and 7 will also be highly conserved among antigenic variants of LV.

The complete nucleotide sequence of FIG. 1 (SEQ ID NO:1) and all the sequences and protein products encoded by ORFs 1 to 7 (SEQ ID NOS:1-9) and possible other ORFs located in the sequence of FIG. 1 (SEQ ID NO:1) are especially suited for vaccine development, in whatever sense, and for the development of diagnostic tools, in whatever sense. All possible modes are well known to persons skilled in the art.

Since it is now possible to unambiguously identify LA, the causal agent of MSD, it can now be tested whether pigs are infected with LA or not. Such diagnostic tests have, until now, been unavailable.

The test can be performed by virus isolation in macrophages, or other cell culture systems in which LA might grow, and staining the infected cultures with antibodies directed against LA (such as post-infection sera c 829 or b 822), but it is also feasible to develop and employ other types of diagnostic tests.

For instance, it is possible to use direct or indirect immunohistological staining techniques, i.e., with antibodies directed to LA that are labeled with fluorescent compounds such as isothiocyanate, or labeled with enzymes such as horseradish peroxidase. These techniques can be used to detect LA antigen in tissue sections or other samples from pigs suspected to have MSD. The antibodies needed for these tests can be c 829 or b 822 or other polyclonal antibodies directed against LA, but monoclonal antibodies directed against LA can also be used.

Furthermore, since the nature and organization of the genome of LA and the nucleotide sequence of this genome have been determined, LA-specific nucleotide sequences can be identified and used to develop oligonucleotide sequences that can be used as probes or primers in diagnostic techniques such as hybridization, polymerase chain reaction, or any other techniques that are developed to specifically detect nucleotide acid sequences.

It is also possible to test for antibodies directed against LA. Table 5 shows that experimentally infected pigs rapidly develop antibodies against LA, and table 4 shows that pigs in the field also have strong antibody responses against LA. Thus, it can now also be determined whether pigs have been infected with LA in the past. Such testing is of utmost importance in determining whether pigs or pig herds or pig populations or pigs in whole regions or countries are free of LA. The test can be done by using the IPMA as described, but it is also feasible to develop and employ other types of diagnostic tests for the detection of antibodies directed against LA.

LA-specific proteins, polypeptides, and peptides, or peptide sequences mimicking antigenic components of LA, can be used in such tests. Such proteins can be derived from the LA itself, but it is also possible to make such proteins by recombinant DNA or peptide synthesis techniques. These tests can use specific polyclonal and/or monoclonal antibodies directed against LA or specific components of LA, and/or use cell systems infected with LA or cell systems expressing LA antigen. The antibodies can be used, for example, as a means for immobilizing the LA antigen (a solid surface is coated with the antibody whereafter the LA antigen is bound by the antibody) which leads to a higher specificity of the test, or can be used in a competitive assay (labeled antibody and unknown antibody in the sample compete for available LA antigen).

Furthermore, the above described diagnostic possibilities can be applied to test whether other animals, such as mammals, birds, insects or fish, or plants, or other living creatures, can be, or are, or have been infected with LA or related agents.

Since LA has now been identified as the causal agent of MSD, it is possible to make a vaccine to protect pigs against this disease. Such a vaccine can simply be made by growing LA in pig lung macrophage cultures, or in other cell systems in which LA grows. LA can then be purified or not, and killed by established techniques, such as inactivation with formaline or ultra-violet light. The inactivated LA can then be combined with adjuvantia, such as Freund's adjuvans or aluminum hydroxide or others, and this composition can then be injected in pigs.

Dead vaccines can also be made with LA protein preparations derived from LA infected cultures, or derived from cell systems expressing specifically LA protein through DNA recombinant techniques. Such subunits of LA would then be treated as above, and this would result in a subunit vaccine.

Vaccines using even smaller components of LA, such as polypeptides, peptides, or peptides mimicking antigenic components of LA, are also feasible for use as dead vaccine.

Dead vaccines against MSD can also be made by recombinant DNA techniques through which the genome of LA, or parts thereof, is incorporated in vector systems such as vaccinia virus, herpesvirus, pseudorabies virus, adeno virus, baculo virus or other suitable vector systems that can so express LA antigen in appropriate cells systems. LA antigen from these systems can then be used to develop a vaccine as above, and pigs, vaccinated with such products would develop protective immune responses against LA.

Vaccines against MSD can also be based on live preparations of LA. Since only young piglets and pregnant sows seem to be seriously affected by infection with LA, it is possible to use unattenuated LA, grown in pig lung macrophages, as vaccine for older piglets, or breeding gilts. In this way, sows can be protected against MSD before they get pregnant, which results in protection against abortions and stillbirth, and against congenital infections of piglets. Also the maternal antibody that these vaccinated sows give to their offspring would protect their offspring against the disease.

Attenuated vaccines (modified-live-vaccines) against MSD can be made by serially passaging LA in pig lung macrophages, in lung macrophages of other species, or in other cell systems, or in other animals, such as rabbits, until it has lost its pathogenicity.

Live vaccines against MSD can also be made by recombinant DNA techniques through which the genome of LA, or parts thereof, is incorporated in vector systems such as vaccinia virus, herpesvirus, pseudorabies virus, adeno virus or other suitable vector systems that can so express LA antigen. Pigs vaccinated with such live vector systems would then develop protective immune responses against LA.

Lelystad Agent itself would be specifically suited to use as a live vector system. Foreign genes could be inserted in the genome of LA and could be expressing the corresponding protein during the infection of the macrophages. This cell, which is an antigen-presenting cell, would process the foreign antigen and present it to B-lymphocytes and T-lymphocytes which will respond with the appropriate immune response.

Since LA seems to be very cell specific and possibly also very species specific, this vector system might be a very safe system, which does not harm other cells or species.

DESCRIPTION OF THE DRAWINGS

FIG. 1 (SEQ ID NO:1) shows the nucleotide sequence of the LV genome. The deduced amino acid sequence of the identified ORFs (SEQ ID NOS:2-9) are shown. The methionines encoded by the (putative) ATG start sites are indicated in bold and putative N-glycosylation sites are underlined. Differences in the nucleotide and amino acid sequence, as identified by sequencing different cDNA clones, are shown. The nucleotide sequence of primer 25, which has been used in hybridization experiments (see FIG. 2 and section "results"), is underlined.

Figure 2:
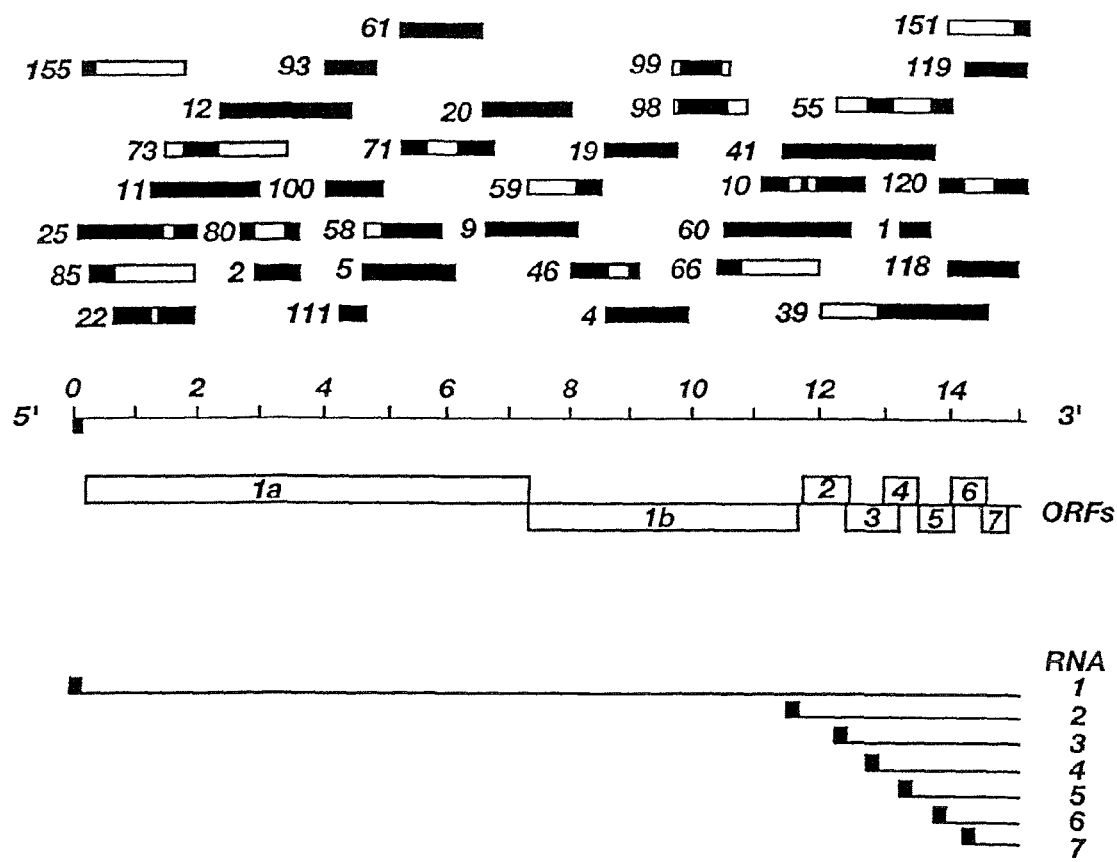
FIG. 2 shows the organization of the LV genome. The cDNA clones, which have been used for the determination of the nucleotide sequence, are indicated in the upper part of the figure. The parts of the clones, which were sequenced, are indicated in black. In the lower part of the figure the ORFs, identified in the nucleotide sequence, and the subgenomic set of mRNAs, encoding these ORFs are shown. The dashed lines in the ORFs represent alternative initiation sites (ATGs) of these ORFs. The leader sequence of the genomic and subgenomic RNAs is indicated by a solid box.

| | |
|---|---|
| -- empty squares -- | titre of cell-free virus; |
| -- solid squares -- | titre of cell-associated virus; |
| -- solid line -- | percentage cytopathic effect (CPE). |

MATERIALS AND METHODS

Sample Collection

Samples and pigs were collected from farms where a herd epizootic of MSD seemed to occur. Important criteria for selecting the farm as being affected with MSD were: sows that were off feed, the occurrence of stillbirth and abortion, weak offspring, respiratory disease and death among young piglets. Samples from four groups of pigs have been investigated:
(1) tissue samples and an oral swab from affected piglets from the field (Table 1A);
(2) blood samples and oral swabs from affected sows in the field (Tables 1B and 4);
(3) tissue samples, nasal swabs and blood samples collected from specific-pathogen-free (SPF) pigs experimentally infected by contact with affected sows from the field; or
(4) tissue samples, nasal swabs and blood samples collected from specific-pathogen-free (SPF) pigs experimentally infected by inoculation with blood samples of affected sows from the field (Tables 2 and 5).

Sample Preparation

Samples for virus isolation were obtained from piglets and sows which on clinical grounds were suspected to have MSD, and from experimentally infected SPF pigs, sows and their piglets.

Tissue samples were cut on a cryostat microtome and sections were submitted for direct immunofluorescence testing (IFT) with conjugates directed against various pig pathogens.

10% Suspensions of tissues samples were prepared in Hank's BSS supplemented with antibiotics, and oral and nasal swabs were soaked in Hank's BSS supplemented with antibiotics. After one hour at room temperature, the suspensions were clarified for 10 min at 6000 g and the supernatant was stored at −70° C. for further use. Leucocyte fractions were isolated from EDTA or heparin blood as described earlier (Wensvoort and Terpstra, 1988) and stored at −70° C. Plasma and serum for virus isolation were stored at −70° C.

Serum for serology was obtained from sows suspected to be in the acute phase of MSD, a paired serum was taken 3-9 weeks later. Furthermore, sera were taken from the experimentally infected SPF pigs at regular intervals and colostrum and serum was taken from experimentally infected sows and their piglets. Sera for serology were stored at −20° C.

Cells

Pig lung macrophages were obtained from lungs of 5-6 weeks old SPF pigs or from lungs of adult SPF sows from the Central Veterinary Institute's own herd. The lungs were washed five to eight times with phosphate buffered saline (PBS). Each aliquot of washing fluid was collected and centrifuged for 10 min at 300 g. The resulting cell pellet was washed again in PBS and resuspended in cell culture medium (160 ml medium 199, supplemented with 20 ml 2.95% tryptose phosphate, 20 ml fetal bovine serum (FBS), and 4.5 ml 1.4% sodium bicarbonate) to a concentration of $4\times10^7$ cells/ml. The cell suspension was then slowly mixed with an equal volume of DMSO mix (6.7 ml of above medium, 1.3 ml FBS, 2 ml dimethylsulfoxide 97%), aliquoted in 2 ml ampoules and stored in liquid nitrogen.

Macrophages from one ampoule were prepared for cell culture by washing twice in Earle's MEM, and resuspended in 30 ml growth medium (Earle's MEM, supplemented with 10% FBS, 200 U/ml penicillin, 0.2 mg/ml streptomycine, 100 U/ml mycostatin, and 0.3 mg/ml glutamine). PK-15 cells (American Type Culture Collection, CCL33) and SK-6 cells (Kasza et al., 1972) were grown as described by Wensvoort et al. (1989). Secondary porcine kidney (PK2) cells were grown in Earle's MEM, supplemented with 10% FBS and the above antibiotics. All cells were grown in a cell culture cabinet at 37° C. and 5% $CO^2$.

Virus Isolation Procedures

Virus isolation was performed according to established techniques using PK2, PK-15 and SK-6 cells, and pig lung macrophages. The former three cells were grown in 25 ml flasks (Greiner), and inoculated with the test sample when monolayers had reached 70-80% confluency. Macrophages were seeded in 100 µl aliquots in 96-well microtiter plates (Greiner) or in larger volumes in appropriate flasks, and inoculated with the test sample within one hour after seeding. The cultures were observed daily for cytopathic effects (CPE), and frozen at −70° C. when 50-70% CPE was reached or after five to ten days of culture. Further passages were made with freeze-thawed material of passage level 1 and 2 or higher. Some samples were also inoculated into nine to twelve day old embryonated hen eggs. Allantoic fluid was subinoculated two times using an incubation interval of three days and the harvest of the third passage was examined by haemagglutination at 4° C. using chicken red blood cells, and by an ELISA specifically detecting nucleoprotein of influenza A viruses (De Boer et al., 1990).

Serology

Sera were tested in haemagglutinating inhibition tests (HAI) to study the development of antibody against haemagglutinating encephalitis virus (HEV), and swine influenza viruses H1N1 and H3N2 according to the protocol of Masurel (1976). Starting dilutions of the sera in HAI were 1:9, after which the sera were diluted twofold.

Sera were tested in established enzyme-linked immunosorbent assays (ELISA) for antibodies against the glycoprotein gI of pseudorabies virus (PRV; Van Oirschot et al., 1988), porcine parvo virus (PPV; Westenbrink et al., 1989), bovine viral diarrhea virus (BVDV; Westenbrink et al., 1986), and hog cholera virus (HCV; Wensvoort et al., 1988). Starting dilutions in the ELISA's were 1:5, after which the sera were diluted twofold.

Sera were tested for neutralizing antibodies against 30-300 $TCID_{50}$ of encephalomyocarditis viruses (EMCV), porcine enteroviruses (PEV), and Lelystad Agent (LA) according to the protocol of Terpstra (1978). Starting dilutions of the sera in the serum neutralization tests (SNT) were 1:5, after which the sera were diluted twofold.

Sera were tested for binding with LA in an immuno-peroxidase-monolayer assay (IPMA). Lelystad Agent (LA; code: CDI-NL-2.91) was seeded in microtiter plates by adding 50 ml growth medium containing 100 $TCID_{50}$ LA to the wells of a microtiter plate containing freshly seeded lung macrophages. The cells were grown for two days and then fixed as described (Wensvoort, 1986). The test sera were diluted 1:10 in 0.15 M NaCl, 0.05% Tween 80, 4% horse serum, or diluted further in fourfold steps, added to the wells and then incubated for one hour at 37° C. Sheep-anti-pig immunoglobulins (Ig) conjugated to horse radish peroxidase (HRPO, DAKO) were diluted in the same buffer and used in a second incubation for one hour at 37° C., after which the plates were stained as described (Wensvoort et al., 1986). An intense red staining of the cytoplasm of infected macrophages indicated binding of the sera to LA.

Virus Identification Procedures

The identity of cytopathic isolates was studied by determining the buoyant density in CsCl, by estimating particle size in negatively stained preparations through electron microscopy, by determining the sensitivity of the isolate to chloroform and by neutralizing the CPE of the isolate with sera with known specificity (Table 3). Whenever an isolate was specifically neutralized by a serum directed against a known virus, the isolate was considered to be a representative of this known virus.

Isolates that showed CPE on macrophage cultures were also studied by staining in IPMA with post-infection sera of pigs c 829 or b 822. The isolates were reinoculated on macrophage cultures and fixed at day 2 after inoculation before the isolate showed CPE. Whenever an isolate showed reactivity in IPMA with the post-infection sera of pigs c 829 or b 822, the isolate was considered to be a representative of the Lelystad Agent. Representatives of the other isolates grown in macrophages or uninfected macrophages were also stained with these sera to check the specificity of the sera.

Further Identification of Lelystad Agent

Lelystad Agent was further studied by haemagglutination at 4° C. and 37° C. with chicken, guinea pig, pig, sheep, or human O red blood cells. SIV, subtype H3N2, was used as positive control in the haemagglutination studies.

The binding of pig antisera specifically directed against pseudorabies virus (PRV), transmissible gastroenteritis virus (TGE), porcine epidemic diarrhea virus (PED), haemagglutinating encephalitis virus (HEV), African swine fever virus (ASFV), hog cholera virus (HCV) and swine influenza virus (SIV) type H1N1 and H3N2, of bovine antisera specifically directed against bovine herpes viruses type 1 and 4 (BHV 1 and 4), malignant catarrhal fever (MCF), parainfluenza virus 3 (PI3), bovine respiratory syncitial virus (BRSV) and bovine leukemia virus (BLV), and of avian antisera specifically directed against avian leukemia virus (ALV) and infectious bronchitis virus (IBV) was studied with species-Ig-specific HRPO conjugates in an IPMA on LA infected and uninfected pig lung macrophages as described above.

We also tested in IPMA antisera of various species directed against mumps virus, Sendai virus, canine distemper virus, rinderpest virus, measles virus, pneumonia virus of mice, bovine respiratory syncytial virus, rabies virus, foamy virus, maedi-visna virus, bovine and murine leukemia virus, human, feline and simian immunodeficiency virus, lymphocytic choriomeningitis virus, feline infectious peritonitis virus, mouse hepatitis virus, Breda virus, Hantaan virus, Nairobi sheep disease virus, Eastern, Western and Venezuelan equine encephalomyelitis virus, rubella virus, equine arteritis virus, lactic dehydrogenase virus, yellow fever virus, tickborn encephalitis virus and hepatitis C virus.

LA was blindly passaged in PK2, PK-15, and SK-6 cells, and in embryonated hen eggs. After two passages, the material was inoculated again into pig lung macrophage cultures for reisolation of LA.

LA was titrated in pig lung macrophages prior to and after passing through a 0.2 micron filter (Schleicher and Schuell). The LA was detected in IPMA and by its CPE. Titres were calculated according to Reed and Muench (1938).

We further prepared pig antisera directed against LA. Two SPF pigs (21 and 23) were infected intranasally with $10^5$ $TCID_{50}$ of a fifth cell culture passage of LA. Two other SPF pigs (25 and 29) were infected intranasally with a fresh suspension of the lungs of an LA-infected SPF piglet containing 105 $TCID_{50}$ LA. Blood samples were taken at 0, 14, 28, and 42 days post-infection (dpi).

We further grew LA in porcine alveolar macrophages to determine its growth pattern over time. Porcine alveolar macrophages were seeded in F25 flasks (Greiner), infected with LA with a multiplicity of infection of 0.01 $TCID_{50}$ per cell. At 8, 16, 24, 32, 40, 48, 56, and 64 h after infection, one flask was examined and the percentage of CPE in relation to a noninfected control culture was determined. The culture medium was then harvested and replaced with an equal volume of phosphate-buffered saline. The medium and the flask were stored at −70° C. After all cultures had been harvested, the LA titres were determined and expressed as log $TCID_{50}$ $ml^{-1}$.

The morphology of LA was studied by electronmicroscopy. LA was cultured as above. After 48 h, the cultures were freeze-thawed and centrifuged for 10 min at 6000×g. An amount of 30 ml supernatant was then mixed with 0.3 ml LA-specific pig serum and incubated for 1.5 h at 37° C. After centrifugation for 30 min at 125,000×g, the resulting pellet was suspended in 1% Seakem agarose ME in phosphate-buffered saline at 40° C. After coagulation, the agarose block was immersed in 0.8% glutaraldehyde and 0.8% osmiumtetroxide (Hirsch et al., 1968) in veronal/acetate buffer, pH 7.4 (230 mOsm/kg $H_2O$), and fixed by microwave irradiation. This procedure was repeated once with fresh fixative. The sample was washed with water, immersed in 1% uranyl acetate, and stained by microwave irradiation. Throughout all steps, the sample was kept at 0° C. and the microwave (Samsung RE211D) was set at defrost for 5 min. Thin sections were prepared with standard techniques, stained with lead citrate (Venable et al., 1965), and examined in a Philips CM 10 electron microscope.

We further continued isolating LA from sera of pigs originating from cases of MSD. Serum samples originated from the Netherlands (field case the Netherlands 2), Germany (field cases Germany 1 and Germany 2; courtesy Drs. Berner, München and Nienhoff, Münster), and the United States [experimental case United States 1 (experiment performed with ATCC VR-2332; courtesy Drs. Collins, St. Paul and Chladek, St. Joseph), and field cases United States 2 and United States 3; courtesy Drs. van Alstine, West Lafayette and Slife, Galesburg]. All samples were sent to the "Centraal Diergeneeskundig Instituut, Lelystad" for LA diagnosis. All samples were used for virus isolation on porcine alveolar macrophages as described. Cytophatic isolates were passaged three times and identified as LA by specific immunostaining with anti-LA post infection sera b 822 and c 829.

We also studied the antigenic relationships of isolates NL1 (the first LA isolate; code CDI-NL-2.91), NL2, GE1, GE2, US1, US2, and US3. The isolates were grown in macrophages as above and were tested in IPMA with a set of field sera and two sets of experimental sera. The sera were also tested in IPMA with uninfected macrophages.

The field sera were: Two sera positive for LV (TH-187 and TO-36) were selected from a set of LA-positive Dutch field sera. Twenty-two sera were selected from field sera sent from abroad to Lelystad for serological diagnosis. The sera originated from Germany (BE-352, BE-392 and NI-f2; courtesy Dr. Berner, München and Dr. Nienhoff, Münster), the United Kingdom (PA-141615, PA-141617 and PA-142440; courtesy Dr. Paton, Weybridge), Belgium (PE-1960; courtesy Prof. Pensaert, Gent), France (EA-2975 and EA-2985; courtesy Dr. Albina, Ploufragan), the United States (SL-441, SL-451, AL-RP9577, AL-P10814/33, AL-4994A, AL-7525, JC-MN41, JC-MN44 and JC-MN45; courtesy Dr. Slife, Galesburg, Dr. van Alstine, West Lafayette, and Dr. Collins, St. Paul), and Canada (RB-16, RB-19, RB-22 and RB-23; courtesy Dr. Robinson, Quebec).

The experimental sera were: The above described set of sera of pigs 21, 23, 25, and 29, taken at dpi 0, 14, 28, and 42. A set of experimental sera (obtained by courtesy of Drs. Chladek, St. Joseph, and Collins, St. Paul) that originated from four six-month-old gilts that were challenged intranasally with $10^{5.1}$ TCID$_{50}$ of the isolate ATCC VR-2332. Blood samples were taken from gilt 2B at 0, 20, 36, and 63 dpi; from gilt 9G at 0, 30, 44, and 68 dpi; from gilt 16W at 0, 25, 40, and 64 dpi; and from gilt 16Y at 0, 36, and 64 dpi.

To study by radio-immunoprecipitation assay (RIP; de Mazancourt et al., 1986) the proteins of LA in infected porcine alveolar macrophages, we grew LA-infected and uninfected macrophages for 16 hours in the presence of labeling medium containing $^{35}$S-Cysteine. Then the labeled cells were precipitated according to standard methods with 42 dpi post-infection sera of pig b 822 and pig 23 and with serum MN8 which was obtained 26 days after infecting a sow with the isolate ATCC VR-2332 (courtesy Dr. Collins, St. Paul). The precipitated proteins were analyzed by electrophoresis in a 12% SDS-PAGE gel and visualized by fluorography.

To characterize the genome of LA, we extracted nuclear DNA and cytoplasmatic RNA from macrophage cultures that were infected with LA and grown for 24 h or were left uninfected. The cell culture medium was discarded, and the cells were washed twice with phosphate-buffered saline. DNA was extracted as described (Strauss, 1987). The cytoplasmic RNA was extracted as described (Favaloro et al., 1980), purified by centrifugation through a 5.7 M CsCl cushion (Setzer et al., 1980), treated with RNase-free DNase (Pharmacia), and analyzed in a 0.8% neutral agarose gel (Moormann and Hulst, 1988).

Cloning and Sequencing

To clone LV RNA, intracellular RNA of LV-infected porcine lung alveolar macrophages (10 μg) was incubated with 10 mM methylmercury hydroxide for 10 minutes at room temperature. The denatured RNA was incubated at 42° C. with 50 mM Tris-HCl1 pH 7.8, 10 mM $MgCl_2$, 70 mM KCl, 0.5 mM dATP, dCTP, dGTP and dTTP, 0.6 μg calf thymus oligonucleotide primers pd(N)6 (Pharmacia) and 300 units of Moloney murine leukemia virus reverse transcriptase (Bethesda Research Laboratories) in a total volume of 100 μl 20 mM EDTA was added after 1 hr; the reaction mixture was then extracted with phenol/chloroform, passed through a Sephadex G50 column and precipitated with ethanol.

For synthesis of the second cDNA strand, DNA polymerase 1 (Boehringer) and RNase H (Pharmacia) were used (Gübler and Hoffman, 1983). To generate blunt ends at the termini, double-stranded cDNA was incubated with T4 DNA polymerase (Pharmacia) in a reaction mixture which contained 0.05 mM deoxynucleotide-triphosphates. Subsequently, cDNA was fractionated in a 0.8% neutral agarose gel (Moormann and Hulst, 1988). Fragments of 1 to 4 kb were electroeluted, ligated into the SmaI site of pGEM-4Z (Promega), and used for transformation of *Escherichia coli* strain DH5α (Hanahan, 1985). Colony filters were hybridized with a $^{32}P$-labeled single-stranded cDNA probe. The probe was reverse transcribed from LV RNA which had been fractionated in a neutral agarose gel (Moormann and Hulst, 1988). Before use, the single stranded DNA probe was incubated with cytoplasmic RNA from mock-infected lung alveolar macrophages.

The relationship between LV cDNA clones was determined by restriction enzyme analysis and by hybridization of Southern blots of the digested DNA with nick-translated cDNA probes (Sambrook et al., 1989).

To obtain the 3' end of the viral genome, we constructed a second cDNA library, using oligo $(dT)_{12-18}$ and a 3' LV-specific oligonucleotide that was complementary to the minus-strand viral genome as a primer in the first-strand reaction. The reaction conditions for first- and second-strand synthesis were identical to those described above. This library was screened with virus-specific 3' end oligonucleotide probes.

Most (>95%) of the cDNA sequences were determined with an Automated Laser Fluorescent A.L.F.™ DNA sequencer from Pharmacia LKB. Fluorescent oligonucleotide primer directed sequencing was performed on double-stranded DNA using the AutoRead™ Sequencing Kit (Pharmacia) essentially according to procedures C and D described in the Autorcad™ Sequencing Kit protocol. Fluorescent primers were prepared with FluorePrime™ (Pharmacia). The remaining part of the sequence was determined via double-stranded DNA sequencing using oligonucleotide primers in conjunction with a T7 polymerase based sequencing kit (Pharmacia) and α-$^{32}S$-dATP (Amersham). Sequence data were analyzed using the sequence analysis programs PCGENE (Intelligenetics, Inc, Mountain View, USA) and FASTA (Pearson and Lipman, 1988).

Experimental Reproduction of MSD

Fourteen conventionally reared pregnant sows that were pregnant for 10-11 weeks were tested for antibody against LA in the IPMA. All were negative. Then two groups of four sows were formed and brought to the CVI. At week 12 of gestation, these sows were inoculated intranasally with 2 ml LA (passage level 3, titre $10^{4.8}$ $TCID_{50}$/ml). Serum and EDTA blood samples were taken at day 10 after inoculation. Food intake, rectal temperature, and other clinical symptoms were observed daily. At farrowing, the date of birth and the number of dead and living piglets per sow were recorded, and samples were taken for virus isolation and serology.

Results

Immunofluorescence

Tissue sections of pigs with MSD were stained in an IFT with FITC-conjugates directed against African swine fever virus, hog cholera virus, pseudorabies virus, porcine parvo virus, porcine influenza virus, encephalomyocarditis virus and Chlamydia psittaci. The sections were stained, examined by fluorescent microscopy and all were found negative.

Virus Isolation from Piglets from MSD Affected Farms

Cytopathic isolates were detected in macrophage cultures inoculated with tissue samples of MSD affected, two-to-ten day old piglets. Sixteen out of 19 piglets originating from five different farms were positive (Table 1A). These isolates all reacted in IPMA with the post-infection serum of pig c 829, whereas non-inoculated control cultures did not react. The isolates, therefore, were representatives of LA. One time a cytopathic isolate was detected in an SK-6 cell culture inoculated with a suspension of an oral swab from a piglet from a sixth farm (farm VE) (Table 1A). This isolate showed characteristics of the picorna viridae and was neutralized by serum specific for PEV 2, therefore, the isolate was identified as PEV 2 (Table 3). PK2, PK-15 cells and hen eggs inoculated with samples from this group remained negative throughout.

Virus Isolation from Sows from MSD Affected Farms

Cytopathic isolates were detected in macrophage cultures inoculated with samples of MSD affected sows. 41 out of 63 sows originating from 11 farms were positive (Table 1B). These isolates all reacted in IPMA with the post-infection serum of pig b 822 and were, therefore, representatives of LA. On one occasion a cytopathic isolate was detected in a PK2 cell culture inoculated with a suspension of a leucocyte fraction of a sow from farm HU (Table 1B). This isolate showed characteristics of the picorna viridae and was neutralized by serum specific for EMCV, therefore, the isolate was identified as EMCV (Table 3). SK-6, PK-15 cells and hen eggs inoculated with samples from this group remained negative.

Virus Isolation from SPF Pigs Kept in Contact with MSD Affected Sows

Cytopathic isolates were detected in macrophage cultures inoculated with samples of SPF pigs kept in contact with MSD affected sows. Four of the 12 pigs were positive (Table 2). These isolates all reacted in IPMA with the post-infection serum of pig c 829 and of pig b 822 and were, therefore, representatives of LA. Cytopathic isolates were also detected in PK2, PK-15 and SK-6 cell cultures inoculated with samples of these SPF pigs. Seven of the 12 pigs were positive (Table 2), these isolates were all neutralized by serum directed against PEV 7. One of these seven isolates was studied further and other characteristics also identified the isolate as PEV 7 (Table 3).

Virus Isolation from SPF Pigs Inoculated with Blood of MSD Affected Sows

Cytopathic isolates were detected in macrophage cultures inoculated with samples of SPF pigs inoculated with blood of MSD affected sows. Two out of the eight pigs were positive (Table 2). These isolates all reacted in IPMA with the post-infection serum of pig c 829 and of pig b 822 and were, therefore, representatives of LA. PK2, SK-6 and PK-15 cells inoculated with samples from this group remained negative.

Summarizing, four groups of pigs were tested for the presence of agents that could be associated with mystery swine disease (MSD).

In group one, MSD affected piglets, the Lelystad Agent (LA) was isolated from 16 out of 20 piglets; one time PEV 2 was isolated.

In group two, MSD affected sows, the Lelystad Agent was isolated from 41 out of 63 sows; one time EMCV was isolated. Furthermore, 123 out of 165 MSD affected sows seroconverted to the Lelystad Agent, as tested in the IPMA. Such massive seroconversion was not demonstrated against any of the other viral pathogens tested.

In group three, SPF pigs kept in contact with MSD affected sows, LA was isolated from four of the 12 pigs; PEV 7 was isolated from seven pigs. All 12 pigs seroconverted to LA and PEV 7.

In group four, SPF pigs inoculated with blood of MSD affected sows, the LA was isolated from two pigs. All eight pigs seroconverted to LA.

Serology of Sows from MSD Affected Farms

Paired sera from sows affected with MSD were tested against a variety of viral pathogens and against the isolates obtained during this study (Table 4). An overwhelming antibody response directed against LA was measured in the IPMA (75% of the sows seroconverted, in 23 out of the 26 farms seroconversion was found), whereas with none of the other viral pathogens a clear pattern of seroconversion was found. Neutralizing antibody directed against LA was not detected.

Serology of SPF Pigs Kept in Contact with MSD Affected Sows

All eight SPF pigs showed an antibody response in the IPMA against LA (Table 5). None of these sera were positive in the IPMA performed on uninfected macrophages. None of these sera were positive in the SNT for LA. The sera taken two weeks after contact had all high neutralizing antibody titres (>1280) against PEV 7, whereas the pre-infection sera were negative (<10), indicating that all pigs had also been infected with PEV 7.

Serology of SPF Pigs Inoculated with Blood of MSD Affected Sows

All eight SPF pigs showed an antibody response in the IPMA against LA (Table 5). None of these sera were positive in the IPMA performed on uninfected macrophages. None of these sera were positive in the SNT for LA. The pre- and two weeks post-inoculation sera were negative (<10) against PEV 7.

Further Identification of Lelystad Agent

LA did not haemagglutinate with chicken, guinea pig, pig, sheep, or human O red blood cells.

LA did not react in IPMA with sera directed against PRV, TGE, PED, ASFV, etc.

After two blind passages, LA did not grow in PK2, PK-15, or SK-6 cells, or in embryonated hen eggs, inoculated through the allantoic route.

LA was still infectious after it was filtered through a 0.2 micron filter, titres before and after filtration were $10^{5.05}$ and $10^{5.3}$ TCID$_{50}$ as detected by IPMA.

Figure 3:
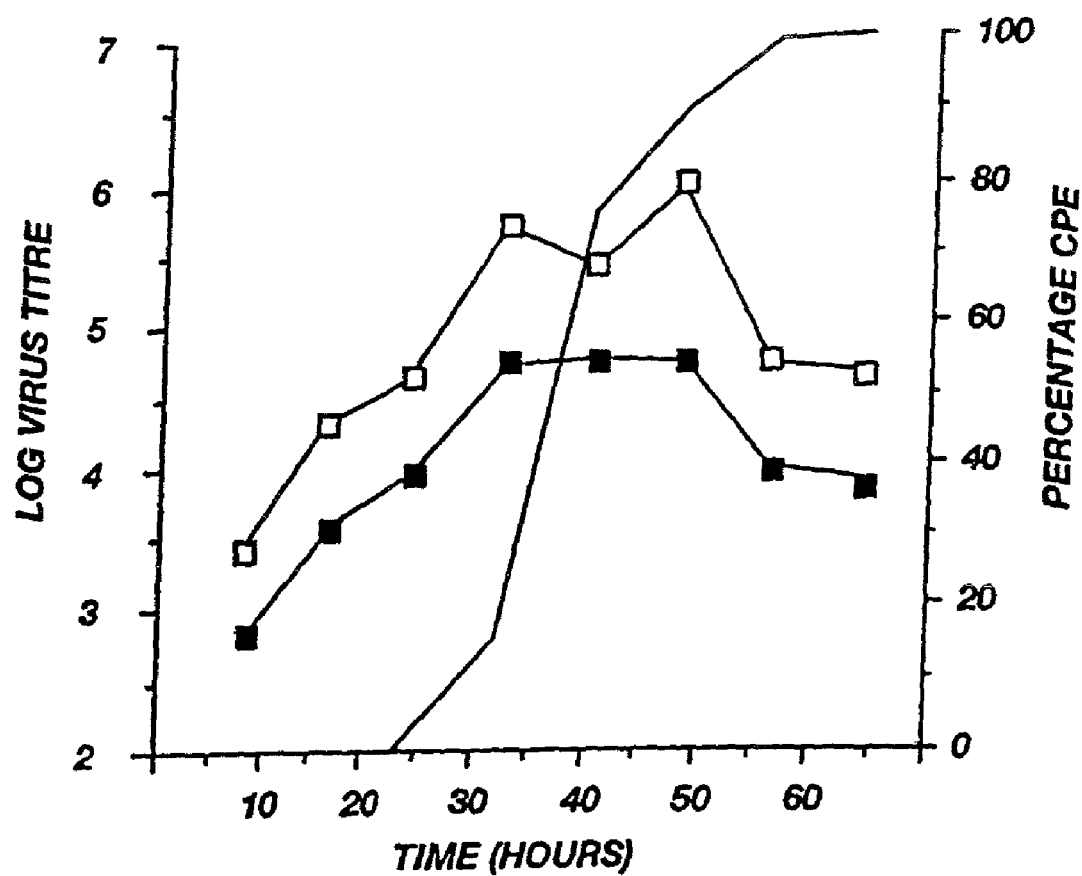
FIG. 3 shows the growth characteristics of LA.

Growth curve of LA (see FIG. 3). Maximum titres of cell-free virus were approximately $10^{5.5}$ TCID$_{50}$ ml$^{-1}$ from 32-48 h after inoculation. After that time the macrophages were killed by the cytopathic effect of LA.

Electronmicroscopy. Clusters of spherical LA particles were found. The particles measured 45-55 nm in diameter and contained a 30-35 nm nucleocapsid that was surrounded by a lipid bilayer membrane. LA particles were not found in infected cultures that were treated with negative serum or in negative control preparations.

Isolates from the Netherlands, Germany, and the United States. All seven isolates were isolated in porcine alveolar macrophages and passaged three to five times. All isolates caused a cytopathic effect in macrophages and could be specifically immunostained with anti-LA sera b 822 and the 42 dpi serum 23. The isolates were named NL2, GE1, GE2, US1, US2, and US3.

Antigenic relationships of isolates NL1, NL2, GE1, GE2, US1, US2, and US3. None of the field sera reacted in IPMA with uninfected macrophages but all sera contained antibodies directed against one or more of the seven isolates (Table 7). None of the experimental sera reacted in IPMA with uninfected macrophages, and none of the 0 dpi experimental sera reacted with any of the seven isolates in IPMA (Table 8). All seven LA isolates reacted with all or most of the sera from the set of experimental sera of pigs 21, 23, 25, and 29, taken after 0 dpi. Only the isolates US1, US2, and US3 reacted with all or most of the sera from the set of experimental sera of gilts 2B, 9G, 16W, and 16Y, taken after 0 dpi.

Radioimmunoprecipitation studies. Seven LA-specific proteins were detected in LA-infected macrophages but not in uninfected macrophages precipitated with the 42 dpi sera of pigs b 822 and 23. The proteins had estimated molecular weights of 65, 39, 35, 26, 19, 16, and 15 kilodalton. Only two of these LA-specific proteins, of 16 and 15 kilodalton, were also precipitated by the 26 dpi serum MN8.

Sequence and Organization of the Genome of LV

The nature of the genome of LV was determined by analyzing DNA and RNA from infected porcine lung alveolar macrophages. No LV-specific DNA was detected. However, we did detect LV-specific RNA. In a 0.8% neutral agarose gel, LV RNA migrated slightly slower than a preparation of hog cholera virus RNA of 12.3 kb (Moormann et al., 1990) did. Although no accurate size determination can be performed in neutral agarose gels, it was estimated that the LV-specific RNA is about 14.5 to 15.5 kb in length.

To determine the complexity of the LV-specific RNAs in infected cells and to establish the nucleotide sequence of the genome of LV, we prepared cDNA from RNA of LV-infected porcine lung alveolar macrophages and selected and mapped LV-specific cDNA clones as described under Materials and Methods. The specificity of the cDNA clones was reconfirmed by hybridizing specific clones, located throughout the overlapping cDNA sequence, to Northern blots carrying RNA of LV-infected and uninfected macrophages. Remarkably, some of the cDNA clones hybridized with the 14.5 to 15.5 kb RNA detected in infected macrophages only, whereas others hybridized with the 14.5 to 15.5 kb RNA as well as with a panel of 4 or 5 RNAs of lower molecular weight (estimated size, 1 to 4 kb). The latter clones were all clustered at one end of the cDNA map and covered about 4 kb of DNA. These data suggested that the genome organization of LV may be similar to that of coronaviridae (Spaan et al., 1988), Berne virus (BEV; Snijder et al., 1990b), a torovirus, and EAV (de Vries et al., 1990), i.e., besides a genomic RNA there are subgenomic mRNAs which form a nested set which is located at the 3' end of the genome. This assumption was confirmed when sequences of the cDNA clones became available and specific primers could be selected to probe the blots with. A compilation of the hybridization data obtained with cDNA clones and specific primers, which were hybridized to Northern blots carrying the RNA of LV-infected and uninfected macrophages, is shown in FIG. 2. Clones 12 and 20 which are located in the 5' part and the centre of the sequence, respectively, hybridize to the 14.5 to 15.5 kb genomic RNA detected in LV-infected cells only. Clones 41 and 39, however, recognize the 14.5 to 15.5 kb genomic RNA and a set of 4 and 5 RNAs of lower molecular weight, respectively. The most instructive and conclusive hybridization pattern, however, was obtained with primer 25, which is located at the ultimate 5' end in the LV sequence (compare FIG. 1). Primer 25 hybridized to a panel of 7 RNAs, with an estimated molecular weight ranging in size from 0.7 to 3.3 kb (subgenomic mRNAs), as well as the genomic RNA. The most likely explanation for the hybridization pattern of primer 25 is that 5' end genomic sequences, the length of which is yet unknown, fuse with the body of the mRNAs which are transcribed from the 3' end of the genome. In fact, the hybridization pattern obtained with primer 25 suggests that 5' end genomic sequences function as a so called "leader sequence" in subgenomic mRNAs. Such a transcription pattern is a hallmark of replication of coronaviridae (Spaan et al., 1988), and of EAV (de Vries et al., 1990).

The only remarkable discrepancy between LV and EAV which could be extracted from the above data is that the genome size of LV is about 2.5 kb larger than that of EAV.

The consensus nucleotide sequence of overlapping cDNA clones is shown in FIG. 1 (SEQ ID NO:1). The length of the sequence is 15,088 basepairs, which is in good agreement with the estimated size of the genomic LV RNA.

Since the LV cDNA library was made by random priming of the reverse transcriptase reaction with calf thymus pd(N) 6 primers, no cDNA clones were obtained which started with a poly-A stretch at their 3' end. To clone the 3' end of the viral genome, we constructed a second cDNA library, using oligo (dT) and primer 39U183R in the reverse transcriptase reaction. Primer 39U183R is complementary to LV minus-strand RNA, which is likely present in a preparation of RNA isolated from LV-infected cells. This library was screened with virus-specific probes (nick-translated cDNA clone 119 and oligonucleotide 119R64R), resulting in the isolation of five additional cDNA clones (e.g., cDNA clone 151, FIG. 2). Sequencing of these cDNA clones revealed that LV contains a 3' poly(A) tail. The length of the poly(A) tail varied between the various cDNA clones, but its maximum length was twenty nucleotides. Besides clone 25 and 155 (FIG. 2), four additional cDNA clones were isolated at the 5' end of the genome, which were only two to three nucleotides shorter than the ultimate 5' nucleotide shown in FIG. 1 (SEQ ID NO:1). Given this finding and given the way cDNA was synthesized, we assume to be very close to the 5' end of the sequence of LV genomic RNA.

Nearly 75% of the genomic sequence of LV encodes ORF 1A and ORF 1B. ORF 1A probably initiates at the first AUG (nucleotide position 212, FIG. 1) encountered in the LV sequence. The C-terminus of ORF 1A overlaps the putative N-terminus of ORF 1B over a small distance of 16 nucleotides. It thus seems that translation of ORF 1B proceeds via ribosomal frameshifting, a hallmark of the mode of translation of the polymerase or replicase gene of coronaviruses (Boursnell et al., 1987; Bredenbeek et al. 1990) and the torovirus BEV (Snijder et al., 1990a). The characteristic RNA pseudoknot structure which is predicted to be formed at the site of the ribosomal frameshifting is also found at this location in the sequence of LV (results not shown).

ORF 1B encodes an amino acid sequence (SEQ ID NO:3) of nearly 1400 residues which is much smaller than ORF 1B of the coronaviruses MHV and IBV (about 3,700 amino acid residues; Bredenbeek et al., 1990; Boursnell et al., 1987) and BEV (about 2,300 amino acid residues; Snijder et al., 1990a). Characteristic features of the ORF 1B product (SEQ ID NO:3) of members of the superfamily of coronaviridae, like the replicase motif and the Zinc finger domain, can also be found in ORF 1B of LV (results not shown).

Whereas ORF 1A and ORF 1B encode the viral polymerase (SEQ ID NO:2 and SEQ ID NO:3) and, therefore, are considered to encode a non-structural viral protein, ORFs 2 to 7 are believed to encode structural viral proteins (SEQ ID NOS:4-9).

The products of ORFs 2 to 6 (SEQ ID NOS:4-8) all show features reminiscent of membrane (envelope) associated proteins. ORF 2 encodes a protein (SEQ ID NO:4) of 249 amino acids containing two predicted N-linked glycosylation sites (Table 9). At the N-terminus a hydrophobic sequence, which may function as a so-called signal sequence, is identified. The C-terminus also ends with a hydrophobic sequence, which in this case may function as a transmembrane region, which anchors the ORF 2 product (SEQ ID NO:4) in the viral envelope membrane.

ORF 3 may initiate at the AUG starting at nucleotide position 12394 or at the AUG starting at nucleotide position 12556 and then encodes proteins (SEQ ID NO:5) of 265 and 211 amino acids, respectively. The protein of 265 residues contains seven putative N-linked glycosylation sites, whereas the protein of 211 residues contains four (Table 9). At the N-terminus of the protein (SEQ ID NO:5) of 265 residues a hydrophobic sequence is identified.

Judged by hydrophobicity analysis, the topology of the protein encoded by ORF 4 (SEQ ID NO:6) is similar to that encoded by ORF 2 (SEQ ID NO:4) if the product of ORF 4 (SEQ ID NO:6) initiates at the AUG starting at nucleotide position 12936. However, ORF 4 may also initiate at two other AUG codons (compare FIGS. 1 and 2) starting at positions 12981 and 13068 in the sequence respectively. Up to now it is unclear which start codon is used. Depending on the start codon used, ORF 4 may encode proteins (SEQ ID NO:6) of 183 amino acids containing four putative N-linked glycosylation sites, of 168 amino acids containing four putative N-linked glycosylation sites, or of 139 amino acids containing three putative N-linked glycosylation sites (Table 9).

ORF 5 is predicted to encode a protein (SEQ ID NO:7) of 201 amino acids having two putative N-linked glycosylation sites (Table 9). A characteristic feature of the ORF 5 product (SEQ ID NO:7) is the internal hydrophobic sequence between amino acid 108 to amino acid 132.

Analysis for membrane spanning segments and hydrophilicity of the product of ORF 6 (SEQ ID NO:8) shows that it contains three transmembrane spanning segments in the N-terminal 90 amino acids of its sequence. This remarkable feature is also a characteristic of the small envelope glycoprotein M or E1 of several coronaviruses, e.g., Infectious Bronchitis Virus (IBV; Boursnell et al., 1984) and Mouse Hepatitis Virus (MHV: Rottier et al., 1986). It is, therefore, predicted that the protein encoded by ORF 6 (SEQ ID NO:8) was a membrane topology analogous to that of the M or E1 protein of coronaviruses (Rottier et al., 1986). A second characteristic of the M or E1 protein is a so-called surface helix which is located immediately adjacent to the presumed third transmembrane region. This sequence of about 25 amino acids which is very well conserved among coronaviruses is also recognized, although much more degenerate, in LV. Yet we predict the product of LV ORF 6 (SEQ ID NO:8) to have an analogous membrane associated function as the coronavirus M or E1 protein. Furthermore, the protein encoded by ORF 6 (SEQ ID NO:8) showed a strong similarity (53% identical amino acids) with VpX (Godeny et al., 1990) of LDV.

The protein encoded by ORF 7 (SEQ ID NO:9) has a length of 128 amino acid residues (Table 9) which is 13 amino acids longer than Vp1 of LDV (Godeny et al., 1990). Yet a significant similarity (43% identical amino acids) was observed between the protein encoded by ORF 7 (SEQ ID NO:9) and Vp1. Another shared characteristic between the product of ORF 7 (SEQ ID NO:9) and Vp1 is the high concentration of basic residues (Arg, Lys and His) in the N-terminal half of the protein. Up to amino acid 55, the LV sequence contains 26% Arg, Lys and His. This finding is fully in line with the proposed function of the ORF 7 product (SEQ ID NO:9) or Vp1 (Godeny et al., 1990), namely encapsidation of the viral genomic RNA. On the basis of the above data, we propose the LV ORF 7 product (SEQ ID NO:9) to be the nucleocapsid protein N of the virus.

A schematic representation of the organization of the LV genome is shown in FIG. 2. The map of overlapping clones used to determine the sequence of LV is shown in the top panel. A linear compilation of this map indicating the 5' and 3' end of the nucleotide sequence of LV, shown in FIG. 1 (SEQ ID NO:1), including a division in kilobases, is shown below the map of cDNA clones and allows the positioning of these clones in the sequence. The position of the ORFs identified in the LV genome is indicated below the linear map of the LV sequence. The bottom panel shows the nested set of subgenomic mRNAs, and the position of these RNAs relative to the LV sequence.

In line with the translation strategy of coronavirus, torovirus and arterivirus subgenomic mRNAs, it is predicted that ORFs 1 to 6 are translated from the unique 5' end of their genomic or mRNAs. This unique part of the mRNAs is considered to be that part of the RNA that is obtained when a lower molecular weight RNA is "subtracted" from the higher molecular weight RNA which is next in line. Although RNA 7 forms the 3' end of all the other genomic and subgenomic RNAs, and thus does not have a unique region, it is believed that ORF 7 is only translated from this smallest sized mRNA. The "leader sequence" at the 5' end of the subgenomic RNAs is indicated with a solid box. The length of this sequence is about 200 bases, but the precise site of fusion with the body of the genomic RNAs still has to be determined.

Experimental Reproduction of MSD

Eight pregnant sows were inoculated with LA and clinical signs of MSD such as inappetance and reproductive losses were reproduced in these sows. From day four to day 10-12 post-inoculation (p.i.), all sows showed a reluctance to eat. None of the sows had elevated body temperatures. Two sows had bluish ears at day 9 and 10 p.i. In Table 6 the day of birth and the number of living and dead piglets per sow is given. LA was isolated from 13 of the born piglets.

TABLE 1

Description and results of virus isolation of field samples.

A Samples of piglets suspected of infection with MSD.

| farm | number of pigs | age days | material used | results* |
|---|---|---|---|---|
| RB | 5 | 2 | lung, tonsil, and brains | 5 × LA |
| DV | 4 | 3 | lung, brains, pools of kidney, spleen | 3 × LA |
| TH | 3 | 3-5 | lung, pools of kidney, tonsil | 3 × LA |
| DO | 3 | 10 | lung, tonsil | 2 × LA |
| ZA | 4 | 1 | lung, tonsil | 3 × LA |
| VE | 1 | ? | oral swab | 1 × PEV 2 |
| TOTAL | 20 | | | 16 × LA, 1 × PEV 2 |

B Samples of sows suspected of infection with MSD.

| farm | number of sows | material used | results |
|---|---|---|---|
| TH | 2 | plasma and leucocytes | 1 × LA |
| HU | 5 | plasma and leucocytes | 2 × LA, 1 × EMCV |
| TS | 10 | plasma and leucocytes | 6 × LA |
| HK | 5 | plasma and leucocytes | 2 × LA |
| LA | 6 | plasma and leucocytes | 2 × LA |
| VL | 6 | serum and leucocytes | 5 × LA |
| TA | 15 | serum | 11 × LA |

TABLE 1-continued

Description and results of virus isolation of field samples.

| | | | |
|---|---|---|---|
| LO | 4 | plasma and leucocytes | 2 × LA |
| JA | 8 | plasma and leucocytes | 8 × LA |
| VD | 1 | plasma and leucocytes | 1 × LA |
| VW | 1 | serum | 1 × LA |
| TOTAL | 63 | | 41 × LA, 1 × EMCV |

*Results are given as the number of pigs from which the isolation was made. Sometimes the isolate was detected in more than one sample per pig.
LA = Lelystad Agent
PEV 2 = porcine entero virus type 2
EMCV = encephalomyocarditis virus

TABLE 2

Description and results of virus isolation of samples of pigs with experimentally induced infections.

| sow | pig@ | material used | results* |
|---|---|---|---|
| A (LO)# | c 835 | lung, tonsil | 2 × LA |
| | c 836 | nasal swabs | 2 × PEV 7 |
| | c 837 | nasal swabs | |
| B (JA) | c 825 | lung, tonsil | |
| | c 821 | nasal swabs | 1 × PEV 7 |
| | c 823 | nasal swabs | 4 × PEV 7 |
| C (JA) | c 833 | lung, tonsil | 1 × LA, 1 × PEV 7 |
| | c 832 | nasal swabs | 2 × PEV 7 |
| | c 829 | nasal swabs, plasma and leucocytes | 3 × LA, 2 × PEV 7 |

TABLE 2-continued

Description and results of virus isolation of samples of pigs with experimentally induced infections.

| sow | pig@ | material used | results* |
|---|---|---|---|
| D (VD) | c 816 | lung, tonsil | |
| | c 813 | nasal swabs | 1 × LA |
| | c 815 | nasal swabs | 1 × PEV 7 |
| TOTAL isolates from contact pigs | | | 7 × LA, 13 × PEV 7 |
| A | b 809 | nasal swabs | |
| | b 817 | nasal swabs | |
| B | b 818 | nasal swabs, plasma and leucocytes | 1 × LA |
| | b 820 | nasal swabs | |
| C | b 822 | nasal swabs | |
| | b 826 | nasal swabs | |
| D | b 830 | nasal swabs | 1 × LA |
| | b 834 | nasal swabs | |
| TOTAL isolates from blood inoculated pigs | | | 2 × LA |

@SPF pigs were either kept in contact (c) with a sow suspected to be infected with MSD, or were given 10 ml EDTA blood (b) of that sow intramuscularly at day 0 of the experiment. Groups of one sow and three SPF pigs (c) were kept in one pen, and all four of these groups were housed in one stable. At day 6, one SPF pig in each group was killed and tonsil and lungs were used for virus isolation. The four groups of SPF pigs inoculated with blood (b) were housed in four other pens in a separate stable. Nasal swabs of the SPF pigs were taken at day 2, 5, 7 and 9 of the experiment, and EDTA blood for virus isolation from plasma and leucocytes was taken whenever a pig had fever.
*Results are given as number of isolates per pig.
LA = Lelystad Agent
PEV 7 = procine entero virus type 7
In brackets the initials of the farm of origin of the sow are given.

TABLE 3

Identification of viral isolates

| origin and cell culture | buoyant[1] density size in in CsCl | particle[2] FM (nm) | sens[3] to chloroform | neutralized by[4] serum directed against (titre) |
|---|---|---|---|---|
| leucocytes sow farm HU PK-15, PK2, SK6 | 1.33 g/ml | 28-30 | not sens. | EMCV (1280) |
| oral swab piglet farm VEND SK6 | | 28-30 | not sens. | PEV 2 (>1280) |
| nasal swabs, tonsil SPF pigs CVI PK-15, PK2, SK6 | ND | 28-30 | not sens. | PEV 7 (>1280) |
| various samples various farms pig lung macrophages | 1.19 g/ml | pleomorf | sens. | none (all <5) |

[1]Buoyant density in preformed linear gradients of CsCl in PBS was determined according to standard techniques (Brakke; 1967). Given is the density where the peak of infectivity was found.

[2]Infected and noninfected cell cultures of the isolate under study were freeze-thawed. Cell lysates were centrifuged for 30 min at 130,000 g, the resulting pellet was negatively stained according to standard techniques (Brenner and Horne; 1959), and studied with a Philips CM 10 electron microscope. Given is the size of particles that were present in infected and not present in non-infected cultures.

[3]Sensitivity to chloroform was determined according to standard techniques (Grist, Ross, and Bell; 1974).

[4]Hundred to 300 TCID$_{50}$ of isolates were mixed with varying dilutions of specific antisera and grown in the appropriate cell system until full CPE was observed. Sera with titres higher than 5 were retested, and sera which blocked with high titres the CPE were considered specific for the isolate. The isolates not sensitive to chloroform were tested with sera specifically directed against porcine entero viruses (PEV) 1 to 11 (courtesy Dr. Knowles, Pirbright, UK), against encephalomyocarditis virus (EMCV; courtesy Dr. Ahl, Tübingen, Germany), against porcine parvo virus, and against swine vesicular disease.

The isolate (code: CDI-NL-2.91) sensitive to chloroform was tested with antisera specifically directed against pseudorabies virus, bovine herpes virus 1, bovine herpes virus 4, malignant catarrhal virus, bovine viral diarrhea virus, hog cholera virus, swine influenza virus H1N1 and H3N2, parainfluenza 3 virus, bovine respiratory syncitial virus, transmissible gastroenteritis virus, porcine epidemic diarrhoea virus, haemagglutinating encephalitis virus, infectious bronchitis virus, bovine leukemia virus, avian leukemia virus, maedi-visna virus, and with the experimental sera obtained from the SPF-pigs (see Table 5).

TABLE 4

Results of serology of paired field sera taken from sows suspected to have MSD. Sera were taken in the acute phase of the disease and 3-9 weeks later. Given is the number of sows which showed a fourfold or higher rise in titre/number of sows tested.

| Farm | Interval[i] in weeks | HAI HEV | ELISA H1N1 | H3N2 | PPV | PPV | BVDV | HCV |
|---|---|---|---|---|---|---|---|---|
| TH | 3 | 0/6 | 0/6 | 0/6 | 0/6 | 0/6 | 0/5 | 0/6 |
| RB | 5 | 0/13 | 1/13 | 0/13 | 1/9 | 0/7 | 0/6 | 0/9 |
| HU | 4 | 0/5 | 0/5 | 3/5 | 0/5 | 0/5 | 0/5 | 0/5 |
| TS | 3 | 1/10 | 0/10 | 0/10 | 0/10 | 0/10 | 0/4 | 0/10 |
| VL | 3 | 0/5 | 0/5 | 0/5 | 0/5 | 1/5 | 0/5 | 0/5 |
| JA | 3 | 0/11 | 1/11 | 3/11 | 0/11 | 2/11 | 0/11 | 0/11 |
| WE | 4 | 1/6 | 1/6 | 1/6 | 3/7 | 3/7 | 0/7 | 0/7 |
| GI | 4 | 0/4 | 1/4 | 0/4 | 0/4 | 0/4 | 0/4 | 0/4 |
| SE | 5 | 0/8 | 0/8 | 0/8 | 0/8 | 0/6 | 0/3 | 0/8 |
| KA | 5 | 0/1 | 0/1 | 0/1 | 0/1 | 0/1 | ND | 0/1 |
| HO | 3 | 1/6 | 0/5 | 1/6 | 0/6 | 0/6 | 0/6 | 0/6 |
| NY | 4 | 0/5 | 1/5 | 1/5 | 0/3 | 0/4 | 0/2 | 0/4 |
| JN | 3 | 0/10 | 5/10 | 0/10 | 0/10 | 1/10 | 0/10 | 0/10 |
| KO[f] | 3 | 1/10 | 0/10 | 0/10 | 0/10 | 2/10 | 0/10 | 0/10 |
| OE | 9 | ND | ND | ND | 0/6 | 0/6 | 0/6 | 0/6 |
| LO | 6 | ND | ND | ND | 0/3 | 0/3 | 0/2 | 0/3 |
| WI | 4 | ND | ND | ND | 0/1 | 1/1 | 0/1 | 0/3 |
| RR | 3 | ND | ND | ND | 1/8 | 0/8 | 0/8 | 0/8 |
| RY | 4 | ND | ND | ND | 0/3 | 0/4 | 0/3 | 0/4 |
| BE | 5 | ND | ND | ND | 0/10 | 0/10 | 0/10 | 0/10 |
| BU | 3 | ND | ND | ND | 1/6 | 0/6 | 0/6 | 0/6 |
| KR | 3 | ND | ND | ND | 1/4 | 0/4 | 0/4 | 0/4 |
| KW | 5 | ND | ND | ND | 0/10 | 0/10 | 0/10 | 0/10 |
| VR | 5 | ND | ND | ND | 1/6 | 0/6 | 0/6 | 0/6 |
| HU | 4 | ND | ND | ND | 1/4 | 0/3 | 0/3 | 0/4 |
| ME | 3 | ND | ND | ND | 0/5 | 1/5 | 0/5 | 0/5 |
| total negative[n] | | 19 | 41 | 29 | 97 | 16 | 140 | 165 |
| total positive[p] | | 77 | 48 | 62 | 55 | 131 | 1 | 0 |
| total sero-converted[s] | | 4 | 10 | 9 | 9 | 11 | 0 | 0 |
| total tested | | 100 | 99 | 100 | 161 | 158 | 141 | 165 |

| Farm | Interval in weeks | SNT EMCV | EMCVi | PEV2 | PEV2i | PEV7 | PEV7i | LA | IPMA LA |
|---|---|---|---|---|---|---|---|---|---|
| TH | 3 | 0/6 | 0/6 | 0/5 | 0/5 | 0/6 | 0/5 | 0/6 | 6/6 |
| RB | 5 | 1/7 | 1/9 | 0/6 | 2/6 | 1/8 | 0/6 | 0/13 | 7/9 |
| HU | 4 | ND | 0/5 | 0/5 | 0/5 | ND | 0/5 | 0/5 | 5/5 |
| TS | 3 | 0/10 | 0/10 | 0/7 | 0/4 | 0/10 | 0/7 | ND | 10/10 |
| VL | 3 | ND | ND | 1/5 | 0/5 | ND | 0/5 | ND | 5/5 |
| JA | 3 | 0/11 | 0/11 | 0/11 | 0/11 | 1/11 | 2/11 | 0/5 | 8/11 |
| WE | 4 | 1/7 | 1/6 | 1/6 | 1/7 | 1/7 | 1/7 | 0/7 | 7/7 |
| GI | 4 | 0/4 | 0/4 | 0/4 | 0/4 | 0/4 | 0/4 | 0/4 | 4/4 |
| SE | 5 | 0/8 | 0/8 | 0/6 | 1/8 | 0/8 | 1/5 | 0/8 | 6/8 |
| KA | 5 | 0/1 | 0/1 | 0/1 | 0/1 | 0/1 | 0/1 | 0/1 | 0/1 |
| HO | 3 | 0/6 | 0/6 | 0/6 | 0/6 | 0/6 | 0/6 | 0/6 | 4/6 |
| NY | 4 | 0/4 | 0/4 | 0/2 | 0/2 | 0/4 | 0/3 | 0/4 | 4/4 |
| JN | 3 | 0/10 | 0/10 | 1/10 | 0/9 | 0/10 | 0/10 | 0/10 | 5/10 |
| KO[f] | 3 | 0/10 | 0/10 | 2/10 | 2/10 | 1/10 | 3/10 | ND | 8/10 |
| OE | 9 | 0/6 | 0/6 | 1/6 | 1/5 | ND | 1/6 | ND | 4/6 |
| LO | 6 | 0/3 | 0/3 | 0/3 | 0/3 | ND | 0/3 | ND | 3/3 |
| WI | 4 | ND | ND | 0/1 | 0/1 | ND | 0/1 | ND | 0/3 |
| RR | 3 | 0/8 | 1/8 | 0/8 | 0/8 | 0/8 | 0/8 | ND | 8/8 |
| RY | 4 | 0/4 | ND | 0/4 | 0/1 | ND | 1/4 | ND | 1/4 |
| BE | 5 | ND | ND | 0/10 | 0/10 | ND | 1/10 | ND | 0/10 |
| BU | 3 | ND | ND | 0/6 | 0/6 | ND | 0/6 | ND | 6/6 |
| KR | 3 | ND | ND | 0/4 | 0/4 | ND | 0/4 | ND | 1/4 |
| KW | 5 | ND | ND | 0/10 | 0/10 | ND | 1/10 | ND | 10/10 |
| VR | 5 | ND | ND | 0/6 | 1/6 | ND | 0/6 | ND | 6/6 |
| HU | 4 | ND | ND | 0/3 | 0/4 | ND | 0/3 | ND | 3/4 |
| ME | 3 | ND | ND | 0/5 | 0/5 | ND | 0/5 | ND | 2/5 |
| total neg.[n] | | 15 | 29 | 0 | 0 | 2 | 1 | 69 | 15 |

TABLE 4-continued

Results of serology of paired field sera taken from sows suspected to have MSD. Sera were taken in the acute phase of the disease and 3-9 weeks later. Given is the number of sows which showed a fourfold or higher rise in titre/number of sows tested.

| | | | | | | | | |
|---|---|---|---|---|---|---|---|---|
| total pos.[P] | 88 | 74 | 144 | 138 | 90 | 136 | 0 | 27 |
| total sero-converted[s] | 2 | 3 | 6 | 8 | 4 | 10 | 0 | 123 |
| total tested | 105 | 107 | 150 | 146 | 96 | 147 | 69 | 165 |

The sera were tested in haemagglutinating inhibition (HAI) tests for the detection of antibody against haemagglutinating encephalitis virus (HEV), and swine influenza viruses H1N1 and H3N2, in enzyme-linked-immuno sorbent assays (ELISA) for the detection of antibody against the glycoprotein gI of pseudorabies virus (PRV), against porcine parvo virus (PPV), bovine viral diarrhea virus (BVDV), and hog cholera virus (HCV).
The sera were tested in serum neutralization tests (SNT) for the detection of neutralizing antibody directed against encephalomyocarditis virus (EMCV), the isolated (i) EMCV, porcine entero viruses (PEV) 2 and 7 and the PEV isolates (i), and against the Lelystad Agent (LA), and were tested in an immuno-peroxidase-monolayer-assay (IPMA) for the detection of antibody directed against the Lelystad Agent (LA).
[j]fattening pigs.
[t]time between sampling of the first and second serum.
[n]total number of pigs of which the first serum was negative in the test under study, and of which the second serum was also negative or showed a less than fourfold rise in titre. P total number of pigs of which the first serum was positive and of which the second serum showed a less than fourfold rise in titre.
[s]total number of pigs of which the second serum had a fourfold or higher titre than the first serum in the test under study.
ND = not done.

TABLE 5

Development of antibody directed against Lelystad Agent as measured by IPMA.

A contact pigs serum titres in IPMA
Weeks post contact:

| Pig | 0 | 2 | 3 | 4 | 5 |
|---|---|---|---|---|---|
| c 836 | 0 | 10 | 640 | 640 | 640 |
| c 837 | 0 | 10 | 640 | 640 | 640 |
| c 821 | 0 | 640 | 640 | 640 | 640 |
| c 823 | 0 | 160 | 2560 | 640 | 640 |
| c 829 | 0 | 160 | 640 | 10240 | 10240 |
| c 832 | 0 | 160 | 640 | 640 | 2560 |
| c 813 | 0 | 640 | 2560 | 2560 | 2560 |
| c 815 | 0 | 160 | 640 | 640 | 640 |

B blood inoculated pigs serum titres in IPMA
Weeks post inoculation:

| Pig | 0 | 2 | 3 | 4 | 6 |
|---|---|---|---|---|---|
| b 809 | 0 | 640 | 2560 | 2560 | 2560 |
| b 817 | 0 | 160 | 640 | 640 | 640 |
| b 818 | 0 | 160 | 640 | 640 | 640 |
| b 820 | 0 | 160 | 640 | 640 | 640 |
| b 822 | 0 | 640 | 2560 | 2560 | 10240 |
| b 826 | 0 | 640 | 640 | 640 | 10240 |
| b 830 | 0 | 640 | 640 | 640 | 2560 |
| b 834 | 0 | 160 | 640 | 2560 | 640 |

See Table 2 for description of the experiment. All pigs were bled at regular intervals and all sera were tested in an immuno-peroxidase-monolayer-assay (IPMA) for the detection of antibody directed against the Lelystad Agent (LA).

TABLE 6

Experimental reproduction of MSD.

| Sow | Length of gestation | No. of piglets at birth alive (Number Ab pos)[2] | dead | No. of deaths | LA[1] in piglets born died in week 1 dead | week 1 |
|---|---|---|---|---|---|---|
| 52 | 113 | 12 (5) | 3 (2) | 6 | 2 | 4 |
| 965 | 116 | 3 (0) | 9 (3) | 2 | 4 | |
| 997 | 114 | 9 (0) | 1 (0) | 0 | | |
| 1305 | 116 | 7 (0) | 2 (0) | 1 | | |
| 134 | 109 | 4 (4) | 7 (4) | 4 | 3 | |
| 941 | 117 | 7 | | 10 | | |
| 1056 | 113 | 7 (1) | 3 (0) | 4 | | |
| 1065 | 115 | 9 | | 2 | | |

[1]LA was isolated from lung, liver, spleen, kidney, or ascitic fluids.
[2]Antibodies directed against LA were detected in serum samples taken before the piglets had sucked, or were detected in ascitic fluids of piglets born dead.

TABLE 7

Reactivity in IPMA of a collection of field sera from Europe and North America tested with LA isolates from the Netherlands (NL1 and NL2), Germany (GE1 and GE2), and the United States (US1, US2 and US3).

| Sera from: | NL1 | NL2 | GE1 | GE2 | US1 | US2 | US3 |
|---|---|---|---|---|---|---|---|
| The Netherlands | | | | | | | |
| TH-187 | 3.5 | 3.5 | 2.5 | 3.5 | – | – | – |
| TO-36 | 3.5 | 3.0 | 2.5 | 3.0 | – | 1.0 | – |
| Germany | | | | | | | |
| BE-352 | 4.0 | 3.5 | 2.5 | 3.0 | – | 1.5 | – |
| BE-392 | 3.5 | 3.5 | 2.5 | 2.5 | 1.5 | 1.5 | 0.5 |
| NI-f2 | 2.5 | 1.5 | 2.0 | 2.5 | – | – | – |
| United Kingdom | | | | | | | |
| PA-141615 | 4.0 | 3.0 | 3.0 | 3.5 | – | – | – |
| PA-141617 | 4.0 | 3.5 | 3.0 | 3.5 | – | 2.5 | 2.0 |
| PA-142440 | 3.5 | 3.0 | 2.5 | 3.5 | – | 2.0 | 2.5 |
| Belgium | | | | | | | |
| PE-1960 | 4.5 | 4.5 | 3.0 | 4.0 | 1.5 | – | – |
| France | | | | | | | |

TABLE 7-continued

Reactivity in IPMA of a collection of field sera from Europe and North America tested with LA isolates from the Netherlands (NL1 and NL2), Germany (GE1 and GE2), and the United States (US1, US2 and US3).

| Sera from: | NL1 | NL2 | GE1 | GE2 | US1 | US2 | US3 |
|---|---|---|---|---|---|---|---|
| EA-2975 | 4.0 | 3.5 | 3.0 | 3.0 | 2.0 | – | – |
| EA-2985 | 3.5 | 3.0 | 3.0 | 2.5 | – | – | – |
| United States | | | | | | | |
| SL-441 | 3.5 | 1.5 | 2.5 | 2.5 | 3.5 | 3.5 | 3.0 |
| SL-451 | 3.0 | 2.0 | 2.5 | 2.5 | 3.5 | 4.5 | 4.0 |
| AL-RP9577 | 1.5 | – | – | 1.0 | 3.0 | 4.0 | 2.5 |
| AL-P10814/330.5 | 2.5 | – | – | 2.5 | 3.5 | 3.0 | |
| AL-4094A | – | – | – | – | 1.0 | 2.0 | 0.5 |
| AL-7525 | – | – | – | – | – | 1.0 | – |
| JC-MN41 | – | – | – | – | 1.0 | 3.5 | 1.0 |
| JC-MN44 | – | – | – | – | 2.0 | 3.5 | 2.0 |
| JC-MN45 | – | – | – | – | 2.0 | 3.5 | 2.5 |
| Canada | | | | | | | |
| RB-16 | 2.5 | – | 3.0 | 2.0 | 3.0 | 3.5 | – |
| RB-19 | 1.0 | – | 1.0 | – | 2.5 | 1.5 | – |
| RB-22 | 1.5 | – | 2.0 | 2.5 | 2.5 | 3.5 | – |
| RB-23 | – | – | – | – | – | 3.0 | – |

*t* = titre expressed as negative log;
– = negative

TABLE 8

Reactivity in IPMA of a collection of experimental sera raised against LA and SIRSV tested with LA isolates from the Netherlands (NL1 and NL2), Germany (GE1 and GE2), and the United States (US1, US2 and US3).

| Sera: | | NL1 | NL2 | GE1 | GE2 | US1 | US2 | US3 |
|---|---|---|---|---|---|---|---|---|
| anti-LA: | | | | | | | | |
| 21 | 14 dpi | 2.5*t* | 2.0 | 2.5 | 3.0 | 1.5 | 2.0 | 1.5 |
| | 28 dpi | 4.0 | 3.5 | 3.5 | 4.0 | – | 2.5 | 1.5 |
| | 42 dpi | 4.0 | 3.5 | 3.0 | 3.5 | 1.5 | 2.5 | 2.0 |
| 23 | 14 dpi | 3.0 | 2.0 | 2.5 | 3.0 | 1.0 | 2.0 | 1.0 |
| | 28 dpi | 3.5 | 3.5 | 3.5 | 4.0 | 1.5 | 2.0 | 2.0 |
| | 42 dpi | 4.0 | 4.0 | 3.0 | 4.0 | – | 2.5 | 2.5 |
| 25 | 14 dpi | 2.5 | 2.0 | 2.5 | 3.0 | 1.5 | 2.0 | 1.0 |
| | 28 dpi | 4.0 | 3.5 | 4.0 | 3.5 | – | 1.5 | 2.0 |
| | 42 dpi | 3.5 | 4.0 | 3.5 | 3.5 | 1.5 | 2.0 | 2.0 |
| 29 | 14 dpi | 3.5 | 3.5 | 3.0 | 3.5 | – | 2.0 | 1.5 |
| | 28 dpi | 3.5 | 3.5 | 3.0 | 3.5 | – | 2.5 | 2.0 |
| | 42 dpi | 4.0 | 3.5 | 3.5 | 4.0 | 1.5 | 2.5 | 2.5 |
| anti-SIRSV: | | | | | | | | |
| 2B | 20 dpi | – | – | – | – | 2.0 | 2.0 | – |
| | 36 dpi | – | – | – | – | 1.5 | 2.0 | – |
| | 63 dpi | – | – | – | – | 1.0 | 1.0 | – |
| 9G | 30 dpi | – | – | – | – | 2.5 | 3.0 | – |
| | 44 dpi | – | – | – | – | 2.5 | 3.5 | – |
| | 68 dpi | – | – | – | – | 2.0 | 3.5 | 1.5 |
| 16W | 25 dpi | – | – | – | – | 2.0 | 3.0 | – |
| | 40 dpi | – | – | – | – | 2.0 | 3.0 | – |
| | 64 dpi | – | – | – | – | 2.5 | 2.5 | 1.5 |
| 16Y | 36 dpi | – | – | – | – | 1.0 | 3.0 | 1.0 |
| | 64 dpi | – | – | – | – | 2.5 | 3.0 | – |

*t* = titer expressed as negative log;
– = negative

TABLE 9

Characteristics of the ORFs of Lelystad Virus.

| ORF | Nucleotides (first-last) | No. of amino acids | Calculated size of the unmodified peptide (kDa) | number of glycosylation sites |
|---|---|---|---|---|
| ORF1A | 212-7399 | 2396 | 260.0 | 3 (SEQ ID NO: 2) |
| ORF1B | 7384-11772 | 1463 | 161.8 | 3 (SEQ ID NO: 3) |
| ORF2 | 11786-12532 | 249 | 28.4 | 2 (SEQ ID NO: 4) |
| ORF3 | 12394-13188 | 265 | 30.6 | 7 (SEQ ID NO: 5) |
| | 12556-13188 | 211 | 24.5 | 4 |
| ORF4 | 12936-13484 | 183 | 20.0 | 4 (SEQ ID NO: 6) |
| | 12981-13484 | 168 | 18.4 | 4 |
| | 13068-13484 | 139 | 15.4 | 3 |
| ORF5 | 13484-14086 | 201 | 22.4 | 2 (SEQ ID NO: 7) |
| ORF6 | 14077-14595 | 173 | 18.9 | 2 (SEQ ID NO: 8) |
| ORF7 | 14588-14971 | 128 | 13.8 | 1 (SEQ ID NO: 9) |

REFERENCES

Boer, G. F. de, Back, W., and Osterhaus, A. D. M. E. (1990), An ELISA for detection of antibodies against influenza A nucleoprotein in human and various animal species, Arch. Virol. 115, 47-61.

Boursnell, M. E. G., Brown, T. D. K., and Binns, M. M. (1984), Sequence of the membrane protein gene from avian coronavirus IBV, Virus Res. 1, 303-314.

Boursnell, M. E. G., Brown, T. D. K., Foulds, I. J., Green, P. F., Tomley, F. M., and Binns, M. M. (1987), Completion of the sequence of the genome of the coronavirus avian infectious bronchitis virus, J. Gen. Virol. 68, 57-77.

Brakke, M. K. (1967), In: Methods in Virology, Volume II, pp. 93-117 (Edited by K. Maramorosch and H. Koprowski) New York, Academic Press.

Bredenbeek, P. J., Pachuk, C. J., Noten, J. F. H., Charité, J., Luytjes, W., Weiss, S. R., and Spaan, W. J. M. (1990), The primary structure and expression of the second open reading frame of the polymerase gene of coronavirus MHV-A59. Nucleic Acids Res. 18, 1825-1832.

Brenner, S., and Horne, R. W. (1959), A negative staining method for high resolution electron microscopy of viruses, Biochimica et Biophysica Acta 34, 103-110.

Brinton-Darnell, M., and Plagemann, P. G. (1975), Structure and chemical-physical characteristics of lactate dehydrogenase-elevating virus and its RNA, J. Virol. 16, 420-433.

Favaloro, J., Treisman, R. & Kamen, R. (1980), In: Methods in Enzymology, vol. 65, 718-749 (eds. Grossman, L. & Moldave, K.) Academic Press, New York.

Godeny, E. K., Speicher, D. W., and Brinton, M. A. (1990), Map location of lactate dehydrogenase-elevating virus (LDV) capsid protein (Vp1) gene, Virology, 177, 768-771.

Grist, N. R., Ross, C. A., and Bell, E. J. (1974), In: Diagnostic Methods in Clinical Virology, p. 120, Oxford, Blackwell Scientific Publications.

Gübler, U., and Hoffman, B. J. (1983), A simple and very efficient method for generating cDNA libraries, Gene 25, 263-269.

Hanahan, D. (1985), In: DNA Cloning I; A Practical Approach, Chapter 6, 109-135.

Hill, H. (1990), Overview and History of Mystery Swine Disease (Swine Infertility Respiratory Syndrome), In: Proceedings of the Mystery Swine Disease Committee Meeting, Oct. 6, 1990, Denver, Colo., Livestock Conservation Institute, Madison, Wis., USA.

Hirsch, J. G. & Fedorko, M. E. (1968), Ultrastructure of human leucocytes after simultanous fixation with glutaraldehyde and osmiumtetroxide and postfixation in uranylacetate, Journal of Cellular Biology 38, 615.

Horzinek, M. C., Maess, J., and Laufs, R. (1971), Studies on the substructure of togaviruses II. Analysis of equine arteritis, rubella, bovine viral diarrhea and hog cholera viruses, Arch. Gesamte Virusforsch. 33, 306-318.

Hyllseth, B. (1973), Structural proteins of equine arteritis virus, Arch. Gesamte Virusforsch. 40, 177-188.

Kasza, L., Shadduck, J. A., and Christoffinis, G. J. (1972), Establishment, viral susceptibility and biological characteristics of a swine kidney cell line SK-6, Res. Vet. Sci. 13, 46-51.

Loula, T. (1990), Clinical Presentation of Mystery Pig Disease in the breeding herd and suckling piglets, In: Proceedings of the Mystery Swine Disease Committee Meeting, Oct. 6, 1990, Denver, Colo., Livestock Conservation Institute, Madison, Wis., USA.

Masurel, N. (1976), Swine influenza virus and the recycling of influenza A viruses in man, Lancet ii, 244-247.

Mazancourt, A. de, Waxham. M. N., Nicholas, J. C., & Wolinsky, J. S. (1986), Antibody response to the rubella virus structural proteins in infants with the congenital rubella syndrome. J. Med. Virol. 19, 111-122.

Mengeling, W. L., and Lager, K. M. (1990), Mystery Pig Disease: Evidence and considerations for its etiology, In: Proceedings of the Mystery Swine Disease Committee Meeting, Oct. 6, 1990, Denver, Colo., Livestock Conservation Institute, Madison, Wis., USA.

Moormann, R. J. M., and Hulst, M. M. (1988), Hog cholera virus: identification and characterization of the viral RNA and virus-specific RNA synthesized in infected swine kidney cells, Virus Res. 11, 281-291.

Moormann, R. J. M., Warmerdam, P. A. M., van der Meer, B., Schaaper, W. M. M., Wensvoort, G., and Hulst, M. M. (1990), Molecular cloning and nucleotide sequence of hog cholera virus strain Brescia and mapping of the genomic region encoding envelope protein E1, Virology, 177, 184-198.

Oirschot, J. T. van, Houwers, D. J., Rziha, H. J., and Moonen, P. J. L. M. (1988), Development of an ELISA for detection of antibodies to glycoprotein I of Aujeszky's disease virus: a method for the serological differentiation between infected and vaccinated pigs, J. Virol. Meth. 22, 191-206.

Pearson, W. R., and Lipman, D. J. (1988), Improved tools for biological sequence comparison. Proc. Natl. Acad. Sci. USA 85, 2444-2448.

Reed, L. J., and Muench, H. (1938), A simple method of estimating fifty percent endpoints, Am. J. Hyg. 27, 493-497.

Rottier, P. J. M., Welling, G. W., Welling-Wester, S., Niesters, H. G. M., Lenstra, J. M., and van der Zeijst, B. A. M. (1986), Predicted membrane topology of the coronavirus protein E1. Biochemistry 25, 1335-1339.

Sambrook, J., Fritsch, E. F., and Maniatis, T. (1989), Molecular Cloning, A Laboratory Manual. Cold Spring Harbor Lab., Cold Spring Harbor, N.Y.

Sethna, P. B., Hung, S-L., and Brian, D. A. (1989), Coronavirus subgenomic minus-strand RNAs and the potential for mRNA replicons, Proc. Natl. Acad. Sci. USA, 86, 5626-5630.

Setzer, D. R., McGrogan, M., Nunberg, J. H. & Schimke, R. T. (1980), Size heterogeneity in the 3'-end of the dehydrofolate reductase messenger RNA's in mouse cells, Cell 22, 361-370.

Snijder, E. J., den Boon, J. A., Bredenbeek, P. J., Horzinek, M. C., Rijnbrand, R., and Spaan, W. J. M. (1990a), The carboxyl-terminal part of the putative Berne virus polymerase is expressed by ribosomal frameshifting and contains sequence motifs which indicate that toro- and coronaviruses are evolutionary related, Nucleic Acids Res. 18, 4535-4542.

Snijder, E. J., Horzinek, M. C., and Spaan, W. J. M. (1990b), A 3'-coterminal nested set of independently transcribed messenger RNAs is generated during Berne virus replication. J. Virol. 64, 355-363.

Spaan, W. J. M., Cavanagh, D., and Horzinek, M. C. (1988), Coronaviruses: structure and genome expression. J. Gen. Virol. 69, 2939-2952.

Strauss, W. M. (1987), Preparation of genomic DNA from mammalian tissue, In: Current protocols in molecular biology (eds. Ausubel F. M., et al.) 2.2.1 John Wiley & Sons, New York.

Terpstra, C. (1978), Detection of Border disease antigen in tissues of affected sheep and in cell cultures by immunofluorescence, Res. Vet. Sci. 25, 350-355.

Venable, J. H. & Coggeshall, R. (1965), A simplified lead citrate stain for use in electronmicroscopy, Journal of Cellular Biology 25, 407.

Vries, A. A. F. de, Chirnside, E. D., Bredenbeek, P. J., Gravestein, L. A., Horzinek, M. C., and Spaan, W. J. M. (1990), All subgenomic mRNAs of equine arteritis virus contain a common leader sequence, Nucleic Acids Res. 18, 3241-3247.

Wensvoort, G., and Terpstra, C. (1988), Bovine viral diarrhea infections in piglets from sows vaccinated against swine fever with contaminated vaccine, Res. Vet. Sci. 45, 143-148.

Wensvoort, G., Terpstra, C., and Bloemraad, M. (1988), An enzyme immunoassay, employing monoclonal antibodies and detecting specifically antibodies against classical swine fever virus, Vet. Microbiol. 17, 129-140.

Wensvoort, G., Terpstra, C., Boonsta, J., Bloemraad, M., and Zaane, D. van (1986), Production of monoclonal antibodies against swine fever virus and their use in laboratory diagnosis, Vet. Microbiol. 12, 101-108.

Wensvoort, G., Terpstra. C., and Kluyver, E. P. de (1989), Characterization of porcine and some ruminant pestiviruses by cross-neutralization, Vet. Microbiol. 20, 291-306.

Westenbrink, F., Middel. W. G. J., Straver, P., and Leeuw, P. W. de (1986), A blocking enzyme-linked immunosorbent assay (ELISA) for bovine virus diarrhea virus serology, J. Vet. Med. B33, 354-361.

Westenbrink, F., Veldhuis, M. A., and Brinkhof, J. M. A. (1989), An enzyme-linked immunosorbent assay for detection of antibodies to porcine parvo virus, J. Virol. Meth. 23, 169-178.

Zeijst. B. A. M. van der, Horzinek, M. C., and Moennig, V. (1975), The genome of equine arteritis virus, Virology, 68, 418-425.

What is claimed is:

1. A method of producing an immunogenic composition, the method comprising:
    introducing a purified preparation containing a polynucleotide encoding at least one polypeptide encoded by one or more open reading frames (ORFs) of ORFs 1-7 of a mystery swine disease virus wherein the polypeptide is one of more of the polypeptides selected from the group consisting of SEQ ID NO: 2; SEQ ID NO:3; SEQ ID NO:4; SEQ ID NO: 5; SEQ ID NO:6; SEQ ID NO:7; SEQ ID NO:8 and SEQ ID NO:9, into a suitable host cell,
    culturing said suitable host cell; and
    isolating one of the following therefrom; a suitable host cell containing said polypeptide; viral protein; or viral polynucleic acid.

2. The method according to claim 1, further comprising isolating at least one of a cultured host cell and a polypeptide encoded by said polynucleotide.

3. The method according to claim 1, wherein introducing a purified preparation containing a polypeptide encoding at least one polypeptide encoded by one or more open reading frame (ORFS) of ORFS 1-7 of a mystery swine disease virus, into a suitable host cell comprises infecting the suitable host cell with a virus comprising a polynucleotide that encodes said polypeptide.

4. The method according to claim 1, wherein the mystery swine disease virus is characterized as being specifically reactive with serum antibodies of a sow, said serum antibodies obtained by intranasally inoculating a specific pathogen free sow with two milliliters of the virus identified as deposit number 11 102, deposited Jun. 5, 1991 with the Insitut Pasteur, Paris, France (at passage level 3, titer 1 04,8TCID.sub.so/milliliter) and collecting serum antibodies from the thus inoculated sow after 25 to 33 days.

5. The method according claim 3, further comprising isolating at least one of a cultured host cell and a polypeptide encoded by said polynucleotide.

6. The method according to claim 4 wherein said polynucleotide comprises a sequence selected from the group consisting of nucleotides 212-7399 of SEQ ID NO:1; 7384-11772 of SEQ ID NO:1; 11786-12532 of SEQ ID NO:1; 12394-13188 of SEQ ID NO:1; 12556-13188 of SEQ ID NO:1; 12936-13484 of SEQ ID NO:1; 12981-13484 of SEQ ID NO:1; 13068-13484 of SEQ ID NO:1; 13484-14086 of SEQ ID NO:1; 14077-14595 of SEQ ID NO:1; and 14588-14971 of SEQ ID NO:1.

7. The method of claim 1, wherein said method comprises isolating one or more polynucleotides having a sequence selected from the group consisting of selected from the group consisting of nucleotides 212-7399 of SEQ ID NO:1; 7384-11772 of SEQ ID NO:1; 11786-12532 of SEQ ID NO:1; 12394-13188 of SEQ ID NO:1; 12556-13188 of SEQ ID NO:1; 12936-13484 of SEQ ID NO:1; 12981-13484 of SEQ ID NO:1; 13068-13484 of SEQ ID NO:1; 13484-14086 of SEQ ID NO:1; 14077-14595 of SEQ ID NO:1; and 14588-14971 of SEQ ID NO:1.

8. The method of claim 1, wherein said method comprises isolating one or more of ORF polypeptides selected from the group consisting of the group consisting of SEQ ID NO: 2; SEQ ID NO:3; SEQ ID NO:4; SEQ ID NO: 5; SEQ ID NO:6; SEQ ID NO:7; SEQ ID NO:8 and SEQ ID NO:9.

9. A method of producing an immunogenic composition, the method comprising:
    introducing a purified preparation containing a polynucleotide encoding at least one polypeptide encoded by one or more open reading frames (ORFS) of a mystery swine disease virus that has nucleotide sequence of SEQ ID NO:1, into a suitable host cell,
    culturing said suitable host cell; and
    isolating one of the following therefrom; a suitable host cell containing said polypeptide; viral protein; or viral polynucleic acid.

10. The method of claim 9, wherein said method comprises encoding one or more of ORF polypeptides selected from the group consisting of the group consisting of SEQ ID NO: 2; SEQ ID NO:3; SEQ ID NO:4; SEQ ID NO: 5; SEQ ID NO:6; SEQ ID NO:7; SEQ ID NO:8 and SEQ ID NO:9.

11. The method of claim 9, wherein said method comprises isolating one or more polynucleotides having a sequence selected from the group consisting of selected from the group consisting of nucleotides 212-7399 of SEQ ID NO:1; 7384-11772 of SEQ ID NO:1; 11786-12532 of SEQ ID NO:1; 12394-13188 of SEQ ID NO:1; 12556-13188 of SEQ ID NO:1; 12936-13484 of SEQ ID NO:1; 12981-13484 of SEQ ID NO:1; 13068-13484 of SEQ ID NO:1; 13484-14086 of SEQ ID NO:1; 14077-14595 of SEQ ID NO:1; and 14588-14971 of SEQ ID NO:1.

12. The method of claim 9, wherein said method comprises isolating one or more of ORF polypeptides selected from the group consisting of the group consisting of SEQ ID NO: 2; SEQ ID NO:3; SEQ ID NO:4; SEQ ID NO: 5; SEQ ID NO:6; SEQ ID NO:7; SEQ ID NO:8 and SEQ ID NO:9.

* * * * *

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 15108 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 212..7399
        (D) OTHER INFORMATION:

(ix) FEATURE:
        (A) NAME/KEY: CDS
        (B) LOCATION: 7384..11772
        (D) OTHER INFORMATION:

(ix) FEATURE:
        (A) NAME/KEY: CDS
        (B) LOCATION: 11786..12532
        (D) OTHER INFORMATION:

(ix) FEATURE:
        (A) NAME/KEY: CDS
        (B) LOCATION: 12394..13188
        (D) OTHER INFORMATION:

(ix) FEATURE:
        (A) NAME/KEY: CDS
        (B) LOCATION: 12936..13484
        (D) OTHER INFORMATION:

(ix) FEATURE:
        (A) NAME/KEY: CDS
        (B) LOCATION: 13484..14086
        (D) OTHER INFORMATION:

(ix) FEATURE:
        (A) NAME/KEY: CDS
        (B) LOCATION: 14077..14595
        (D) OTHER INFORMATION:

(ix) FEATURE:
        (A) NAME/KEY: CDS
        (B) LOCATION: 14588..14971
        (D) OTHER INFORMATION:

(xi) SEQUENCE DESCRIPTION: SEQ ID NO: 1:

```
GGGTATTCCC CCTACATACA CGACACTTCT AGTGTTTGTG TACCTTGGAG GCGTGGGTAC        60

AGCCCCGCCC CACCCCTTGG CCCCTGTTCT AGCCCAACAG GTATCCTTCT CTCTCGGGGC       120

GAGTGCGCCG CCTGCTGCTC CCTTGCAGCG GGAAGGACCT CCCGAGTATT TCCGGAGAGC       180

ACCTGCTTTA CGGGATCTCC ACCCTTTAAC C ATGTCTGGGA CGTTCTCCCG                231

GTGCATGTGC ACCCCGGCTG CCCGGGTATT TTGGAACGCC GGCCAAGTCT TTTGCACACG       291

GTGTCTCAGT GCGCGGTCTC TTCTCTCTCC AGAGCTTCAG GACACTGACC TCGGTGCAGT       351

TGGCTTGTTT TACAAGCCTA GGGACAAGCT TCACTGGAAA GTCCCTATCG GCATCCCTCA       411

GGTGGAATGT ACTCCATCCG GGTGCTGTTG GCTCTCAGCT GTTTTCCCTT TGGCGCGTAT       471

GACCTCCGGC AATCACAACT TCCTCCAACG ACTTGTGAAG GTTGCTGATG TTTTGTACCG       531

TGACGGTTGC TTGGCACCTC GACACCTTCG TGAACTCCAA GTTACGAGC GCGGCTGCAA        591

CTGGTACCCG ATCACGGGGC CCGTGCCCGG GATGGGTTTG TTTGCGAACT CCATGCACGT       651

ATCCGACCAG CCGTTCCCTG GTGCCACCCA TGTGTTGACT AACTCGCCTT TGCCTCAACA       711

GGCTTGTCGG CAGCCGTTCT GTCCATTTGA GGAGGCTCAT TCTAGCGTGT ACAGGTGGAA       771

GAAATTTGTG GTTTTCACGG ACTCCTCCCT CAACGGTCGA TCTCGCATGA TGTGGACGCC       831

GGAATCCGAT GATTCAGCCG CCCTGGAGGT ACTACCGCCT GAGTTAGAAC GTCAGGTCGA       891
```

```
AATCCTCATT CGGAGTTTTC CTGCTCATCA CCCTGTCGAC CTGGCCGACT GGGAGCTCAC    951
TGAGTCCCCT GAGAACGGTT TTTCCTTCAA CACGTCTCAT TCTTGCGGTC ACCTTGTCCA   1011
GAACCCCGAC GTGTTTGATG GCAAGTGCTG GCTCTCCTGC TTTTTGGGCC AGTCGGTCGA   1071
AGTGCGCTGC CATGAGGAAC ATCTAGCTGA CGCCTTCGGT TACCAAACCA AGTGGGCGT    1131
GCATGGTAAG TACCTCCAGC GCAGGCTTCA AGTTCGCGGC ATTCGTGCTG TAGTCGATCC   1191
TGATGGTCCC ATTCACGTTG AAGCGCTGTC TTGCCCCCAG TCTTGGATCA GGCACCTGAC   1251
TCTGGATGAT GATGTCACCC CAGGATTCGT TCGCCTGACA TCCCTTCGCA TTGTGCCGAA   1311
CACAGAGCCT ACCACTTCCC GGATCTTTCG GTTTGGAGCG CATAAGTGGT ATGGCGCTGC   1371
CGGCAAACGG GCTCGTGCTA AGCGTGCCGC TAAAAGTGAG AAGGATTCGG CTCCCACCCC   1431
CAAGGTTGCC CTGCCGGTCC CCACCTGTGG AATTACCACC TACTCTCCAC CGACAGACGG   1491
GTCTTGTGGT TGGCATGTCC TTGCCGCCAT AATGAACCGG ATGATAAATG GTGACTTCAC   1551
GTCCCCTCTG ACTCAGTACA ACAGACCAGA GGATGATTGG GCTTCTGATT ATGATCTTGT   1611
TCAGGCGATT CAATGTCTAC GACTGCCTGC TACCGTGGTT CGGAATCGCG CCTGTCCTAA   1671
CGCCAAGTAC CTTATAAAAC TTAACGGAGT TCACTGGGAG GTAGAGGTGA GGTCTGGAAT   1731
GGCTCCTCGC TCCCTTTCTC GTGAATGTGT GGTTGGCGTT TGCTCTGAAG CTGTGTCGC    1791
ACCGCCTTAT CCAGCAGACG GGCTACCTAA ACGTGCACTC GAGGCCTTGG CGTCTGCTTA   1851
CAGACTACCC TCCGATTGTG TTAGCTCTGG TATTGCTGAC TTTCTTGCTA ATCCACCTCC   1911
TCAGGAATTC TGGACCCTCG ACAAAATGTT GACCTCCCCG TCACCAGAGC GGTCCGGCTT   1971
CTCTAGTTTG TATAAATTAC TATTAGAGGT TGTTCCGCAA AAATGCGGTG CCACGGAAGG   2031
GGCTTTCATC TATGCTGTTG AGAGGATGTT GAAGGATTGT CCGAGCTCCA AACAGGCCAT   2091
GGCCCTTCTG GCAAAAATTA AAGTTCCATC CTCAAAGGCC CCGTCTGTGT CCCTGGACGA   2151
GTGTTTCCCT ACGGATGTTT TAGCCGACTT CGAGCCAGCA TCTCAGGAAA GGCCCCAAAG   2211
TTCCGGCGCT GCTGTTGTCC TGTGTTCACC GGATGCAAAA GAGTTCGAGG AAGCAGCCCC   2271
RGAAGAAGTT CAAGAGAGTG GCCACAAGGC CGTCCACTCT GCACTCCTTG CCAGGGTCC    2331
TAACAATGAG CAGGTACAGG TGGTTGCCGG TGAGCAACTG AAGCTCGGCG GTTGTGGTTT   2391
GGCAGTCGGG AATGCTCATG AAGGTGCTCT GGTCTCAGCT GGTCTAATTA ACCTGGTAGG   2451
CGGGAATTTG TCCCCCTCAG ACCCCATGAA AGAAAACATG CTCAATAGCC GGGAAGACGA   2511
ACCACTGGAT TTGTCCCAAC CAGCACCAGC TTCCACAACG ACCCTTGTGA GAGAGCAAAC   2571
ACCCGACAAC CCAGGTTCTG ATGCCGGTGC CCTCCCCGTC ACCGTTCGAG AATTTGTCCC   2631
GACGGGGCCT ATACTCTGTC ATGTTGAGCA CTGCGGCACG GAGTCGGGCG ACAGCAGTTC   2691
GCCTTTGGAT CTATCTGATG CGCAAACCCT GGACCAGCCT TTAAATCTAT CCCTGGCCGC   2751
TTGGCCAGTG AGGGCCACCG CGTCTGACCC TGGCTGGGTC CACGGTAGGC GCGAGCCTGT   2811
CTTTGTAAAG CCTCGAAATG CTTTCTCTGA TGGCGATTCA GCCCTTCAGT TCGGGGAGCT   2871
TTCTGAATCC AGCTCTGTCA TCGAGTTTGA CCGGACAAAA GATGCTCCGG TGGTTGACGC   2931
CCCTGTCGAC TTGACGACTT CGAACGAGGC CCTCTCTGTA GTCGATCCTT TCGAATTTGC   2991
CGAACTCAAG CGCCCGCGTT TCTCCGCACA AGCCTTAATT GACCGAGGCG GTCCACTTGC   3051
CGATGTCCAT GCAAAAATAA AGAACGGGGT ATATGAACAG TGCCTCCAAG CTTGTGAGCC   3111
CGGTAGTCGT GCAACCCCAG CCACCAGGGA GTGGCTCGAC AAAATGTGGG ATAGGGTGGA   3171
CATGAAAACT TGGCGCTGCA CCTCGCAGTT CCAAGCTGGT CGCATTCTTG CGTCCCTCAA   3231
ATTCCTCCCT GACATGATTC AAGACACACC GCCTCCTGTT CCCAGGAAGA ACCGAGCTAG   3291
```

```
TGACAATGCC GGCCTGAAGC AACTGGTGGC ACAGTGGGAT AGGAAATTGA GTGTGACCCC   3351
CCCCCCAAAA CCGGTTGGGC CAGTGCTTGA CCAGATCGTC CCTCCGCCTA CGGATATCCA   3411
GCAAGAAGAT GTCACCCCCT CCGATGGGCC ACCCCATGCG CCGGATTTTC CTAGTCGAGT   3471
GAGCACGGGC GGGAGTTGGA AAGGCCTTAT GCTTTCCGGC ACCCGTCTCG CGGGGTCTAT   3531
CAGCCAGCGC CTTATGACAT GGGTTTTTGA AGTTTTCTCC CACCTCCCAG CTTTTATGCT   3591
CACACTTTTC TCGCCGCGGG GCTCTATGGC TCCAGGTGAT TGGTTGTTTG CAGGTGTCGT   3651
TTTACTTGCT CTCTTGCTCT GTCGTTCTTA CCCGATACTC GGATGCCTTC CCTTATTGGG   3711
TGTCTTTTCT GGTTCTTTGC GGCGTGTTCG TCTGGGTGTT TTTGGTTCTT GGATGGCTTT   3771
TGCTGTATTT TTATTCTCGA CTCCATCCAA CCCAGTCGGT TCTTCTTGTG ACCACGATTC   3831
GCCGGAGTGT CATGCTGAGC TTTTGGCTCT TGAGCAGCGC CAACTTTGGG AACCTGTGCG   3891
CGGCCTTGTG GTCGGCCCCT CAGGCCTCTT ATGTGTCATT CTTGGCAAGT TACTCGGTGG   3951
GTCACGTTAT CTCTGGCATG TTCTCCTACG TTTATGCATG CTTGCAGATT TGGCCCTTTC   4011
TCTTGTTTAT GTGGTGTCCC AGGGGCGTTG TCACAAGTGT TGGGGAAAGT GTATAAGGAC   4071
AGCTCCTGCG GAGGTGGCTC TTAATGTATT TCCTTTCTCG CGCGCCACCC GTGTCTCTCT   4131
TGTATCCTTG TGTGATCGAT TCCAAACGCC AAAAGGGGTT GATCCTGTGC ACTTGGCAAC   4191
GGGTTGGCGC GGGTGCTGGC GTGGTGAGAG CCCCATCCAT CAACCACACC AAAAGCCCAT   4251
AGCTTATGCC AATTTGGATG AAAAGAAAAT GTCTGCCCAA ACGGTGGTTG CTGTCCCATA   4311
CGATCCCAGT CAGGCTATCA AATGCCTGAA AGTTCTGCAG GCGGGAGGGG CCATCGTGGA   4371
CCAGCCTACA CCTGAGGTCG TTCGTGTGTC CGAGATCCCC TTCTCAGCCC CATTTTTCCC   4431
AAAAGTTCCA GTCAACCCAG ATTGCAGGGT TGTGGTAGAT TCGGACACTT TTGTGGCTGC   4491
GGTTCGCTGC GGTTACTCGA CAGCACAACT GGTYCTGGGC CGGGGCAACT TGCCAAGTT   4551
AAATCAGACC CCCCCCAGGA ACTCTATCTC CACCAAAACG ACTGGTGGGG CCTCTTACAC   4611
CCTTGCTGTG GCTCAAGTGT CTGCGTGGAC TCTTGTTCAT TTCATCCTCG GTCTTTGGTT   4671
CACATCACCT CAAGTGTGTG GCCGAGGAAC CGCTGACCCA TGGTGTTCAA ATCCTTTTTC   4731
ATATCCTACC TATGGCCCCG GAGTTGTGTG CTCCTCTCGA CTTTGTGTGT CTGCCGACGG   4791
GGTCACCCTG CCATTGTTCT CAGCCGTGGC ACAACTCTCC GGTAGAGAGG TGGGGATTTT   4851
TATTTTGGTG CTCGTCTCCT TGACTGCTTT GGCCCACCGC ATGGCTCTTA AGGCAGACAT   4911
GTTAGTGGTC TTTTCGGCTT TTTGTGCTTA CGCCTGGCCC ATGAGCTCCT GGTTAATCTG   4971
CTTCTTTCCT ATACTCTTGA AGTGGGTTAC CCTTCACCCT CTTACTATGC TTTGGGTGCA   5031
CTCATTCTTG GTGTTTTGTC TGCCAGCAGC CGGCATCCTC TCACTAGGGA TAACTGGCCT   5091
TCTTTGGGCA ATTGGCCGCT TTACCCAGGT TGCCGGAATT ATTACACCTT ATGACATCCA   5151
CCAGTACACC TCTGGGCCAC GTGGTGCAGC TGCTGTGGCC ACAGCCCCAG AAGGCACTTA   5211
TATGGCCGCC GTCCGGAGAG CTGCTTTAAC TGGGCGAACT TTAATCTTCA CCCCGTCTGC   5271
AGTTGGATCC CTTCTCGAAG GTGCTTTCAG GACTCATAAA CCCTGCCTTA ACACCGTGAA   5331
TGTTGTAGGC TCTTCCCTTG GTTCCGGAGG GGTTTTCACC ATTGATGGCA GAAGAACTGT   5391
CGTCACTGCT GCCCATGTGT TGAACGGCGA CACAGCTAGA GTCACCGGCG ACTCCTACAA   5451
CCGCATGCAC ACTTTCAAGA CCAATGGTGA TTATGCCTGG TCCCATGCTG ATGACTGGCA   5511
GGGCGTTGCC CCTGTGGTCA AGGTTGCGAA GGGGTACCGC GGTCGTGCCT ACTGGCAAAC   5571
ATCAACTGGT GTCGAACCCG GTATCATTGG GGAAGGGTTC GCCTTCTGTT TTACTAACTG   5631
CGGCGATTCG GGGTCACCCG TCATCTCAGA ATCTGGTGAT CTTATTGGAA TCCACACCGG   5691
```

```
TTCAAACAAA CTTGGTTCTG GTCTTGTGAC AACCCCTGAA GGGGAGACCT GCACCATCAA    5751

AGAAACCAAG CTCTCTGACC TTTCCAGACA TTTTGCAGGC CCAAGCGTTC CTCTTGGGGA    5811

CATTAAATTG AGTCCGGCCA TCATCCCTGA TGTAACATCC ATTCCGAGTG ACTTGGCATC    5871

GCTCCTAGCC TCCGTCCCTG TAGTGGAAGG CGGCCTCTCG ACCGTTCAAC TTTTGTGTGT    5931

CTTTTTCCTT CTCTGGCGCA TGATGGGCCA TGCCTGGACA CCCATTGTTG CCGTGGGCTT    5991

CTTTTTGCTG AATGAAATTC TTCCAGCAGT TTTGGTCCGA GCCGTGTTTT CTTTTGCACT    6051

CTTTGTGCTT GCATGGGCCA CCCCCTGGTC TGCACAGGTG TTGATGATTA GACTCCTCAC    6111

GGCATCTCTC AACCGCAACA AGCTTTCTCT GGCGTTCTAC GCACTCGGGG GTGTCGTCGG    6171

TTTGGCAGCT GAAATCGGGA CTTTTGCTGG CAGATTGTCT GAATTGTCTC AAGCTCTTTC    6231

GACATACTGC TTCTTACCTA GGGTCCTTGC TATGACCAGT TGTGTTCCCA CCATCATCAT    6291

TGGTGGACTC CATACCCTCG GTGTGATTCT GTGGTTRTTC AAATACCGGT GCCTCCACAA    6351

CATGCTGGTT GGTGATGGGA GTTTTTCAAG CGCCTTCTTC CTACGGTATT TTGCAGAGGG    6411

TAATCTCAGA AAAGGTGTTT CACAGTCCTG TGGCATGAAT AACGAGTCCC TAACGGCTGC    6471

TTTAGCTTGC AAGTTGTCAC AGGCTGACCT TGATTTTTTG TCCAGCTTAA CGAACTTCAA    6531

GTGCTTTGTA TCTGCTTCAA ACATGAAAAA TGCTGCCGGC CAGTACATTG AAGCAGCGTA    6591

TGCCAAGGCC CTGCGCCAAG AGTTGGCCTC TCTAGTTCAG ATTGACAAAA TGAAAGGAGT    6651

TTTGTCCAAG CTCGAGGCCT TGCTGAAAAC AGCCACCCCG TCCCTTGACA TAGGTGACGT    6711

GATTGTTCTG CTTGGGCAAC ATCCTCACGG ATCCATCCTC GATATTAATG TGGGGACTGA    6771

AAGGAAAACT GTGTCCGTGC AAGAGACCCG GAGCCTAGGC GGCTCCAAAT TCAGTGTTTG    6831

TACTGTCGTG TCCAACACAC CCGTGGACGC CTTACCGGC ATCCCACTCC AGACACCAAC     6891

CCCTCTTTTT GAGAATGGTC CGCGTCATCG CAGCGAGGAA GACGATCTTA AGTCGAGAG     6951

GATGAAGAAA CACTGTGTAT CCCTCGGCTT CCACAACATC AATGGCAAAG TTTACTGCAA    7011

AATTTGGGAC AAGTCTACCG GTGACACCTT TTACACGGAT GATTCCCGGT ACACCCAAGA    7071

CCATGCTTTT CAGGACAGGT CAGCCGACTA CAGAGACAGG GACTATGAGG GTGTGCAAAC    7131

CACCCCCCAA CAGGGATTTG ATCCAAAGTC TGAAACCCCT GTTGGCACTG TTGTGATCGG    7191

CGGTATTACG TATAACAGGT ATCTGATCAA AGGTAAGGAG GTTCTGGTCC CCAAGCCTGA    7251

CAACTGCCTT GAAGCTGCCA AGCTGTCCCT TGAGCAAGCT CTCGCTGGGA TGGGCCAAAC    7311

TTGCGACCTT ACAGCTGCCG AGGTGGAAAA GCTAAAGCGC ATCATTAGTC AACTCCAAGG    7371

TTTGACCACT GAACAGGCTT TAAACTGT TAGCCGCCAG CGGCTTGACC CGCTGTGGCC      7429

GCGGCGGCCT AGTTGTGACT GAAACGGCGG TAAAAATTAT AAAATACCAC AGCAGAACTT    7489

TCACCTTAGG CCCTTTAGAC CTAAAAGTCA CTTCCGAGGT GGAGGTAAAG AAATCAACTG    7549

AGCAGGGCCA CGCTGTTGTG GCAAACTTAT GTTCCGGTGT CATCTTGATG AGACCTCACC    7609

CACCGTCCCT TGTCGACGTT CTTCTGAAAC CCGGACTTGA CACAATACCC GGCATTCAAC    7669

CAGGGCATGG GGCCGGGAAT ATGGGCGTGG ACGGTTCTAT TTGGGATTTT GAAACCGCAC    7729

CCACAAAGGC AGAACTCGAG TTATCCAAGC AAATAATCCA AGCATGTGAA GTTAGGCGCG    7789

GGGACGCCCC GAACCTCCAA CTCCCTTACA AGCTCTATCC TGTTAGGGGG GATCCTGAGC    7849

GGCATAAAGG CCGCCTTATC AATACCAGGT TTGGAGATTT ACCTTACAAA ACTCCTCAAG    7909

ACACCAAGTC CGCAATCCAC GCGGCTTGTT GCCTGCACCC CAACGGGGCC CCCGTGTCTG    7969

ATGGTAAATC CACACTAGGT ACCACTCTTC AACATGGTTT CGAGCTTTAT GTCCCTACTG    8029

TGCCCTATAG TGTCATGGAG TACCTTGATT CACGCCCTGA CACCCCTTTT ATGTGTACTA    8089
```

```
AACATGGCAC TTCCAAGGCT GCTGCAGAGG ACCTCCAAAA ATACGACCTA TCCACCCAAG    8149

GATTTGTCCT GCCTGGGGTC CTACGCCTAG TACGCAGATT CATCTTTGGC CATATTGGTA    8209

AGGCGCCGCC ATTGTTCCTC CCATCAACCT ATCCCGCCAA GAACTCTATG GCAGGGATCA    8269

ATGGCCAGAG GTTCCCAACA AAGGACGTTC AGAGCATACC TGAAATTGAT GAAATGTGTG    8329

CCCGCGCTGT CAAGGAGAAT TGGCAAACTG TGACACCTTG CACCCTCAAG AAACAGTACT    8389

GTTCCAAGCC CAAAACCAGG ACCATCCTGG GCACCAACAA CTTTATTGCC TTGGCTCACA    8449

GATCGGCGCT CAGTGGTGTC ACCCAGGCAT TCATGAAGAA GGCTTGGAAG TCCCCAATTG    8509

CCTTGGGGAA AAACAAATTC AAGGAGCTGC ATTGCACTGT CGCCGGCAGG TGTCTTGAGG    8569

CCGACTTGGC CTCCTGTGAC CGCAGCACCC CCGCCATTGT AAGATGGTTT GTTGCCAACC    8629

TCCTGTATGA ACTTGCAGGA TGTGAAGAGT ACTTGCCTAG CTATGTGCTT AATTGCTGCC    8689

ATGACCTCGT GGCAACACAG GATGGTGCCT TCACAAAACG CGGTGGCCTG TCGTCCGGGG    8749

ACCCCGTCAC CAGTGTGTCC AACACCGTAT ATTCACTGGT AATTTATGCC CAGCACATGG    8809

TATTGTCGGC CTTGAAAATG GGTCATGAAA TTGGTCTTAA GTTCCTCGAG GAACAGCTCA    8869

AGTTCGAGGA CCTCCTTGAA ATTCAGCCTA TGTTGGTATA CTCTGATGAT CTTGTCTTGT    8929

ACGCTGAAAG ACCCCACMTTT CCCAATTACC ACTGGTGGGT CGAGCACCTT GACCTGATGC    8989

TGGGTTTCAG AACGGACCCA AGAAAAACCG TCATAACTGA TAAACCCAGC TTCCTCGGCT    9049

GCAGAATTGA GGCAGGGCGA CAGCTAGTCC CCAATCGCGA CCGCATCCTG GCTGCTCTTG    9109

CATATCACAT GAAGGCGCAG AACGCCTCAG AGTATTATGC GTCTGCTGCC GCAATCCTGA    9169

TGGATTCATG TGCTTGCATT GACCATGACC CTGAGTGGTA TGAGGACCTC ATCTGCGGTA    9229

TTGCCCGGTG CGCCCGCCAG GATGGTTATA GCTTCCCAGG TCCGGCATTT TTCATGTCCA    9289

TGTGGGAGAA GCTGAGAAGT CATAATGAAG GGAAGAAATT CCGCCACTGC GGCATCTGCG    9349

ACGCCAAAGC CGACTATGCG TCCGCCTGTG GGCTTGATTT GTGTTTGTTC CATTCGCACT    9409

TTCATCAACA CTGCCCYGTC ACTCTGAGCT GCGGTCACCA TGCCGGTTCA AAGGAATGTT    9469

CGCAGTGTCA GTCACCTGTT GGGGCTGGCA GATCCCCTCT TGATGCCGTG CTAAAACAAA    9529

TTCCATACAA ACCTCCTCGT ACTGTCATCA TGAAGGTGGG TAATAAAACA ACGGCCCTCG    9589

ATCCGGGGAG GTACCAGTCC CGTCGAGGTC TCGTTGCAGT CAAGAGGGGT ATTGCAGGCA    9649

ATGAAGTTGA TCTTTCTGAT GGRGACTACC AAGTGGTGCC TCTTTTGCCG ACTTGCAAAG    9709

ACATAAACAT GGTGAAGGTG GCTTGCAATG TACTACTCAG CAAGTTCATA GTAGGGCCAC    9769

CAGGTTCCGG AAAGACCACC TGGCTACTGA GTCAAGTCCA GGACGATGAT GTCATTTACA    9829

YACCCACCCA TCAGACTATG TTTGATATAG TCAGTGCTCT CAAAGTTTGC AGGTATTCCA    9889

TTCCAGGAGC CTCAGGACTC CCTTTCCCAC CACCTGCCAG GTCCGGGCCG TGGGTTAGGC    9949

TTATTGCCAG CGGGCACGTC CCTGGCCGAG TATCATACCT CGATGAGGCT GGATATTGTA   10009

ATCATCTGGA CATTCTTAGA CTGCTTTCCA AAACACCCCT TGTGTGTTTG GGTGACCTTC   10069

AGCAACTTCA CCCTGTCGGC TTTGATTCCT ACTGTTATGT GTTCGATCAG ATGCCTCAGA   10129

AGCAGCTGAC CACTATTTAC AGATTTGGCC CTAACATCTG CGCACGCATC CAGCCTTGTT   10189

ACAGGGAGAA ACTTGAATCT AAGGCTAGGA CACTAGGGT GGTTTTTACC ACCCGGCCTG   10249

TGGCCTTTGG TCAGGTGCTG ACACCATACC ATAAAGATCG CATCGGCTCT GCGATAACCA   10309

TAGATTCATC CCAGGGGGCC ACCTTTGATA TTGTGACATT GCATCTACCA TCGCCAAAGT   10369

CCCTAAATAA ATCCCGAGCA CTTGTAGCCA TCACTCGGGC AAGACACGGG TTGTTCATTT   10429

ATGACCCTCA TAACCAGCTC CAGGAGTTTT TCAACTTAAC CCCTGAGCGC ACTGATTGTA   10489
```

```
ACCTTGTGTT CAGCCGTGGG GATGAGCTGG TAGTTCTGAA TGCGGATAAT GCAGTCACAA    10549

CTGTAGCGAA GGCCCTTGAG ACAGGTCCAT CTCGATTTCG AGTATCAGAC CCGAGGTGCA    10609

AGTCTCTCTT AGCCGCTTGT TCGGCCAGTC TGGAAGGGAG CTGTATGCCA CTACCGCAAG    10669

TGGCACATAA CCTGGGGTTT TACTTTTCCC CGGACAGTCC AACATTTGCA CCTCTGCCAA    10729

AAGAGTTGGC GCCACATTGG CCAGTGGTTA CCCACCAGAA TAATCGGGCG TGGCCTGATC    10789

GACTTGTCGC TAGTATGCGC CCAATTGATG CCCGCTACAG CAAGCCAATG GTCGGTGCAG    10849

GGTATGTGGT CGGGCCGTCC ACCTTTCTTG GTACTCCTGG TGTGGTGTCA TACTATCTCA    10909

CACTATACAT CAGGGGTGAG CCCCAGGCCT TGCCAGAAAC ACTCGTTTCA ACAGGGCGTA    10969

TAGCCACAGA TTGTCGGGAG TATCTCGACG CGGCTGAGGA AGAGGCAGCA AAAGAACTCC    11029

CCCACGCATT CATTGGCGAT GTCAAAGGTA CCACGGTTGG GGGGTGTCAT CACATTACAT    11089

CAAAATACCT ACCTAGGTCC CTGCCTAAGG ACTCTGTTGC CGTAGTTGGA GTAAGTTCGC    11149

CCGGCAGGGC TGCTAAAGCC GTGTGCACTC TCACCGATGT GTACCTCCCC GAACTCCGGC    11209

CATATCTGCA ACCTGAGACG GCATCAAAAT GCTGGAAACT CAAATTAGAC TTCAGGGACG    11269

TCCGACTAAT GGTCTGGAAA GGAGCCACCG CCTATTTCCA GTTGGAAGGG CTTACATGGT    11329

CGGCGCTGCC CGACTATGCC AGGTTYATTC AGCTGCCCAA GGATGCCGTT GTATACATTG    11389

ATCCGTGTAT AGGACCGGCA ACAGCCAACC GTAAGGTCGT GCGAACCACA GACTGGCGGG    11449

CCGACCTGGC AGTGACACCG TATGATTACG GTGCCCAGAA CATTTTGACA ACAGCCTGGT    11509

TCGAGGACCT CGGGCCGCAG TGGAAGATTT TGGGGTTGCA GCCCTTTAGG CGAGCATTTG    11569

GCTTTGAAAA CACTGAGGAT TGGGCAATCC TTGCACGCCG TATGAATGAC GGCAAGGACT    11629

ACACTGACTA TAACTGGAAC TGTGTTCGAG AACGCCCACA CGCCATCTAC GGGCGTGCTC    11689

GTGACCATAC GTATCATTTT GCCCCTGGCA CAGAATTGCA GGTAGAGCTA GGTAAACCCC    11749

GGCTGCCGCC TGGGCAAGTG CCG TGAATTCGGG GTGATGCAAT GGGGTCACTG           11802

TGGAGTAAAA TCAGCCAGCT GTTCGTGGAC GCCTTCACTG AGTTCCTTGT TAGTGTGGTT    11862

GATATTGYCA TTTTCCTTGC CATACTGTTT GGGTTCACCG TCGCAGGATG GTTACTGGTC    11922

TTTCTTCTCA GAGTGGTTTG CTCCGCGCTT CTCCGTTCGC GCTCTGCCAT TCACTCTCCC    11982

GAACTATCGA AGGTCCTATG AAGGCTTGTT GCCCAACTGC AGACCGGATG TCCCACAATT    12042

TGCAGTCAAG CACCCATTGG GYATGTTTTG GCACATGCGA GTTTCCCACT TGATTGATGA    12102

GRTGGTCTCT CGTCGCATTT ACCAGACCAT GGAACATTCA GGTCAAGCGG CCTGGAAGCA    12162

GGTGGTTGGT GAGGCCACTC TCACGAAGCT GTCAGGGCTC GATATAGTTA CTCATTTCCA    12222

ACACCTGGCC GCAGTGGAGG CGGATTCTTG CCGCTTTCTC AGCTCACGAC TCGTGATGCT    12282

AAAAAATCTT GCCGTTGGCA ATGTGAGCCT ACAGTACAAC ACCACGTTGG ACCGCGTTGA    12342

GCTCATCTTC CCCACGCCAG GTACGAGGCC CAAGTTGACC GATTTCAGAC AATGGCTCAT    12402

CAGTGTGCAC GCTTCCATTT TTTCCTCTGT GGCTTCATCT GTTACCTTGT TCATAGTGCT    12462

TTGGCTTCGA ATTCCAGCTC TACGCTATGT TTTTGGTTTC CATTGGCCCA CGGCAACACA    12522

TCATTCGAGC TGACCATCAA CTACACCATA TGCATGCCCT GTTCTACCAG TCAAGCGGCT    12582

CGCCAAAGGC TCGAGCCCGG TCGTAACATG TGGTGCAAAA TAGGGCATGA CAGGTGTGAG    12642

GAGCGTGACC ATGATGAGTT GTTAATGTCC ATCCCGTCCG GGTACGACAA CCTCAAACTT    12702

GAGGGTTATT ATGCTTGGCT GGCTTTTTTG TCCTTTTCCT ACGCGGCCCA ATTCCATCCG    12762

GAGTTGTTCG GGATAGGGAA TGTGTCGCGC GTCTTCGTGG ACAAGCGACA CCAGTTCATT    12822

TGTGCCGAGC ATGATGGACA CAATTCAACC GTATCTACCG GACACAACAT CTCCGCATTA    12882
```

```
TATGCGGCAT ATTACCACCA CCAAATAGAC GGGGGCAATT GGTTCCATTT GGAATGGCTG    12942

CGGCCACTCT TTTCTTCCTG GCTGGTGCTC AACATATCAT GGTTTCTGAG GCGTTCGCCT    13002

GTAAGCCCTG TTTCTCGACG CATCTATCAG ATATTGAGAC CAACACGACC GCGGCTGCCG    13062

GTTTCATGGT CCTTCAGGAC ATCAATTGTT TCCGACCTCA CGGGGTCTCA GCAGCGCAAG    13122

AGAAAATTTC CTTCGGAAAG TCGTCCCAAT GTCGTGAAGC CGTCGGTACT CCCCAGTACA    13182

TCACGA TAACGGCTAA CGTGACCGAC GAATCATACT TGTACAACGC GGACCTGCTG        13238

ATGCTTTCTG CGTGCCTTTT CTACGCCTCA GAAATGAGCG AGAAAGGCTT CAAAGTCATC    13298

TTTGGGAATG TCTCTGGCGT TGTTTCTGCT TGTGTCAATT TCACAGATTA TGTGGCCCAT    13358

GTGACCCAAC ATACCCAGCA GCATCATCTG GTAATTGATC ACATTCGGTT GCTGCATTTC    13418

CTGACACCAT CTGCAATGAG GTGGGCTACA ACCATTGCTT GTTTGTTCGC CATTCTCTTG    13478

GCAATA TGAGATGTTC TCACAAATTG GGGCGTTTCT TGACTCCGCA CTCTTGCTTC        13534

TGGTGGCTTT TTTTGCTGTG TACCGGCTTG TCCTGGTCCT TGCCGATGG CAACGGCGAC     13594

AGCTCGACAT ACCAATACAT ATATAACTTG ACGATATGCG AGCTGAATGG GACCGACTGG    13654

TTGTCCAGCC ATTTTGGTTG GGCAGTCGAG ACCTTTGTGC TTTACCCGGT TGCCACTCAT    13714

ATCCTCTCAC TGGGTTTTCT CACAACAAGC CATTTTTTTG ACGCGCTCGG TCTCGGCGCT    13774

GTATCCACTG CAGGATTTGT TGGCGGGCGG TACGTACTCT GCAGCGTCTA CGGCGCTTGT    13834

GCTTTCGCAG CGTTCGTATG TTTTGTCATC CGTGCTGCTA AAAATTGCAT GGCCTGCCGC    13894

TATGCCCGTA CCCGGTTTAC CAACTTCATT GTGGACGACC GGGGGAGAGT TCATCGATGG    13954

AAGTCTCCAA TAGTGGTAGA AAAATTGGGC AAAGCCGAAG TCGATGGCAA CCTCGTCACC    14014

ATCAAACATG TCGTCCTCGA AGGGGTTAAA GCTCAACCCT TGACGAGGAC TTCGGCTGAG    14074

CAATGGGAGG CC TAGACGATTT TTGCAACGAT CCTATCGCCG CACAAAAGCT            14126

CGTGCTAGCC TTTAGCATCA CATACACACC TATAATGATA TACGCCCTTA AGGTGTCACG    14186

CGGCCGACTC CTGGGCTGT TGCACATCCT AATATTTCTG AACTGTTCCT TTACATTCGG     14246

ATACATGACA TATGTGCATT TTCAATCCAC CAACCGTGTC GCACTTACCC TGGGGGCTGT    14306

TGTCGCCCTT CTGTGGGGTG TTTACAGCTT CACAGAGTCA TGGAAGTTTA TCACTTCCAG    14366

ATGCAGATTG TGTTGCCTTG GCCGGCGATA CATTCTGGCC CCTGCCCATC ACGTAGAAAG    14426

TGCTGCAGGT CTCCATTCAA TCTCAGCGTC TGGTAACCGA GCATACGCTG TGAGAAAGCC    14486

CGGACTAACA TCAGTGAACG GCACTCTAGT ACCAGGACTT CGGAGCCTCG TGCTGGGCGG    14546

CAAACGAGCT GTTAAACGAG GAGTGGTTAA CCTCGTCAAG TATGGCCGG TAAAAACCAG     14605

AGCCAGAAGA AAAAGAAAAG TACAGCTCCG ATGGGAATG GCCAGCCAGT CAATCAACTG     14665

TGCCAGTTGC TGGGTGCAAT GATAAAGTCC CAGCGCCAGC AACCTAGGGG AGGACAGGCY    14725

AAAAAGAAAA AGCCTGAGAA GCCACATTTT CCCCTGGCTG CTGAAGATGA CATCCGGCAC    14785

CACCTCACCC AGACTGAACG CTCCCTCTGC TTGCAATCGA TCCAGACGGC TTTCAATCAA    14845

GGCGCAGGAA CTGCGTCRCT TTCATCCAGC GGGAAGGTCA GTTTTCAGGT TGAGTTTATG    14905

CTGCCGGTTG CTCATACAGT GCGCCTGATT CGCGTGACTT CTACATCCGC CAGTCAGGGT    14965

GCAAGT TAATTTGACA GTCAGGTGAA TGGCCGCGAT GGCGTGTGGC CTCTGAGTCA        15021

CCTATTCAAT TAGGGCGATC ACATGGGGGT CATACTTAAT TCAGGCAGGA ACCATGTGAC    15081

CGAAATTAAA AAAAAAAAAA AAAAAA                                        15108
```

(2) INFORMATION FOR SEQ ID NO: 2:

(i) SEQUENCE CHARACTERISTICS:
    (A) LENGTH: 2396 amino acids
    (B) TYPE: amino acid
    (D) TOPOLOGY: linear (ii) MOLECULE TYPE: protein (xi) SEQUENCE DESCRIPTION: SEQ ID NO: 2:

```
Met Ser Gly Thr Phe Ser Arg Cys Met Cys Thr Pro Ala Ala Arg Val
1               5                   10                  15

Phe Trp Asn Ala Gly Gln Val Phe Cys Thr Arg Cys Leu Ser Ala Arg
            20                  25                  30

Ser Leu Leu Ser Pro Glu Leu Gln Asp Thr Asp Leu Gly Ala Val Gly
        35                  40                  45

Leu Phe Tyr Lys Pro Arg Asp Lys Leu His Trp Lys Val Pro Ile Gly
    50                  55                  60

Ile Pro Gln Val Glu Cys Thr Pro Ser Gly Cys Cys Trp Leu Ser Ala
65                  70                  75                  80

Val Phe Pro Leu Ala Arg Met Thr Ser Gly Asn His Asn Phe Leu Gln
                85                  90                  95

Arg Leu Val Lys Val Ala Asp Val Leu Tyr Arg Asp Gly Cys Leu Ala
            100                 105                 110

Pro Arg His Leu Arg Glu Leu Gln Val Tyr Glu Arg Gly Cys Asn Trp
        115                 120                 125

Tyr Pro Ile Thr Gly Pro Val Pro Gly Met Gly Leu Phe Ala Asn Ser
    130                 135                 140

Met His Val Ser Asp Gln Pro Phe Pro Gly Ala Thr His Val Leu Thr
145                 150                 155                 160

Asn Ser Pro Leu Pro Gln Gln Ala Cys Arg Gln Pro Phe Cys Pro Phe
                165                 170                 175

Glu Glu Ala His Ser Ser Val Tyr Arg Trp Lys Lys Phe Val Val Phe
            180                 185                 190

Thr Asp Ser Ser Leu Asn Gly Arg Ser Arg Met Met Trp Thr Pro Glu
        195                 200                 205

Ser Asp Asp Ser Ala Ala Leu Glu Val Leu Pro Pro Glu Leu Glu Arg
    210                 215                 220

Gln Val Glu Ile Leu Ile Arg Ser Phe Pro Ala His His Pro Val Asp
225                 230                 235                 240

Leu Ala Asp Trp Glu Leu Thr Glu Ser Pro Glu Asn Gly Phe Ser Phe
                245                 250                 255

Asn Thr Ser His Ser Cys Gly His Leu Val Gln Asn Pro Asp Val Phe
            260                 265                 270

Asp Gly Lys Cys Trp Leu Ser Cys Phe Leu Gly Gln Ser Val Glu Val
        275                 280                 285

Arg Cys His Glu Glu His Leu Ala Asp Ala Phe Gly Tyr Gln Thr Lys
    290                 295                 300

Trp Gly Val His Gly Lys Tyr Leu Gln Arg Arg Leu Gln Val Arg Gly
305                 310                 315                 320

Ile Arg Ala Val Val Asp Pro Asp Gly Pro Ile His Val Glu Ala Leu
                325                 330                 335

Ser Cys Pro Gln Ser Trp Ile Arg His Leu Thr Leu Asp Asp Asp Val
            340                 345                 350

Thr Pro Gly Phe Val Arg Leu Thr Ser Leu Arg Ile Val Pro Asn Thr
        355                 360                 365

Glu Pro Thr Thr Ser Arg Ile Phe Arg Phe Gly Ala His Lys Trp Tyr
    370                 375                 380
```

```
Gly Ala Ala Gly Lys Arg Ala Arg Ala Lys Arg Ala Ala Lys Ser Glu
385                 390                 395                 400

Lys Asp Ser Ala Pro Thr Pro Lys Val Ala Leu Pro Val Pro Thr Cys
            405                 410                 415

Gly Ile Thr Thr Tyr Ser Pro Pro Thr Asp Gly Ser Cys Gly Trp His
        420                 425                 430

Val Leu Ala Ala Ile Met Asn Arg Met Ile Asn Gly Asp Phe Thr Ser
    435                 440                 445

Pro Leu Thr Gln Tyr Asn Arg Pro Glu Asp Asp Trp Ala Ser Asp Tyr
450                 455                 460

Asp Leu Val Gln Ala Ile Gln Cys Leu Arg Leu Pro Ala Thr Val Val
465                 470                 475                 480

Arg Asn Arg Ala Cys Pro Asn Ala Lys Tyr Leu Ile Lys Leu Asn Gly
                485                 490                 495

Val His Trp Glu Val Glu Val Arg Ser Gly Met Ala Pro Arg Ser Leu
            500                 505                 510

Ser Arg Glu Cys Val Val Gly Val Cys Ser Glu Gly Cys Val Ala Pro
        515                 520                 525

Pro Tyr Pro Ala Asp Gly Leu Pro Lys Arg Ala Leu Glu Ala Leu Ala
    530                 535                 540

Ser Ala Tyr Arg Leu Pro Ser Asp Cys Val Ser Ser Gly Ile Ala Asp
545                 550                 555                 560

Phe Leu Ala Asn Pro Pro Pro Gln Glu Phe Trp Thr Leu Asp Lys Met
                565                 570                 575

Leu Thr Ser Pro Ser Pro Glu Arg Ser Gly Phe Ser Ser Leu Tyr Lys
            580                 585                 590

Leu Leu Leu Glu Val Val Pro Gln Lys Cys Gly Ala Thr Glu Gly Ala
        595                 600                 605

Phe Ile Tyr Ala Val Glu Arg Met Leu Lys Asp Cys Pro Ser Ser Lys
    610                 615                 620

Gln Ala Met Ala Leu Leu Ala Lys Ile Lys Val Pro Ser Ser Lys Ala
625                 630                 635                 640

Pro Ser Val Ser Leu Asp Glu Cys Phe Pro Thr Asp Val Leu Ala Asp
                645                 650                 655

Phe Glu Pro Ala Ser Gln Glu Arg Pro Gln Ser Ser Gly Ala Ala Val
            660                 665                 670

Val Leu Cys Ser Pro Asp Ala Lys Glu Phe Glu Glu Ala Ala Xaa Glu
        675                 680                 685

Glu Val Gln Glu Ser Gly His Lys Ala Val His Ser Ala Leu Leu Ala
    690                 695                 700

Glu Gly Pro Asn Asn Glu Gln Val Gln Val Ala Gly Glu Gln Leu
705                 710                 715                 720

Lys Leu Gly Gly Cys Gly Leu Ala Val Gly Asn Ala His Glu Gly Ala
                725                 730                 735

Leu Val Ser Ala Gly Leu Ile Asn Leu Val Gly Gly Asn Leu Ser Pro
            740                 745                 750

Ser Asp Pro Met Lys Glu Asn Met Leu Asn Ser Arg Glu Asp Glu Pro
        755                 760                 765

Leu Asp Leu Ser Gln Pro Ala Pro Ala Ser Thr Thr Thr Leu Val Arg
    770                 775                 780

Glu Gln Thr Pro Asp Asn Pro Gly Ser Asp Ala Gly Ala Leu Pro Val
785                 790                 795                 800

Thr Val Arg Glu Phe Val Pro Thr Gly Pro Ile Leu Cys His Val Glu
```

```
                        805                 810                 815
His Cys Gly Thr Glu Ser Gly Asp Ser Ser Pro Leu Asp Leu Ser
            820                 825                 830

Asp Ala Gln Thr Leu Asp Gln Pro Leu Asn Leu Ser Leu Ala Ala Trp
            835                 840                 845

Pro Val Arg Ala Thr Ala Ser Asp Pro Gly Trp Val His Gly Arg Arg
            850                 855                 860

Glu Pro Val Phe Val Lys Pro Arg Asn Ala Phe Ser Asp Gly Asp Ser
865                 870                 875                 880

Ala Leu Gln Phe Gly Glu Leu Ser Glu Ser Ser Val Ile Glu Phe
                    885                 890                 895

Asp Arg Thr Lys Asp Ala Pro Val Val Asp Ala Pro Val Asp Leu Thr
            900                 905                 910

Thr Ser Asn Glu Ala Leu Ser Val Val Asp Pro Phe Glu Phe Ala Glu
            915                 920                 925

Leu Lys Arg Pro Arg Phe Ser Ala Gln Ala Leu Ile Asp Arg Gly Gly
            930                 935                 940

Pro Leu Ala Asp Val His Ala Lys Ile Lys Asn Arg Val Tyr Glu Gln
945                 950                 955                 960

Cys Leu Gln Ala Cys Glu Pro Gly Ser Arg Ala Thr Pro Ala Thr Arg
                    965                 970                 975

Glu Trp Leu Asp Lys Met Trp Asp Arg Val Asp Met Lys Thr Trp Arg
            980                 985                 990

Cys Thr Ser Gln Phe Gln Ala Gly Arg Ile Leu Ala Ser Leu Lys Phe
            995                 1000                1005

Leu Pro Asp Met Ile Gln Asp Thr Pro Pro Val Pro Arg Lys Asn
    1010                1015                1020

Arg Ala Ser Asp Asn Ala Gly Leu Lys Gln Leu Val Ala Gln Trp Asp
1025                1030                1035                1040

Arg Lys Leu Ser Val Thr Pro Pro Lys Pro Val Gly Pro Val Leu
            1045                1050                1055

Asp Gln Ile Val Pro Pro Thr Asp Ile Gln Gln Glu Asp Val Thr
            1060                1065                1070

Pro Ser Asp Gly Pro Pro His Ala Pro Asp Phe Pro Ser Arg Val Ser
            1075                1080                1085

Thr Gly Gly Ser Trp Lys Gly Leu Met Leu Ser Gly Thr Arg Leu Ala
            1090                1095                1100

Gly Ser Ile Ser Gln Arg Leu Met Thr Trp Val Phe Glu Val Phe Ser
1105                1110                1115                1120

His Leu Pro Ala Phe Met Leu Thr Leu Phe Ser Pro Arg Gly Ser Met
                    1125                1130                1135

Ala Pro Gly Asp Trp Leu Phe Ala Gly Val Val Leu Ala Leu Leu
            1140                1145                1150

Leu Cys Arg Ser Tyr Pro Ile Leu Gly Cys Leu Pro Leu Leu Gly Val
            1155                1160                1165

Phe Ser Gly Ser Leu Arg Arg Val Arg Leu Gly Val Phe Gly Ser Trp
            1170                1175                1180

Met Ala Phe Ala Val Phe Leu Phe Ser Thr Pro Ser Asn Pro Val Gly
1185                1190                1195                1200

Ser Ser Cys Asp His Asp Ser Pro Glu Cys His Ala Glu Leu Leu Ala
                    1205                1210                1215

Leu Glu Gln Arg Gln Leu Trp Glu Pro Val Arg Gly Leu Val Val Gly
            1220                1225                1230
```

```
Pro Ser Gly Leu Leu Cys Val Ile Leu Gly Lys Leu Leu Gly Gly Ser
        1235                1240                1245

Arg Tyr Leu Trp His Val Leu Leu Arg Leu Cys Met Leu Ala Asp Leu
        1250                1255                1260

Ala Leu Ser Leu Val Tyr Val Ser Gln Gly Arg Cys His Lys Cys
1265                1270                1275                1280

Trp Gly Lys Cys Ile Arg Thr Ala Pro Ala Glu Val Ala Leu Asn Val
        1285                1290                1295

Phe Pro Phe Ser Arg Ala Thr Arg Val Ser Leu Val Ser Leu Cys Asp
        1300                1305                1310

Arg Phe Gln Thr Pro Lys Gly Val Asp Pro Val His Leu Ala Thr Gly
        1315                1320                1325

Trp Arg Gly Cys Trp Arg Gly Glu Ser Pro Ile His Gln Pro His Gln
        1330                1335                1340

Lys Pro Ile Ala Tyr Ala Asn Leu Asp Glu Lys Lys Met Ser Ala Gln
1345                1350                1355                1360

Thr Val Val Ala Val Pro Tyr Asp Pro Ser Gln Ala Ile Lys Cys Leu
        1365                1370                1375

Lys Val Leu Gln Ala Gly Gly Ala Ile Val Asp Gln Pro Thr Pro Glu
        1380                1385                1390

Val Val Arg Val Ser Glu Ile Pro Phe Ser Ala Pro Phe Phe Pro Lys
        1395                1400                1405

Val Pro Val Asn Pro Asp Cys Arg Val Val Asp Ser Asp Thr Phe
        1410                1415                1420

Val Ala Ala Val Arg Cys Gly Tyr Ser Thr Ala Gln Leu Xaa Leu Gly
1425                1430                1435                1440

Arg Gly Asn Phe Ala Lys Leu Asn Gln Thr Pro Pro Arg Asn Ser Ile
        1445                1450                1455

Ser Thr Lys Thr Thr Gly Gly Ala Ser Tyr Thr Leu Ala Val Ala Gln
        1460                1465                1470

Val Ser Ala Trp Thr Leu Val His Phe Ile Leu Gly Leu Trp Phe Thr
        1475                1480                1485

Ser Pro Gln Val Cys Gly Arg Gly Thr Ala Asp Pro Trp Cys Ser Asn
        1490                1495                1500

Pro Phe Ser Tyr Pro Thr Tyr Gly Pro Gly Val Val Cys Ser Ser Arg
1505                1510                1515                1520

Leu Cys Val Ser Ala Asp Gly Val Thr Leu Pro Leu Phe Ser Ala Val
        1525                1530                1535

Ala Gln Leu Ser Gly Arg Glu Val Gly Ile Phe Ile Leu Val Leu Val
        1540                1545                1550

Ser Leu Thr Ala Leu Ala His Arg Met Ala Leu Lys Ala Asp Met Leu
        1555                1560                1565

Val Val Phe Ser Ala Phe Cys Ala Tyr Ala Trp Pro Met Ser Ser Trp
        1570                1575                1580

Leu Ile Cys Phe Phe Pro Ile Leu Leu Lys Trp Val Thr Leu His Pro
1585                1590                1595                1600

Leu Thr Met Leu Trp Val His Ser Phe Leu Val Phe Cys Leu Pro Ala
        1605                1610                1615

Ala Gly Ile Leu Ser Leu Gly Ile Thr Gly Leu Leu Trp Ala Ile Gly
        1620                1625                1630

Arg Phe Thr Gln Val Ala Gly Ile Ile Thr Pro Tyr Asp Ile His Gln
        1635                1640                1645

Tyr Thr Ser Gly Pro Arg Gly Ala Ala Ala Val Ala Thr Ala Pro Glu
        1650                1655                1660
```

```
Gly Thr Tyr Met Ala Ala Val Arg Arg Ala Ala Leu Thr Gly Arg Thr
1665                1670                1675                1680

Leu Ile Phe Thr Pro Ser Ala Val Gly Ser Leu Leu Glu Ala Phe
            1685                1690                1695

Arg Thr His Lys Pro Cys Leu Asn Thr Val Asn Val Val Gly Ser Ser
                1700                1705                1710

Leu Gly Ser Gly Gly Val Phe Thr Ile Asp Gly Arg Arg Thr Val Val
            1715                1720                1725

Thr Ala Ala His Val Leu Asn Gly Asp Thr Ala Arg Val Thr Gly Asp
            1730                1735                1740

Ser Tyr Asn Arg Met His Thr Phe Lys Thr Asn Gly Asp Tyr Ala Trp
1745                1750                1755                1760

Ser His Ala Asp Asp Trp Gln Gly Val Ala Pro Val Lys Val Ala
                1765                1770                1775

Lys Gly Tyr Arg Gly Arg Ala Tyr Trp Gln Thr Ser Thr Gly Val Glu
                1780                1785                1790

Pro Gly Ile Ile Gly Glu Gly Phe Ala Phe Cys Phe Thr Asn Cys Gly
            1795                1800                1805

Asp Ser Gly Ser Pro Val Ile Ser Glu Ser Gly Asp Leu Ile Gly Ile
            1810                1815                1820

His Thr Gly Ser Asn Lys Leu Gly Ser Gly Leu Val Thr Thr Pro Glu
1825                1830                1835                1840

Gly Glu Thr Cys Thr Ile Lys Glu Thr Lys Leu Ser Asp Leu Ser Arg
                1845                1850                1855

His Phe Ala Gly Pro Ser Val Pro Leu Gly Asp Ile Lys Leu Ser Pro
                1860                1865                1870

Ala Ile Ile Pro Asp Val Thr Ser Ile Pro Ser Asp Leu Ala Ser Leu
            1875                1880                1885

Leu Ala Ser Val Pro Val Glu Gly Gly Leu Ser Thr Val Gln Leu
            1890                1895                1900

Leu Cys Val Phe Phe Leu Leu Trp Arg Met Met Gly His Ala Trp Thr
1905                1910                1915                1920

Pro Ile Val Ala Val Gly Phe Phe Leu Leu Asn Glu Ile Leu Pro Ala
                1925                1930                1935

Val Leu Val Arg Ala Val Phe Ser Phe Ala Leu Phe Val Leu Ala Trp
                1940                1945                1950

Ala Thr Pro Trp Ser Ala Gln Val Leu Met Ile Arg Leu Leu Thr Ala
                1955                1960                1965

Ser Leu Asn Arg Asn Lys Leu Ser Leu Ala Phe Tyr Ala Leu Gly Gly
            1970                1975                1980

Val Val Gly Leu Ala Ala Glu Ile Gly Thr Phe Ala Gly Arg Leu Ser
1985                1990                1995                2000

Glu Leu Ser Gln Ala Leu Ser Thr Tyr Cys Phe Leu Pro Arg Val Leu
                2005                2010                2015

Ala Met Thr Ser Cys Val Pro Thr Ile Ile Gly Gly Leu His Thr
                2020                2025                2030

Leu Gly Val Ile Leu Trp Xaa Phe Lys Tyr Arg Cys Leu His Asn Met
            2035                2040                2045

Leu Val Gly Asp Gly Ser Phe Ser Ser Ala Phe Phe Leu Arg Tyr Phe
            2050                2055                2060

Ala Glu Gly Asn Leu Arg Lys Gly Val Ser Gln Ser Cys Gly Met Asn
2065                2070                2075                2080

Asn Glu Ser Leu Thr Ala Ala Leu Ala Cys Lys Leu Ser Gln Ala Asp
```

-continued

```
                    2085                2090                2095
Leu Asp Phe Leu Ser Ser Leu Thr Asn Phe Lys Cys Phe Val Ser Ala
                2100                2105                2110
Ser Asn Met Lys Asn Ala Ala Gly Gln Tyr Ile Glu Ala Ala Tyr Ala
                2115                2120                2125
Lys Ala Leu Arg Gln Glu Leu Ala Ser Leu Val Gln Ile Asp Lys Met
                2130                2135                2140
Lys Gly Val Leu Ser Lys Leu Glu Ala Phe Ala Glu Thr Ala Thr Pro
2145                2150                2155                2160
Ser Leu Asp Ile Gly Asp Val Ile Val Leu Leu Gly Gln His Pro His
                2165                2170                2175
Gly Ser Ile Leu Asp Ile Asn Val Gly Thr Glu Arg Lys Thr Val Ser
                2180                2185                2190
Val Gln Glu Thr Arg Ser Leu Gly Gly Ser Lys Phe Ser Val Cys Thr
                2195                2200                2205
Val Val Ser Asn Thr Pro Val Asp Ala Xaa Thr Gly Ile Pro Leu Gln
                2210                2215                2220
Thr Pro Thr Pro Leu Phe Glu Asn Gly Pro Arg His Arg Ser Glu Glu
2225                2230                2235                2240
Asp Asp Leu Lys Val Glu Arg Met Lys Lys His Cys Val Ser Leu Gly
                2245                2250                2255
Phe His Asn Ile Asn Gly Lys Val Tyr Cys Lys Ile Trp Asp Lys Ser
                2260                2265                2270
Thr Gly Asp Thr Phe Tyr Thr Asp Asp Ser Arg Tyr Thr Gln Asp His
                2275                2280                2285
Ala Phe Gln Asp Arg Ser Ala Asp Tyr Arg Asp Arg Asp Tyr Glu Gly
                2290                2295                2300
Val Gln Thr Thr Pro Gln Gln Gly Phe Asp Pro Lys Ser Glu Thr Pro
2305                2310                2315                2320
Val Gly Thr Val Val Ile Gly Gly Ile Thr Tyr Asn Arg Tyr Leu Ile
                2325                2330                2335
Lys Gly Lys Glu Val Leu Val Pro Lys Pro Asp Asn Cys Leu Glu Ala
                2340                2345                2350
Ala Lys Leu Ser Leu Glu Gln Ala Leu Ala Gly Met Gly Gln Thr Cys
                2355                2360                2365
Asp Leu Thr Ala Ala Glu Val Glu Lys Leu Lys Arg Ile Ile Ser Gln
                2370                2375                2380
Leu Gln Gly Leu Thr Thr Glu Gln Ala Leu Asn Cys
2385                2390                2395
```

(2) INFORMATION FOR SEQ ID NO: 3:

(i) SEQUENCE CHARACTERISTICS:
        (A) LENGTH: 1463 amino acids
        (B) TYPE: amino acid
        (D) TOPOLOGY: linear (ii) MOLECULE TYPE: protein (xi) SEQUENCE DESCRIPTION: SEQ ID NO: 3:

```
Thr Gly Phe Lys Leu Leu Ala Ala Ser Gly Leu Thr Arg Cys Gly Arg
1               5                   10                  15
Gly Gly Leu Val Val Thr Glu Thr Ala Val Lys Ile Ile Lys Tyr His
                20                  25                  30
Ser Arg Thr Phe Thr Leu Gly Pro Leu Asp Leu Lys Val Thr Ser Glu
                35                  40                  45
```

```
Val Glu Val Lys Lys Ser Thr Glu Gln Gly His Ala Val Ala Asn
 50                  55                  60

Leu Cys Ser Gly Val Ile Leu Met Arg Pro His Pro Pro Ser Leu Val
 65                  70                  75                  80

Asp Val Leu Leu Lys Pro Gly Leu Asp Thr Ile Pro Gly Ile Gln Pro
                 85                  90                  95

Gly His Gly Ala Gly Asn Met Gly Val Asp Gly Ser Ile Trp Asp Phe
            100                 105                 110

Glu Thr Ala Pro Thr Lys Ala Glu Leu Glu Leu Ser Lys Gln Ile Ile
            115                 120                 125

Gln Ala Cys Glu Val Arg Arg Gly Asp Ala Pro Asn Leu Gln Leu Pro
        130                 135                 140

Tyr Lys Leu Tyr Pro Val Arg Gly Asp Pro Glu Arg His Lys Gly Arg
145                 150                 155                 160

Leu Ile Asn Thr Arg Phe Gly Asp Leu Pro Tyr Lys Thr Pro Gln Asp
                165                 170                 175

Thr Lys Ser Ala Ile His Ala Ala Cys Cys Leu His Pro Asn Gly Ala
            180                 185                 190

Pro Val Ser Asp Gly Lys Ser Thr Leu Gly Thr Thr Leu Gln His Gly
        195                 200                 205

Phe Glu Leu Tyr Val Pro Thr Val Pro Tyr Ser Val Met Glu Tyr Leu
    210                 215                 220

Asp Ser Arg Pro Asp Thr Pro Phe Met Cys Thr Lys His Gly Thr Ser
225                 230                 235                 240

Lys Ala Ala Ala Glu Asp Leu Gln Lys Tyr Asp Leu Ser Thr Gln Gly
                245                 250                 255

Phe Val Leu Pro Gly Val Leu Arg Leu Val Arg Arg Phe Ile Phe Gly
            260                 265                 270

His Ile Gly Lys Ala Pro Pro Leu Phe Leu Pro Ser Thr Tyr Pro Ala
        275                 280                 285

Lys Asn Ser Met Ala Gly Ile Asn Gly Gln Arg Phe Pro Thr Lys Asp
            290                 295                 300

Val Gln Ser Ile Pro Glu Ile Asp Glu Met Cys Ala Arg Ala Val Lys
305                 310                 315                 320

Glu Asn Trp Gln Thr Val Thr Pro Cys Thr Leu Lys Lys Gln Tyr Cys
                325                 330                 335

Ser Lys Pro Lys Thr Arg Thr Ile Leu Gly Thr Asn Asn Phe Ile Ala
            340                 345                 350

Leu Ala His Arg Ser Ala Leu Ser Gly Val Thr Gln Ala Phe Met Lys
        355                 360                 365

Lys Ala Trp Lys Ser Pro Ile Ala Leu Gly Lys Asn Lys Phe Lys Glu
    370                 375                 380

Leu His Cys Thr Val Ala Gly Arg Cys Leu Glu Ala Asp Leu Ala Ser
385                 390                 395                 400

Cys Asp Arg Ser Thr Pro Ala Ile Val Arg Trp Phe Val Ala Asn Leu
                405                 410                 415

Leu Tyr Glu Leu Ala Gly Cys Glu Glu Tyr Leu Pro Ser Tyr Val Leu
            420                 425                 430

Asn Cys Cys His Asp Leu Val Ala Thr Gln Asp Gly Ala Phe Thr Lys
        435                 440                 445

Arg Gly Gly Leu Ser Ser Gly Asp Pro Val Thr Ser Val Ser Asn Thr
    450                 455                 460

Val Tyr Ser Leu Val Ile Tyr Ala Gln His Met Val Leu Ser Ala Leu
465                 470                 475                 480
```

```
Lys Met Gly His Glu Ile Gly Leu Lys Phe Leu Glu Glu Gln Leu Lys
            485                 490                 495
Phe Glu Asp Leu Leu Glu Ile Gln Pro Met Leu Val Tyr Ser Asp Asp
            500                 505                 510
Leu Val Leu Tyr Ala Glu Arg Pro Xaa Phe Pro Asn Tyr His Trp Trp
            515                 520                 525
Val Glu His Leu Asp Leu Met Leu Gly Phe Arg Thr Asp Pro Lys Lys
            530                 535                 540
Thr Val Ile Thr Asp Lys Pro Ser Phe Leu Gly Cys Arg Ile Glu Ala
545                 550                 555                 560
Gly Arg Gln Leu Val Pro Asn Arg Asp Arg Ile Leu Ala Ala Leu Ala
            565                 570                 575
Tyr His Met Lys Ala Gln Asn Ala Ser Glu Tyr Tyr Ala Ser Ala Ala
            580                 585                 590
Ala Ile Leu Met Asp Ser Cys Ala Cys Ile Asp His Asp Pro Glu Trp
            595                 600                 605
Tyr Glu Asp Leu Ile Cys Gly Ile Ala Arg Cys Ala Arg Gln Asp Gly
            610                 615                 620
Tyr Ser Phe Pro Gly Pro Ala Phe Phe Met Ser Met Trp Glu Lys Leu
625                 630                 635                 640
Arg Ser His Asn Glu Gly Lys Lys Phe Arg His Cys Gly Ile Cys Asp
            645                 650                 655
Ala Lys Ala Asp Tyr Ala Ser Ala Cys Gly Leu Asp Leu Cys Leu Phe
            660                 665                 670
His Ser His Phe His Gln His Cys Xaa Val Thr Leu Ser Cys Gly His
            675                 680                 685
His Ala Gly Ser Lys Glu Cys Ser Gln Cys Gln Ser Pro Val Gly Ala
            690                 695                 700
Gly Arg Ser Pro Leu Asp Ala Val Leu Lys Gln Ile Pro Tyr Lys Pro
705                 710                 715                 720
Pro Arg Thr Val Ile Met Lys Val Gly Asn Lys Thr Thr Ala Leu Asp
            725                 730                 735
Pro Gly Arg Tyr Gln Ser Arg Arg Gly Leu Val Ala Val Lys Arg Gly
            740                 745                 750
Ile Ala Gly Asn Glu Val Asp Leu Ser Asp Xaa Asp Tyr Gln Val Val
            755                 760                 765
Pro Leu Leu Pro Thr Cys Lys Asp Ile Asn Met Val Lys Val Ala Cys
770                 775                 780
Asn Val Leu Leu Ser Lys Phe Ile Val Gly Pro Pro Gly Ser Gly Lys
785                 790                 795                 800
Thr Thr Trp Leu Leu Ser Gln Val Gln Asp Asp Val Ile Tyr Xaa
            805                 810                 815
Pro Thr His Gln Thr Met Phe Asp Ile Val Ser Ala Leu Lys Val Cys
            820                 825                 830
Arg Tyr Ser Ile Pro Gly Ala Ser Gly Leu Pro Phe Pro Pro Pro Ala
            835                 840                 845
Arg Ser Gly Pro Trp Val Arg Leu Ile Ala Ser Gly His Val Pro Gly
            850                 855                 860
Arg Val Ser Tyr Leu Asp Glu Ala Gly Tyr Cys Asn His Leu Asp Ile
865                 870                 875                 880
Leu Arg Leu Leu Ser Lys Thr Pro Leu Val Cys Leu Gly Asp Leu Gln
            885                 890                 895
Gln Leu His Pro Val Gly Phe Asp Ser Tyr Cys Tyr Val Phe Asp Gln
```

```
                900             905             910
Met Pro Gln Lys Gln Leu Thr Thr Ile Tyr Arg Phe Gly Pro Asn Ile
        915                 920             925

Cys Ala Arg Ile Gln Pro Cys Tyr Arg Glu Lys Leu Glu Ser Lys Ala
        930                 935             940

Arg Asn Thr Arg Val Val Phe Thr Thr Arg Pro Val Ala Phe Gly Gln
945                 950                 955             960

Val Leu Thr Pro Tyr His Lys Asp Arg Ile Gly Ser Ala Ile Thr Ile
                965                 970             975

Asp Ser Ser Gln Gly Ala Thr Phe Asp Ile Val Thr Leu His Leu Pro
            980                 985             990

Ser Pro Lys Ser Leu Asn Lys Ser Arg Ala Leu Val Ala Ile Thr Arg
        995                 1000            1005

Ala Arg His Gly Leu Phe Ile Tyr Asp Pro His Asn Gln Leu Gln Glu
        1010                1015            1020

Phe Phe Asn Leu Thr Pro Glu Arg Thr Asp Cys Asn Leu Val Phe Ser
1025                1030                1035            1040

Arg Gly Asp Glu Leu Val Val Leu Asn Ala Asp Asn Ala Val Thr Thr
                1045                1050            1055

Val Ala Lys Ala Leu Glu Thr Gly Pro Ser Arg Phe Arg Val Ser Asp
            1060                1065            1070

Pro Arg Cys Lys Ser Leu Leu Ala Ala Cys Ser Ala Ser Leu Glu Gly
        1075                1080            1085

Ser Cys Met Pro Leu Pro Gln Val Ala His Asn Leu Gly Phe Tyr Phe
        1090                1095            1100

Ser Pro Asp Ser Pro Thr Phe Ala Pro Leu Pro Lys Glu Leu Ala Pro
1105                1110                1115            1120

His Trp Pro Val Val Thr His Gln Asn Asn Arg Ala Trp Pro Asp Arg
                1125                1130            1135

Leu Val Ala Ser Met Arg Pro Ile Asp Ala Arg Tyr Ser Lys Pro Met
            1140                1145            1150

Val Gly Ala Gly Tyr Val Val Gly Pro Ser Thr Phe Leu Gly Thr Pro
        1155                1160            1165

Gly Val Val Ser Tyr Tyr Leu Thr Leu Tyr Ile Arg Gly Glu Pro Gln
        1170                1175            1180

Ala Leu Pro Glu Thr Leu Val Ser Thr Gly Arg Ile Ala Thr Asp Cys
1185                1190                1195            1200

Arg Glu Tyr Leu Asp Ala Ala Glu Glu Ala Ala Lys Glu Leu Pro
                1205                1210            1215

His Ala Phe Ile Gly Asp Val Lys Gly Thr Thr Val Gly Gly Cys His
            1220                1225            1230

His Ile Thr Ser Lys Tyr Leu Pro Arg Ser Leu Pro Lys Asp Ser Val
        1235                1240            1245

Ala Val Val Gly Val Ser Ser Pro Gly Arg Ala Ala Lys Ala Val Cys
        1250                1255            1260

Thr Leu Thr Asp Val Tyr Leu Pro Glu Leu Arg Pro Tyr Leu Gln Pro
1265                1270                1275            1280

Glu Thr Ala Ser Lys Cys Trp Lys Leu Lys Leu Asp Phe Arg Asp Val
                1285                1290            1295

Arg Leu Met Val Trp Lys Gly Ala Thr Ala Tyr Phe Gln Leu Glu Gly
            1300                1305            1310

Leu Thr Trp Ser Ala Leu Pro Asp Tyr Ala Arg Xaa Ile Gln Leu Pro
        1315                1320            1325
```

```
Lys Asp Ala Val Val Tyr Ile Asp Pro Cys Ile Gly Pro Ala Thr Ala
           1330                1335                1340

Asn Arg Lys Val Val Arg Thr Thr Asp Trp Arg Ala Asp Leu Ala Val
1345                1350                1355                1360

Thr Pro Tyr Asp Tyr Gly Ala Gln Asn Ile Leu Thr Thr Ala Trp Phe
                1365                1370                1375

Glu Asp Leu Gly Pro Gln Trp Lys Ile Leu Gly Leu Gln Pro Phe Arg
           1380                1385                1390

Arg Ala Phe Gly Phe Glu Asn Thr Glu Asp Trp Ala Ile Leu Ala Arg
                1395                1400                1405

Arg Met Asn Asp Gly Lys Asp Tyr Thr Asp Tyr Asn Trp Asn Cys Val
    1410                1415                1420

Arg Glu Arg Pro His Ala Ile Tyr Gly Arg Ala Arg Asp His Thr Tyr
1425                1430                1435                1440

His Phe Ala Pro Gly Thr Glu Leu Gln Val Glu Leu Gly Lys Pro Arg
                1445                1450                1455

Leu Pro Pro Gly Gln Val Pro
           1460

(2) INFORMATION FOR SEQ ID NO: 4:

(i) SEQUENCE CHARACTERISTICS:
        (A) LENGTH: 249 amino acids
        (B) TYPE: amino acid
        (D) TOPOLOGY: linear (ii) MOLECULE TYPE: protein (xi) SEQUENCE DESCRIPTION: SEQ ID NO: 4:

Met Gln Trp Gly His Cys Gly Val Lys Ser Ala Ser Cys Ser Trp Thr
 1               5                  10                  15

Pro Ser Leu Ser Ser Leu Leu Val Trp Leu Ile Leu Xaa Phe Ser Leu
                20                  25                  30

Pro Tyr Cys Leu Gly Ser Pro Ser Gln Asp Gly Tyr Trp Ser Phe Phe
            35                  40                  45

Ser Glu Trp Phe Ala Pro Arg Phe Ser Val Arg Ala Leu Pro Phe Thr
    50                  55                  60

Leu Pro Asn Tyr Arg Arg Ser Tyr Glu Gly Leu Leu Pro Asn Cys Arg
65                  70                  75                  80

Pro Asp Val Pro Gln Phe Ala Val Lys His Pro Leu Xaa Met Phe Trp
                85                  90                  95

His Met Arg Val Ser His Leu Ile Asp Glu Xaa Val Ser Arg Arg Ile
            100                 105                 110

Tyr Gln Thr Met Glu His Ser Gly Gln Ala Ala Trp Lys Gln Val Val
        115                 120                 125

Gly Glu Ala Thr Leu Thr Lys Leu Ser Gly Leu Asp Ile Val Thr His
    130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Ile
    210                 215                 220
```

```
Val Leu Trp Leu Arg Ile Pro Ala Leu Arg Tyr Val Phe Gly Phe His
225                 230                 235                 240

Trp Pro Thr Ala Thr His His Ser Ser
                    245
```

(2) INFORMATION FOR SEQ ID NO: 5:

(i) SEQUENCE CHARACTERISTICS:
        (A) LENGTH: 265 amino acids
        (B) TYPE: amino acid
        (D) TOPOLOGY: linear (ii) MOLECULE TYPE: protein (xi) SEQUENCE DESCRIPTION: SEQ ID NO: 5:

```
Met Ala His Gln Cys Ala Arg Phe His Phe Phe Leu Cys Gly Phe Ile
1               5                   10                  15

Cys Tyr Leu Val His Ser Ala Leu Ala Ser Asn Ser Ser Ser Thr Leu
                20                  25                  30

Cys Phe Trp Phe Pro Leu Ala His Gly Asn Thr Ser Phe Glu Leu Thr
            35                  40                  45

Ile Asn Tyr Thr Ile Cys Met Pro Cys Ser Thr Ser Gln Ala Ala Arg
        50                  55                  60

Gln Arg Leu Glu Pro Gly Arg Asn Met Trp Cys Lys Ile Gly His Asp
65                  70                  75                  80

Arg Cys Glu Glu Arg Asp His Asp Glu Leu Leu Met Ser Ile Pro Ser
                85                  90                  95

Gly Tyr Asp Asn Leu Lys Leu Glu Gly Tyr Tyr Ala Trp Leu Ala Phe
                100                 105                 110

Leu Ser Phe Ser Tyr Ala Ala Gln Phe His Pro Glu Leu Phe Gly Ile
            115                 120                 125

Gly Asn Val Ser Arg Val Phe Val Asp Lys Arg His Gln Phe Ile Cys
        130                 135                 140

Ala Glu His Asp Gly His Asn Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Leu Phe Ser Ser Trp Leu Val
                180                 185                 190

Leu Asn Ile Ser Trp Phe Leu Arg Arg Ser Pro Val Ser Pro Val Ser
            195                 200                 205

Arg Arg Ile Tyr Gln Ile Leu Arg Pro Thr Arg Pro Arg Leu Pro Val
        210                 215                 220

Ser Trp Ser Phe Arg Thr Ser Ile Val Ser Asp Leu Thr Gly Ser Gln
225                 230                 235                 240

Gln Arg Lys Arg Lys Phe Pro Ser Glu Ser Arg Pro Asn Val Val Lys
                245                 250                 255

Pro Ser Val Leu Pro Ser Thr Ser Arg
                260                 265
```

(2) INFORMATION FOR SEQ ID NO: 6:

(i) SEQUENCE CHARACTERISTICS:
        (A) LENGTH: 183 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Ala Ala Ala Thr Leu Phe Phe Leu Ala Gly Ala Gln His Ile Met
1               5                   10                  15

Val Ser Glu Ala Phe Ala Cys Lys Pro Cys Phe Ser Thr His Leu Ser
                20                  25                  30

Asp Ile Glu Thr Asn Thr Thr Ala Ala Gly Phe Met Val Leu Gln
                35                  40                  45

Asp Ile Asn Cys Phe Arg Pro His Gly Val Ser Ala Ala Gln Glu Lys
            50                  55                  60

Ile Ser Phe Gly Lys Ser Ser Gln Cys Arg Glu Ala Val Gly Thr Pro
65                  70                  75                  80

Gln Tyr Ile Thr Ile Thr Ala Asn Val Thr Asp Glu Ser Tyr Leu Tyr
                    85                  90                  95

Asn Ala Asp Leu Leu Met Leu Ser Ala Cys Leu Phe Tyr Ala Ser Glu
                100                 105                 110

Met Ser Glu Lys Gly Phe Lys Val Ile Phe Gly Asn Val Ser Gly Val
                115                 120                 125

Val Ser Ala Cys Val Asn Phe Thr Asp Tyr Val Ala His Val Thr Gln
130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Ile Ala Cys Leu
                165                 170                 175

Phe Ala Ile Leu Leu Ala Ile
                180
```

(2) INFORMATION FOR SEQ ID NO: 7:

(i) SEQUENCE CHARACTERISTICS:
        (A) LENGTH: 201 amino acids
        (B) TYPE: amino acid
        (D) TOPOLOGY: linear (ii) MOLECULE TYPE: protein (xi) SEQUENCE DESCRIPTION: SEQ ID NO: 7:

```
Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ala
                20                  25                  30

Asp Gly Asn Gly Asp Ser Ser Thr Tyr Gln Tyr Ile Tyr Asn Leu Thr
                35                  40                  45

Ile Cys Glu Leu Asn Gly Thr Asp Trp Leu Ser Ser His Phe Gly Trp
            50                  55                  60

Ala Val Glu Thr Phe Val Leu Tyr Pro Val Ala Thr His Ile Leu Ser
65                  70                  75                  80

Leu Gly Phe Leu Thr Thr Ser His Phe Phe Asp Ala Leu Gly Leu Gly
                    85                  90                  95

Ala Val Ser Thr Ala Gly Phe Val Gly Gly Arg Tyr Val Leu Cys Ser
                100                 105                 110

Val Tyr Gly Ala Cys Ala Phe Ala Ala Phe Val Cys Phe Val Ile Arg
                115                 120                 125

Ala Ala Lys Asn Cys Met Ala Cys Arg Tyr Ala Arg Thr Arg Phe Thr
                130                 135                 140

Asn Phe Ile Val Asp Asp Arg Gly Arg Val His Arg Trp Lys Ser Pro
145                 150                 155                 160
```

```
Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
            180                 185                 190

Arg Thr Ser Ala Glu Gln Trp Glu Ala
        195                 200
```

(2) INFORMATION FOR SEQ ID NO: 8:

(i) SEQUENCE CHARACTERISTICS:
        (A) LENGTH: 173 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Gly Gly Leu Asp Asp Phe Cys Asn Asp Pro Ile Ala Ala Gln Lys
 1               5                  10                  15

Leu Val Leu Ala Phe Ser Ile Thr Tyr Thr Pro Ile Met Ile Tyr Ala
                20                  25                  30

Leu Lys Val Ser Arg Gly Arg Leu Leu Gly Leu Leu His Ile Leu Ile
            35                  40                  45

Phe Leu Asn Cys Ser Phe Thr Phe Gly Tyr Met Thr Tyr Val His Phe
        50                  55                  60

Gln Ser Thr Asn Arg Val Ala Leu Thr Leu Gly Ala Val Val Ala Leu
65                  70                  75                  80

Leu Trp Gly Val Tyr Ser Phe Thr Glu Ser Trp Lys Phe Ile Thr Ser
                85                  90                  95

Arg Cys Arg Leu Cys Cys Leu Gly Arg Arg Tyr Ile Leu Ala Pro Ala
            100                 105                 110

His His Val Glu Ser Ala Ala Gly Leu His Ser Ile Ser Ala Ser Gly
        115                 120                 125

Asn Arg Ala Tyr Ala Val Arg Lys Pro Gly Leu Thr Ser Val Asn Gly
    130                 135                 140

Thr Leu Val Pro Gly Leu Arg Ser Leu Val Leu Gly Gly Lys Arg Ala
145                 150                 155                 160

Val Lys Arg Gly Val Val Asn Leu Val Lys Tyr Gly Arg
                165                 170
```

(2) INFORMATION FOR SEQ ID NO: 9:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO: 9:

```
Met Ala Gly Lys Asn Gln Ser Gln Lys Lys Lys Ser Thr Ala Pro
 1               5                  10                  15

Met Gly Asn Gly Gln Pro Val Asn Gln Leu Cys Gln Leu Leu Gly Ala
                20                  25                  30

Met Ile Lys Ser Gln Arg Gln Gln Pro Arg Gly Gly Gln Xaa Lys Lys
            35                  40                  45

Lys Lys Pro Glu Lys Pro His Phe Pro Leu Ala Ala Glu Asp Asp Ile
        50                  55                  60

Arg His His Leu Thr Gln Thr Glu Arg Ser Leu Cys Leu Gln Ser Ile
65                  70                  75                  80
```

-continued

```
Gln Thr Ala Phe Asn Gln Gly Ala Gly Thr Ala Xaa Leu Ser Ser Ser
                 85                  90                  95

Gly Lys Val Ser Phe Gln Val Glu Phe Met Leu Pro Val Ala His Thr
            100                 105                 110

Val Arg Leu Ile Arg Val Thr Ser Thr Ser Ala Ser Gln Gly Ala Ser
            115                 120                 125
```